(12) United States Patent
Peng et al.

(10) Patent No.: US 8,637,490 B2
(45) Date of Patent: Jan. 28, 2014

(54) ANTI-CANCER AGENTS

(75) Inventors: Xiaohua Peng, Milwaukee, WI (US); Yunyan Kuang, Shanghai (CN); Sheng Cao, Milwaukee, WI (US); Wenbing Chen, Milwaukee, WI (US); Yibin Wang, Milwaukee, WI (US)

(73) Assignee: UWM Research Foundation, Inc., Milwaukee, WI (US)

( * ) Notice: Subject to any disclaimer, the term of this patent is extended or adjusted under 35 U.S.C. 154(b) by 0 days.

(21) Appl. No.: 13/539,471

(22) Filed: Jul. 1, 2012

(65) Prior Publication Data

US 2013/0045949 A1 Feb. 21, 2013

Related U.S. Application Data

(60) Provisional application No. 61/503,957, filed on Jul. 1, 2011.

(51) Int. Cl.
*A61K 31/69* (2006.01)

(52) U.S. Cl.
USPC ............. 514/64; 514/463; 514/643; 514/646; 549/213; 564/8

(58) Field of Classification Search
USPC .......... 514/64, 463, 643, 646; 549/213; 564/8
See application file for complete search history.

(56) References Cited

U.S. PATENT DOCUMENTS 7,678,158 B2 * 3/2010 Lim et al. ........................... 8/405

OTHER PUBLICATIONS

Apopa, P.L., et al. "Phosphorylation of Nrf2 in the Transcription Activation Domain by Casein Kinase 2 (CK2) Is Critical for the Nuclear Translocation and Transcription Activation Function of Nrf2 in IMR-32 Neuroblastoma Cells," J. Biochem. Mol. Toxicol. 2008, p. 63-76, vol. 22.
Arnold, R.S. et al. "Hydrogen peroxide mediates the cell growth and transformation caused by the mitogenic oxidase Noxi," Proc. Natl. Acad. Sci. 2001, p. 5550-5555, vol. 98.
Asquith, J.C. et al., "Metronidazole ("Flagyl") A radiosensitizer of hypoxic cells," British Journal of Radiology, 1974, p. 474-481, vol. 47.
Brookes, P. et al. "The Reaction of Mono- and Di-functional Alkylating Agents with Nucleic Acids," Biochemical Journal, 1961, p. 496-503, vol. 80.
Brown, J.M., "Evidence for acutely hypoxic cells in mouse tumours, and a possible mechanism of reoxygenation," British Journal of Radiology, 1979, p. 650-656, vol. 52.
Brown, J.M., et al. "Exploiting Tumour Hypoxia in Cancer Treatment," Nature Reviews Cancer 2004, p. 437-447, vol. 4.
Buchko, G.W., et al. "DNA-Targeted 2-Nitroimidazoles: Studies of the Influence of the Phenanthridine-Linked Nitroimidazoles, 2-NLP-3 and 2-NLP-4, on DNA Damage Induced by Ionizing Radiation," Radiation Research 2002, p. 302-310, vol. 158.
Buchko, G.W., et al. "Influence of Nitrogen, Oxygen, and Nitroimidazole Radiosensitizers on DNA Damage Induced by Ionizing Radiation," Biochemistry 1993, p. 2186-2193, vol. 32.

Burdon, R.H. "Superoxide and hydrogen peroxide in relation to mammalian cell proliferation," Free Radical Biology and Medicine 1995, p. 775-794, vol. 18.
Cao, S. et al. "ROS-Inducible DNA Cross-Linking Agent as a New Anticancer Prodrug Building Block," Chemistry a European Journal, 2012, p. 3850-3854, vol. 18.
Cecchini, S., et al. "Interstrand Cross-Links: A New Type of gamma-Ray Damage in Bromodeoxyuridine-Substituted DNA," J. Biochemistry 2005, p. 1932-1940, vol. 44.
Chang, M.C.Y. et al. "A Selective, Cell-Permeable Optical Probe for Hydrogen Peroxide in Living Cells" Journal of the American Chemical Society, 2004, p. 15392-15393, vol. 126.
Chen, T., et al. "Investigation of the Origin of the Sequence Selectivity for the 5-Halo-2'-deoxyuridine Sensitization of DNA to Damage by UV-Irradiation," J. Am. Chem. Soc. 2000, p. 3861-3866, vol. 122.
Cheng, G. et al., "Mitochondria-Targeted Drugs Synergize with 2-Deoxyglucose to Trigger Breast Cancer Cell Death," Cancer Research 2012, p. 2634-44, vol. 72, iss. 10.
Cimino, G.D., et al. "Psoralens as photoactive probes of nucleic acid structure and function: organic chemistry, photochemistry, and biochemistry," Annual Review Biochemistry, 1985, p. 1151-1193, vol. 54, iss. 1.
Cook, G.P., et al. "A Novel Mechanism for the Formation of Direct Strand Breaks upon Anaerobic Photolysis of Duplex DNA Containing 5-Bromodeoxyuridine," J. Am. Chem. Soc. 1996, p. 10025-10030, vol. 118.
Denny, W.A. "Prodrug strategies in cancer therapy," Eur. J. Med. Chem. 2001, p. 577-595, vol. 36.
Di Antonio, M., et al. "Quinone Methides Tethered to Naphthalene Diimides as Selective G-Quadruplex Alkylating Agents," J. Am. Chem. Soc. 2009, p. 13132-13141, vol. 131.
Dickinson, B.C. et al. "A Targetable Fluorescent Probe for Imaging Hydrogen Peroxide in the Mitochondria of Living Cells," Journal of American Chemical Society 2008, p. 9638-9639, vol. 130.
Dong, Q. et al. "A Structural Basis for a Phosphoramide Mustard-Induced DNA interstrand cross-link at 5'-d(GAC)," Proc. Natl. Academy of Science, U.S.A. 1995, p. 12170-12174, vol. 92.
Dronkert, M.L.G. et al. "Repair of DNA interstrand cross-links," Mutation Research/DNA Repair 2001, p. 217-247, vol. 486.
Evans, S. M., et al. "Detection of Hypoxia in Human Squamous Cell Carcinoma by EF5 Binding," J. Cancer Res. 2000, p. 2018-2024, vol. 60.
Ferlin, M.G. et al. "Synthesis and antiproliferative activity of some new DNA-targeted alkylating pyrroloquinolines," Bioorganic Medicinal Chemistry 2004, p. 771-777, vol. 12.
Haraguchi, K. et al. "Synthesis and Characterization of Oligodeoxynucleotides Containing Formamidopyrimidine Lesions and Nonhydrolyzable Analogues," Journal of American Chemical Society, 2002, p. 3263-3269, vol. 124.
Hong, I.S. et al. "Mild Generation of 5-(2'-Deoxyuridinyl)methyl Radical from a Phenyl Selenide Precurson," Org. Lett. 2004, p. 5011-5013, vol. 6.
Hong, I.S. et al. "Radiosensitization by a Modified Nucleotide that Produces DNA Interstrand Cross-Links Under Hypoxic Conditions," J. Am. Chem. Soc. 2006, p. 2230-2231, vol. 128.
Hong, I.S., et al. "DNA Interstrand Cross-Link Formation Initiated by Reaction between Singlet Oxygen and a Modified Nucleotide," J. Am. Chem. Soc. 2005, p. 3692-3693, vol. 127.

(Continued)

*Primary Examiner* — Kamal Saeed
*Assistant Examiner* — Janet L Coppins
(74) *Attorney, Agent, or Firm* — Michael Best & Friedrich LLP

(57) ABSTRACT

Described herein are compounds that may be selectively activated to produce active anti-cancer agents in tumor cells. Also disclosed are pharmaceutical compositions comprising the compounds, and methods of treating cancer using the compounds.

10 Claims, 13 Drawing Sheets

(56) References Cited

OTHER PUBLICATIONS

Hong, I.S. et al. "Oxygen Independent DNA Interstrand Cross-Link Formation by a Nucleotide Radical," Journal of American Chemical Society, 2006, p. 485-491, vol. 128.

Hong, I.S. et al. "DNA Interstrand Cross-Link Formation Initiated by Reaction between Singlet Oxygen and a Modified Nucleotide," Journal of the American Chemical Society 2005, p. 10510-10511, vol. 127.

Huang, B.S., et al. "Synthesis and Properties of Alkylated Imidazoles," J. Heterocyclic Chem. 1979, p. 811-813, vol. 16.

Kantor, G. J., et al. "Action Spectra for Killing Non-Dividing Normal Human and Xeroderma Pigmentosum Cells," Photochemistry and Photobiology. 1980, p. 459-464, vol. 31.

Karton-Lifshin, N., et al. "A Unique Paradigm for a Turn-On Near-Infrared Cyanine-Based Probe: Noninvasive Intravital Optical Imaging of Hydrogen Peroxide," J. Am. Chem. Soc. 2011, p. 10960-10965, vol. 133.

Kawanishi, S. et al. "Oxidative and nitrative DNA damage in animals and patients with inflammatory diseases in relation to inflammation-related carcinogenesis," Biol. Chem. 2006, p. 365-372, vol. 387.

Kim, E. et al. "A bifunctional platinum(II) antitumor agent that forms DNA adducts with affinity for the estrogen receptor," Journal of Inorganic Biochemistry, 2009, p. 256-261, vol. 103.

Kuang, Y. et al. "Hydrogen Peroxide Inducible DNA Cross-Linking Agents: Targeted Anticancer Prodrugs," J. Am. Chem. Soc. 2011, p. 19278-19281, vol. 133.

Kuang, Y. et al. "Hypoxia-Selective DNA Interstrand Cross-Link Formation by Two Modified Nucleosides," Chemistry a European Journal, 2012 DOI: 10.1002/chem.201201960.

Kuivila, H.G. "Electrophilic Displacement Reactions III. Kinetics of the Reaction between Hydrogen Peroxide and Benzeneboronic Acid," Journal of American Chem. Society, 1954, p. 870-874, vol. 76.

Kuivila, H.G. et al. "Organic and Biological Chemistry, Electrophilic Displacement Reactions. IX. Effects of Substituents on Rates of Reactions between Hydrogen Peroxide and Benzeneboronic Acid," Journal of American Chemical Society, 1957, p. 5659-5662, vol. 79.

Lee, Y.J., et al. "Hydrogen Peroxide inhibits activation, not activity, of cellular caspase-3 in vivo," Free Radical Biol. Med. 2000, p. 684-692, vol. 29.

Lim, S.D. et al. "Increased Nox1 and Hydrogen Peroxide in Prostate Cancer," The Prostate 2005, p. 200-207, vol. 62.

Lin, S.W. et al. "Synthesis and structure-analgesic activity relationships of a novel series of monospirocyclopiperazinium salts (MSPZ)," Bioorganic & Medicinal Chemistry Letters, 2011, p. 940-943, vol. 21.

Lo, L.C. et al. "Development of highly selective and sensitive probes for hydrogen peroxide," Chemical Communications 2003, p. 2728-2729, iss. 21.

Lopez-Lazaro, M. "HIF-1: Hypoxia-inducible factor or Dysoxia-inducible factor?" The FASEB Journal 2006, p. 828-832, vol. 20.

Lopez-Lazaro, M. "Dual role of hydrogen peroxide in cancer: Possible relevance to cancer chemoprevention and therapy," Cancer Letters 2007, p. 1-8, vol. 252.

Major Jourden, J.L. et al. "Hydrogen Peroxide Activated Matrix Metalloproteinase Inhibitors: A Prodrug Approach," Angew Chem. Int. Ed. 2010, p. 6795-6797, vol. 49.

Maxam, A.M., et al. "A New Method for Sequencing DNA," Proc. Natl. Acad. Sci. 1977, p. 560-564, vol. 74.

Millard, J.T. et al. "Sequence preferences of DNA interstrand crosslinking agents: quantitation of interstrand crosslink locations in DNA duplex fragments containing multiple crosslinkable sites," Nucleic Acids Res. 1991, p. 1885-1892, vol. 19.

Miller, E.W. et al. "Molecular imaging of hydrogen peroxide produced for cell-signaling," Nature Chemical Biology. 2007, p. 263-267, vol. 3.

Miller, E.W. et al. "Sequence preferences of DNA interstrand crosslinking agents: quantitation of interstrand crosslink locations in DNA duplex fragments containing multiple crosslinkable sites," Journal of American Chemical Society, 2005, p. 16652-16659, vol. 127.

Modica, E., et al. "Alkylation of Amino Acids and Glutathione in Water by o-Quinone Methide. Reactivity and Selectivity," J. Org. Chem. 2001, p. 41-52, vol. 66.

Mukhopadhyay, P. et al. "Mitochondrial-targeted antioxidants represent a promising approach for prevention of cisplatin-induced nephropathy," Free Radic Biol Med 2012, p. 497-506, vol. 52.

Nakatani, K., et al. "Highly Efficient Photochemical Generation of o-Quinone Methide from Mannich Bases of Phenol Derivatives," Tetrahedron Lett. 1997, p. 5005-5008, vol. 38.

Newcomb, M. "Competition Methods and Scales for Alkyl Radical Reaction Kinetics," Tetrahedron 1993, p. 1151-1176, vol. 49.

Noll, D.M. et al. "Formation and Repair of Interstrand Cross-Links in DNA," Chem. Rev. 2006, 277-301, vol. 106.

Oberley, T.D. "Oxidative damage and cancer," American Journal of Pathology 2002, p. 403-408, vol. 160.

Oberley, T.D. et al. "Antioxidant enzyme levels in cancer" Histology and Histopathology 1997, p. 525-535, vol. 12.

Ogata, R., et al. "Contacts between the lac repressor and thymines in the lac operator," Proc. Natl. Acad. Sci. 1977, p. 4973-4976, vol. 74.

Okamoto, M. et al. "Transformation in vitro of a nontumorigenic rat urothelial cell line by hydrogen peroxide" Cancer Res. 1996, p. 4649-4653, vol. 56.

Okamoto, M. et al. "Tumorigenic conversion of a non-tumorigenic rat urothelial cell line by overexpression of H2O2-generating peroxisomal fatty acyl-CoA oxidase," International Journal of Cancer 1997, p. 716-721, vol. 70.

Pelicano, H. et al. "ROS stress in cancer cells and therapeutic implications," Drug Resist Update, 2004, p. 97-110, vol. 7.

Peng, X. et al. "Hypoxia-selective DNA interstrand cross-Link formation by a modified nucleoside," Gordon Research Conference: Nucleosides, Nucleotides & Oligonucleotides. Jul. 3-Jul. 8, 2011, Salve Regina University, Newport, RI.

Peng, X. et al. "ROS-activated anticancer prodrugs: a new strategy for tumor-specific damage," Therapeutic Delivery, 2012, p. 823-833, vol. 3, iss. 7.

Peng, X. et al. "Interstrand Cross-Link Formation in Duplex and Triplex DNA by Modified Pyrimidines," Journal of American Chemical Society, 2008, p. 10299-10306, vol. 130.

Peng, X. et al. "Protein Binding has a large effect on Radical Mediated DNA damage," J. Am. Chem. Soc. 2008, p. 12890-12891, vol. 130.

Polytarchou, C. et al. "Hydrogen peroxide stimulates proliferation and migration of human prostate cancer cells through activation of activator protein-1 and up-regulation of the heparin affin regulatory peptide gene" The Journal of Biological Chemistry 2005, p. 40428-40435, vol. 280.

Price, G.A., et al. "First Structurally Confirmed Example of the Formation of a Gold(III) Carbon Bond via Transmetallation with a Boroxine," Dalton Trans. 2011, p. 11696-11697, vol. 40.

Price, M.A., et al. "Using Hydroxyl Radical to Probe DNA Structure," Methods Enzymol. 1992, p. 194-219, vol. 212.

Richter, S.N. et al. "Binol Quinone Methides as Bisalkylating and DNA Cross-Linking Agents," Journal of American Chemical Society, 2004, p. 13973-13979, vol. 126.

Rink, S.M. et al. "Covalent Structure of a Nitrogen Mustard-Induced DNA Interstrand Cross-Link: An N7 to N7 Linkage of Deoxyguanosine Residues at the Duplex Sequence 5'-d(GNC)," Journal of American Chemical Society, 1993, p. 2551-2557, vol. 115.

Rink, S.M. et al. "Synthesis and biological activity of DNA damaging agents that form decoy binding sites for the estrogen receptor," Proc. Natl. Acad. Sci. U.S.A. 1996, p. 15063-15068, vol. 93.

Romieu, A., "Synthesis and UV Photolysis of Oligodeoxynucleotides that contain 5-(Phenylthiomethyl)-2'-deoxyuridine: A specific photolabile precursor of 5-(2'-deoxyuridilyl)methyl radical," J. Org. Lett. 2000, p. 1085-1088, vol. 2.

Roy, M. B., et al. "Photosensitization of DNA Bases by 4(5)-Nitroimidazole: A Steady State and Flash Photolysis Study," J. Chem. Soc. Faraday Trans. 1995, p. 1191-1196, vol. 91.

Shawn, M.H. et al. "DNA adducts formed by a novel antitumor agent 11beta-dichloro in vitro and in vivo," Mol. Cancer Ther 2006, p. 977-984, vol. 5.

(56) References Cited

OTHER PUBLICATIONS

Sherman, S.E., et al. "Structural Aspects of Platinum Anticancer Drug Interactions with DNA," Chem. Rev. 1987, p. 1153-1181, vol. 87.

Solanki, V. et al. "Diminution of mouse epidermal superoxide dismutase and catalase activities by tumor promoters," Carcinogenesis 1981, p. 1141-1146, vol. 2.

Srikun, D. et al. "An ICT-Based approach to ratiometric fluorescence imaging of hydrogen peroxide produced in living cells," Journal of American Chemical Society, 2008, p. 4596-4597, vol. 130.

Sugiyama, H., et al. "Highly Sequence Selective Photoreaction of 5-Bromouracil-Containing Deoxyhexanucleotides," J. Am. Chem. Soc. 1990, p. 6720-6721, vol. 112.

Suh, Y.A. et al. "Cell transformation by the superoxide-generating oxidase Moxi," Nature 1999, p. 79-82, vol. 401.

Szatrowski, T.P. et al. "Production of Large Amounts of Hydrogen Peroxide by Human Tumor Cells," Cancer Res. 1991, p. 794-798, vol. 51.

Tercel, M., et al. "Nitrobenzyl Mustard quaternary salts: a new class of hypoxia-selective cytotoxins showing very high in vitro selectivity," J. Med. Chem. 1993, p. 2578-2579, vol. 36.

Thomlinson, R. H., et al. "The histological structure of some human lung cancers and the possible implications for radiotherapy," J. Cancer 1955, p. 539-549, vol. 9.

Tomasz, M., "Mitomycin C: small, fast and deadly (but very selective)," Chem. Biol. 1995, p. 575-579, vol. 2.

Townsend, L.B. "The Chemistry of Nucleosides and Nucleotides," Plenum Press: New York and London, 1994; vol. 3.

Toyokuni, S. et al. "Persistent oxidative stress in cancer," FEBS Lett. 1995, p. 1-3, vol. 358.

Trachootham, D. et al. "Targeting Cancer cells by ROS-mediated mechanisms: a radical therapeutic approach?" Nature Rev. 2009, p. 579-591, vol. 8.

Veldhuyzen, W.F. et al. "A transient product of DNA alkylation can be stabilized by binding localization," Journal of American Chemical Society, 2003, p. 14005-14013, vol. 125.

Verga, D., et al. "Photogeneration and Reactivity of Naphthoquinone Methides as Purine Selective DNA Alkylating Agents," J. Am. Chem. Soc. 2010, p. 14625-14637, vol. 132.

Von Sonntag, C. "The Chemical Basis of Radiation Biology," Taylor & Francis: London, 1987.

Wang, H. et al. "Dynamic Cross-Linking is Retained in Duplex DNA after Multiple Exchange of Strands," Angewandte Chemie International Edition 2010, p. 5957-5960, vol. 49.

Wang, L. et al. "Cyclopalladated Ferrocenylimine as Efficient Catalyst for the Syntheses of Arylboronate Esters," Advanced Synthesis & Catalysis, 2010, p. 2002-2010, vol. 352.

Wang, P. et al. "A Potent, Water-Soluble and Photoinducible DNA Cross-Linking Agent," Journal of American Chemical Society, 2003, p. 1116-1117, vol. 125.

Wang, Y. "HPLC Isolation and Mass Spectrometric Characterization of Two Isomers of Thymine Glycols in Oligodeoxynucleotides," Chem. Res. Toxicol. 2002, p. 671-676, vol. 15.

Weinert, E.E. et al. "Substituents on Quinone Methides Strongly Modulate Formation and Stability of their Nucleophilic Adducts," Journal of American Chemical Society, 2006, p. 11940-11947, vol. 128.

Weng, X. et al. "Synthesis and Biological Studies of Inducible DNA Cross-Linking Agents," Angewandte Chemie International Edition 2007, p. 8020-8023, vol. 46.

White, J.R., et al. "A Modular Approach to Catalytic Synthesis Using a Dual-Functional Linker for Click and Suzuki Coupling Reactions," Tetrahedron Letters, 2010, p. 3913-3917, vol. 51.

Wilson, W.A., et al. "Radiation-activated prodrugs as hypoxia-selective cytotoxins: model studies with nitroarylmethyl quaternary salts," Anti-Cancer Drug Des. 1998, p. 663-685, vol. 13.

Yang, W.Q. et al. "Biological and Medicinal Applications of Boronic Acids," Boronic Acids: Preparation and Applications in Organic Synthesis and Medicine, ed. Hall, D.G. Wiley-VCH, Weinheim, 2005, p. 481-512.

Zeng, Q. et al. "Tandem Quinone Methide Generation for Cross-Linking DNA," J. Org. Chem. 1996, p. 9080-9081, vol. 61.

Zhang, Q., et al. "Independent generation of the 5-hydroxy-5,6-dihydrothymidin-6-yl radical and its reactivity in dinucleoside monophosphates," J. Am. Chem. Soc. 2004, p. 13287-13297, vol. 126.

Zhang, Q., et al. "The reactivity of the 5-hydroxy-5,6-dihydrothymidin-6-yl radical in oligodeoxyribonucleotides," Chem. Res. Toxicol. 2005, p. 1897-1906, vol. 18.

Zieba, M. et al. "Comparison of hydrogen peroxide generation and the content of lipid peroxidation products in lung cancer tissue and pulmonary parenchyma," Respir Med. 2000, p. 800-805, vol. 94.

Zysman-Colman, E. et al. "Synthesis of arylbromides from arenes and N-bromosuccinimide (NBS) in acetonitrile—A convenient method for aromatic bromination," Canadian Journal of Chemistry, 2009, p. 440-447, vol. 87.

\* cited by examiner

A.

B.

C.

```
                        SEQUENCE LISTING

<160> NUMBER OF SEQ ID NOS: 6

<210> SEQ ID NO 1
<211> LENGTH: 49
<212> TYPE: DNA
<213> ORGANISM: Artificial Sequence
<220> FEATURE:
<223> OTHER INFORMATION: Synthetic Oligonucleotide

<400> SEQUENCE: 1
gcctagttct tttaattact tgcaatgcaa gtaattaaag cttgatctg           49

<210> SEQ ID NO 2
<211> LENGTH: 49
<212> TYPE: DNA
<213> ORGANISM: Artificial Sequence
<220> FEATURE:
<223> OTHER INFORMATION: Synthetic Oligonucleotide

<400> SEQUENCE: 2
cggatcaaga aaattaatga acgttacgtt cattaatttc gaactagac           49

<210> SEQ ID NO 3
<211> LENGTH: 16
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (9)..(9)
<223> OTHER INFORMATION: n is compound 53a
<220> FEATURE:
<221> NAME/KEY: misc_feature
<222> LOCATION: (10)..(10)
<223> OTHER INFORMATION: n is a, c, g, or t

<400> SEQUENCE: 3
agatggannn aggtac                                                16

<210> SEQ ID NO 4
<211> LENGTH: 16
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (8)..(8)
<223> OTHER INFORMATION: n is a, c, g, or t
<220> FEATURE:
```

```
<221> NAME/KEY: misc_feature
<222> LOCATION: (10)..(10)
<223> OTHER INFORMATION: n is a, c, g, or t

<400> SEQUENCE: 4
tctacctnan tccatg                                                       16

<210> SEQ ID NO 5
<211> LENGTH: 16
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (9)..(9)
<223> OTHER INFORMATION: n is compound 53b
<220> FEATURE:
<221> NAME/KEY: misc_feature
<222> LOCATION: (10)..(10)
<223> OTHER INFORMATION: n is a, c, g, or t

<400> SEQUENCE: 5
agatggannn aggtac                                                       16

<210> SEQ ID NO 6
<211> LENGTH: 16
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t

<400> SEQUENCE: 6
tctacctnan tccatg                                                       16
```

ANTI-CANCER AGENTS

CROSS-REFERENCE TO RELATED APPLICATIONS

This application claims priority to U.S. Provisional Patent Application No. 61/503,957, filed on Jul. 1, 2011, the entire contents of which are hereby incorporated by reference.

SEQUENCE LISTING

The instant application contains a Sequence Listing which has been submitted in text format via EFS-Web and is hereby incorporated by reference in its entirety. Said text copy, created on Oct. 30, 2012, is named ASFILED_SequenceListing-Text and is 2,270 bytes in size.

STATEMENT REGARDING FEDERALLY SPONSORED RESEARCH

This invention was made with United States government support awarded by the National Cancer Institute, Grant No. 1R15CA152914-01. The United States Government has certain rights in this invention.

BACKGROUND

Many cancer cells exhibit a disturbed intracellular redox balance, making them distinctively different from their "healthy" counterparts. Among these differences, some cancer cells are hypoxic and have an increase in bioreductive processes, while others have high intracellular concentrations of reactive oxygen species due to oxidative stress.

There is a continuing need for new anti-cancer agents, particularly those that have fewer toxic side-effects.

SUMMARY

In one aspect, the disclosure provides a compound of formula (I):

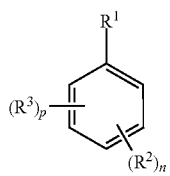

(I)

wherein:

each $R^1$ is independently —B(XR')$_2$, wherein each X is independently selected from O and S, and each R' is independently selected from hydrogen and alkyl, or two R' are taken together to form an optionally substituted 5- to 8-membered ring;

each $R^2$ is independently selected from optionally substituted alkyl, alkoxy, amino, halo, and —CH$_2$—N(R$^a$)$_3$⊕;

each $R^3$ is independently selected from:

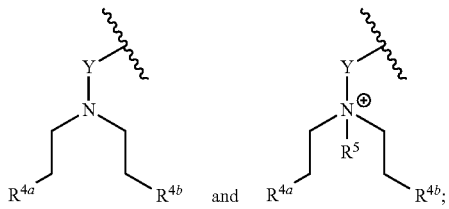

each $R^{4a}$ and $R^{4b}$ is independently selected from halo and —OSO$_2$R$^a$;

each Y is independently a bond or —CH$_2$—;

each $R^5$ is independently C$_1$-C$_4$ alkyl;

n is 0, 1 or 2;

p is 1 or 2;

each $R^a$ is independently selected from optionally substituted alkyl;

wherein if the compound of formula (I) bears a positive charge, it further comprises at least one counterion Z⊖.

In another aspect, the disclosure provides a compound of formula (Ia):

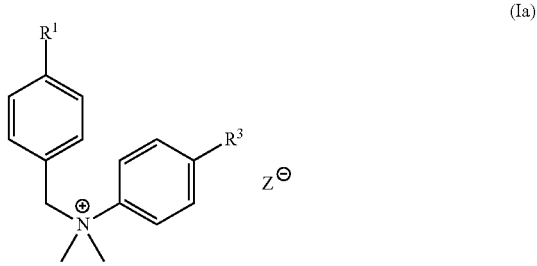

(Ia)

wherein:

$R^1$ is —B(XR')$_2$, wherein each X is independently selected from O and S, and each R' is independently selected from hydrogen and alkyl, or two R' are taken together to form an optionally substituted 5- to 8-membered ring;

$R^3$ is:

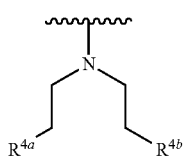

wherein each $R^{4a}$ and $R^{4b}$ is independently selected from halo and —OSO$_2$R$^a$; and each $R^a$ is independently selected from optionally substituted alkyl.

In another aspect, the disclosure provides a compound of formula (II):

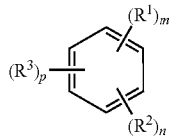
(II)

wherein:

each $R^1$ is independently —B(XR')$_2$, wherein each X is independently selected from O and S, and each R' is independently selected from hydrogen and alkyl, or two R' are taken together to form an optionally substituted 5- to 8-membered ring;

each $R^2$ is independently selected from optionally substituted alkyl, alkoxy, amino, halo and nitro;

each $R^3$ is independently selected from:

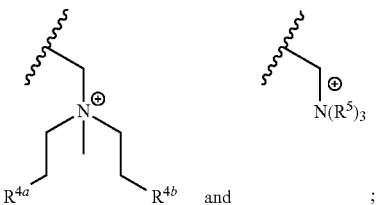

each $R^{4a}$ and $R^{4b}$ is independently selected from halo and —OSO$_2$R$^b$;

each $R^5$ is independently optionally substituted alkyl;

m is 1 or 2;

n is 0, 1 or 2;

p is 2; and wherein the compound further comprises at least one counterion Z⊖.

In another aspect, the disclosure provides a compound of formula (IIa):

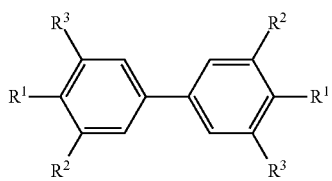
(IIa)

each $R^1$ is independently —B(XR')$_2$, wherein each X is independently selected from O and S, and each R' is independently selected from hydrogen and alkyl, or two R' are taken together to form an optionally substituted 5- to 8-membered ring;

each $R^2$ is independently selected from hydrogen, optionally substituted alkyl, alkoxy, amino, halo and nitro;

each $R^3$ is independently selected from:

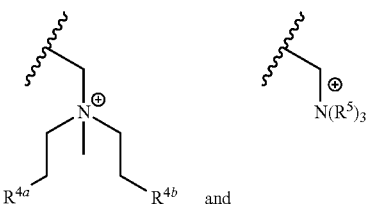

each $R^{4a}$ and $R^{4b}$ is independently selected from halo and —OSO$_2$R$^b$;

each $R^5$ is independently optionally substituted alkyl;

m is 1 or 2;

n is 0, 1 or 2;

p is 2; and wherein the compound further comprises at least one counterion Z⊖.

In another aspect, the disclosure provides a compound of formula (III):

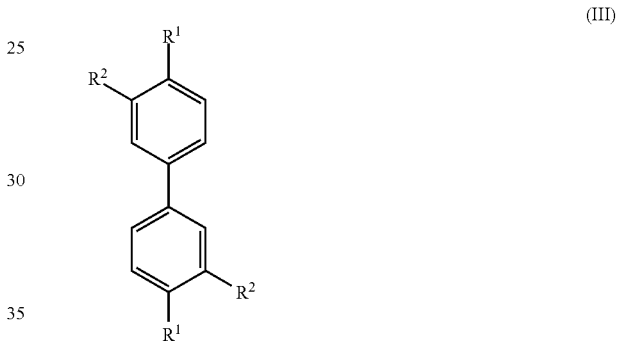
(III)

wherein:

each $R^1$ is independently selected from selected from the group consisting of:

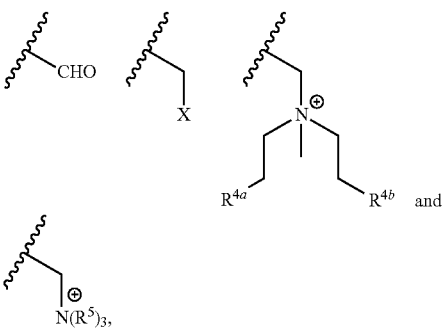

wherein at least one $R^1$ is other than —CHO;

each $R^2$ is independently selected from an electron-withdrawing group;

each X is independently halo;

each $R^{4a}$ and $R^{4b}$ is independently selected from halo and —OSO$_2$R$^b$; and each $R^5$ is independently selected from optionally substituted alkyl;

wherein if the compound of formula (III) bears a positive charge, it further comprises at least one counterion Z⊖.

In another aspect, the disclosure provides a compound of formula (IIIa):

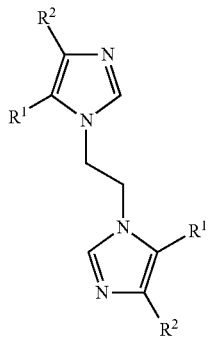

(IIIa)

wherein:
each $R^1$ is independently selected from selected from the group consisting of:

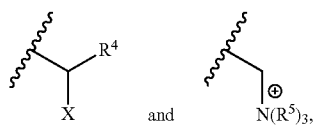

each $R^2$ is independently selected from an electron-withdrawing group;
each X is independently halo;
each $R^4$ is independently selected from the group consisting of —H and —COO(alkyl), and
each $R^5$ is independently selected from optionally substituted alkyl;
wherein if the compound of formula (III) bears a positive charge, it further comprises at least one counterion $Z^\ominus$.

In another aspect, the disclosure provides a compound of formula (IV):

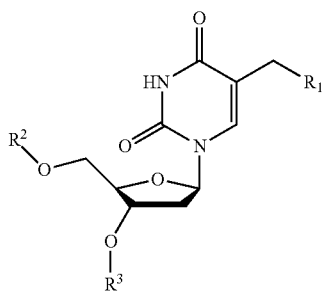

(IV)

wherein:
$R^1$ is selected from the group consisting of:

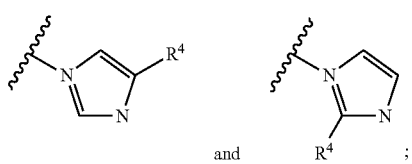

$R^2$ is selected from the group consisting of —H and a hydroxy protecting group;

$R^3$ is selected from the group consisting of —H and —P(N(CH(CH$_3$)$_2$)$_2$)(OCH$_2$CH$_2$CN); and each $R^4$ is independently an electron withdrawing group.

In another aspect, the disclosure provides a compound of formula (Va), (Vb), (Vc), (Vd), (Ve) or (Vf):

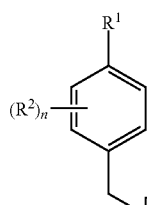

(Va)

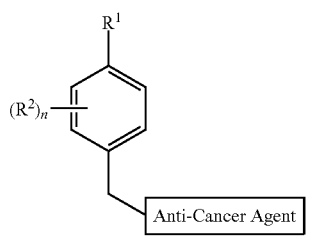

(Vb)

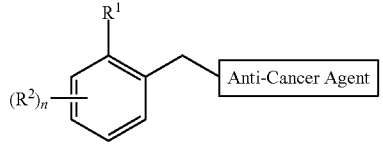

(Vc)

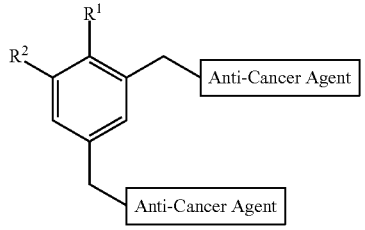

(Vd)

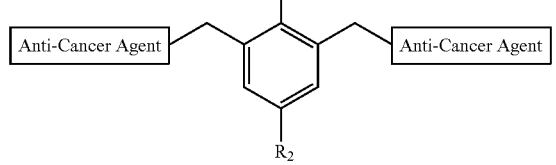

(Ve)

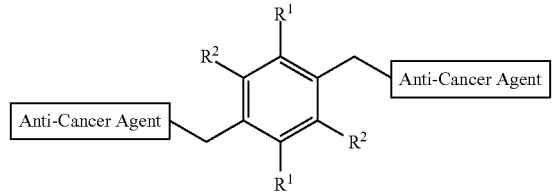

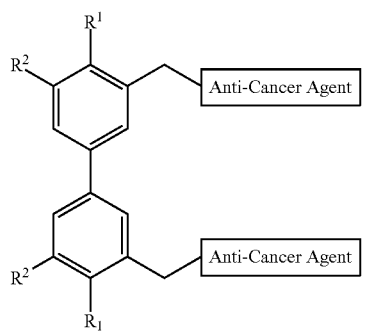

(Vf)

wherein:

each $R^1$ is independently —$B(XR')_2$, wherein each X is independently selected from O and S, and each R' is independently selected from hydrogen and alkyl, or two R' are taken together to form an optionally substituted 5- to 8-membered ring;

each $R^2$ is independently selected from optionally substituted alkyl, alkoxy, amino, halo, and —$CH_2$—$N(R^a)_3$; and n is 0, 1 or 2.

In another aspect, the disclosure provides a pharmaceutical composition comprising a compound of formula (I), (Ia), (II), (IIa), (III), (IIIa), (IV), (Va), (Vb), (Vc), (Vd), (Ve) or (Vf) as described herein.

In another aspect, the disclosure provides a method of treating cancer in a subject in need of treatment, comprising administering the subject a therapeutically effective amount of a compound of formula (I), (Ia), (II), (IIa), (III), (IIIa), (IV), (Va), (Vb), (Vc), (Vd), (Ve) or (Vf) as described herein.

In another aspect, the disclosure provides a method of reducing the proliferation of a cancer cell, comprising contacting the cancer cell with an effective amount of a compound described herein, such as a compound of formula (I), (Ia), (II), (IIa), (III), (IIIa), (IV), (Va), (Vb), (Vc), (Vd), (Ve) or (Vf) as described herein.

Other aspects and embodiments will become apparent in light of the following description and drawings.

BRIEF DESCRIPTION OF THE DRAWINGS

FIG. 2 depicts mean growth percentages of various human cancer cell lines in the presence of 10 μM of a compound described in Example 12: (A) Compound 6; (B) Compound 7; (C) Compound 8; (D) Compound 10; and (E) Compound 17a.

DETAILED DESCRIPTION

Figure 1:
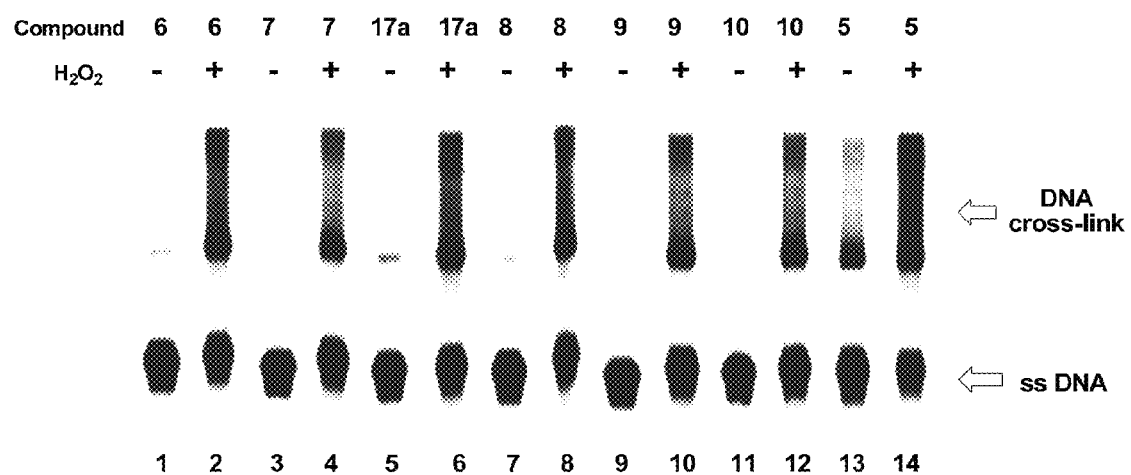
FIG. 1 depicts a denaturing PAGE gel of DNA samples treated with compounds described herein, in the presence or absence of hydrogen peroxide.
Figure 2A:
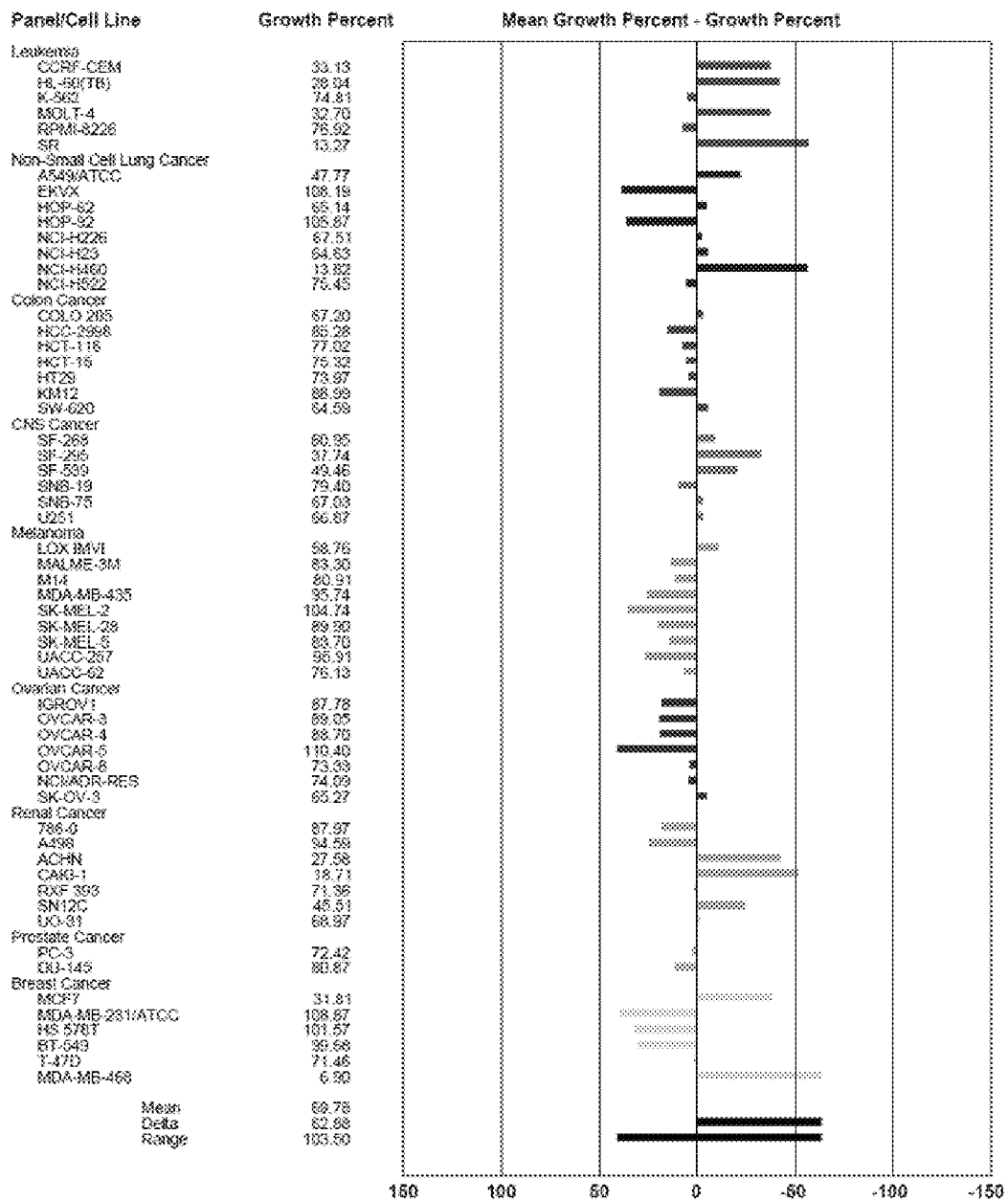
Figure 2B:
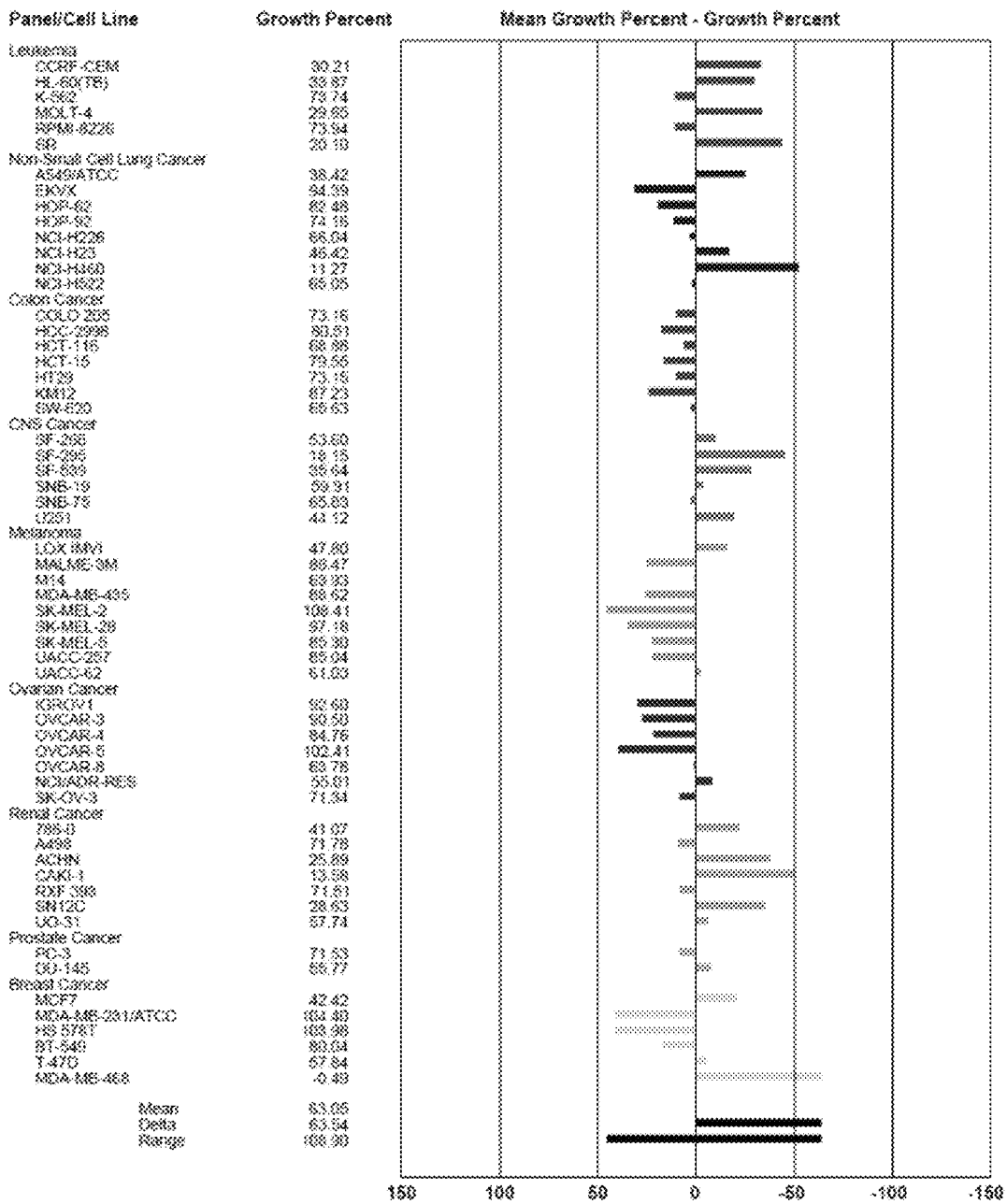
Figure 2C:
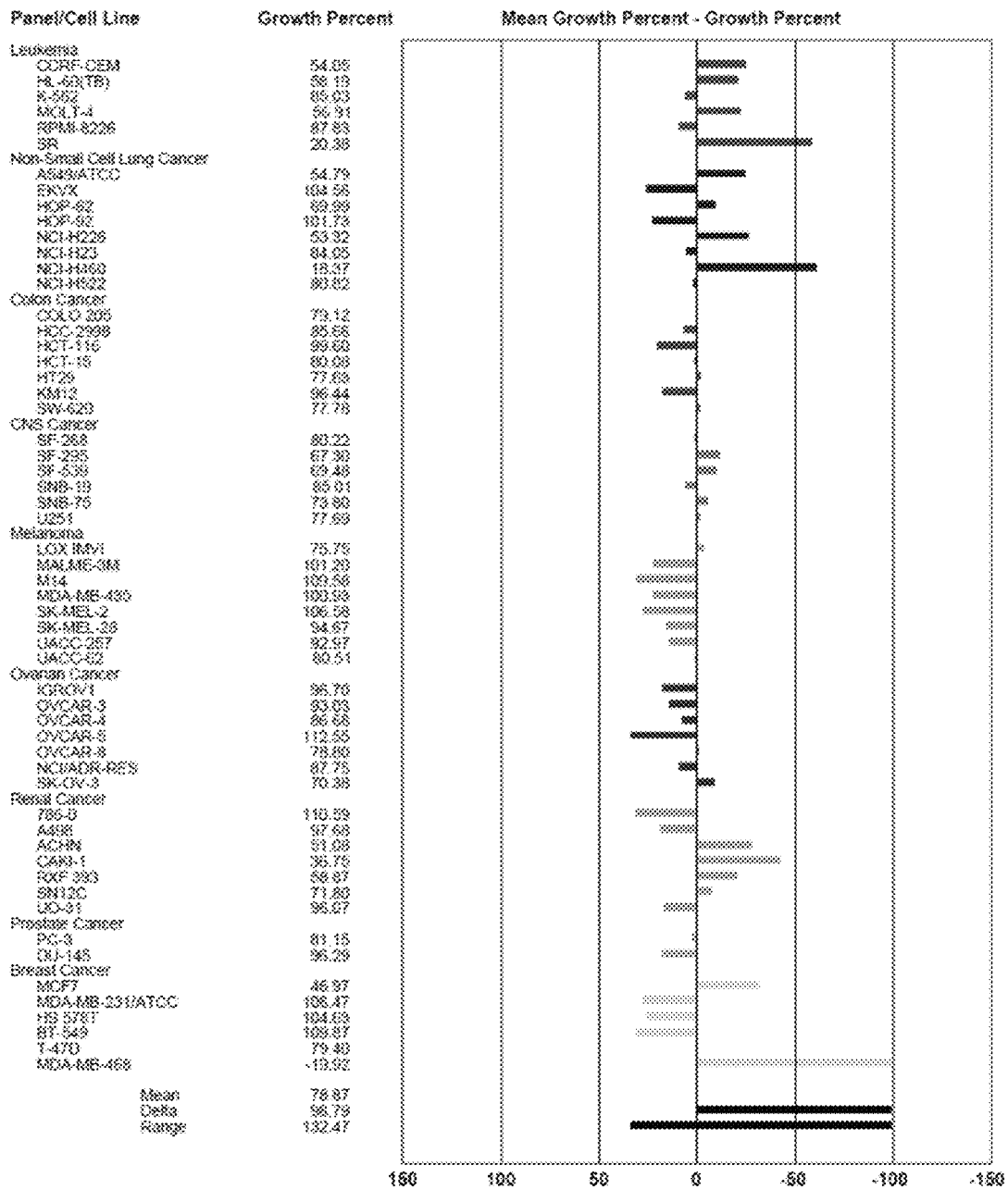
Figure 2D:
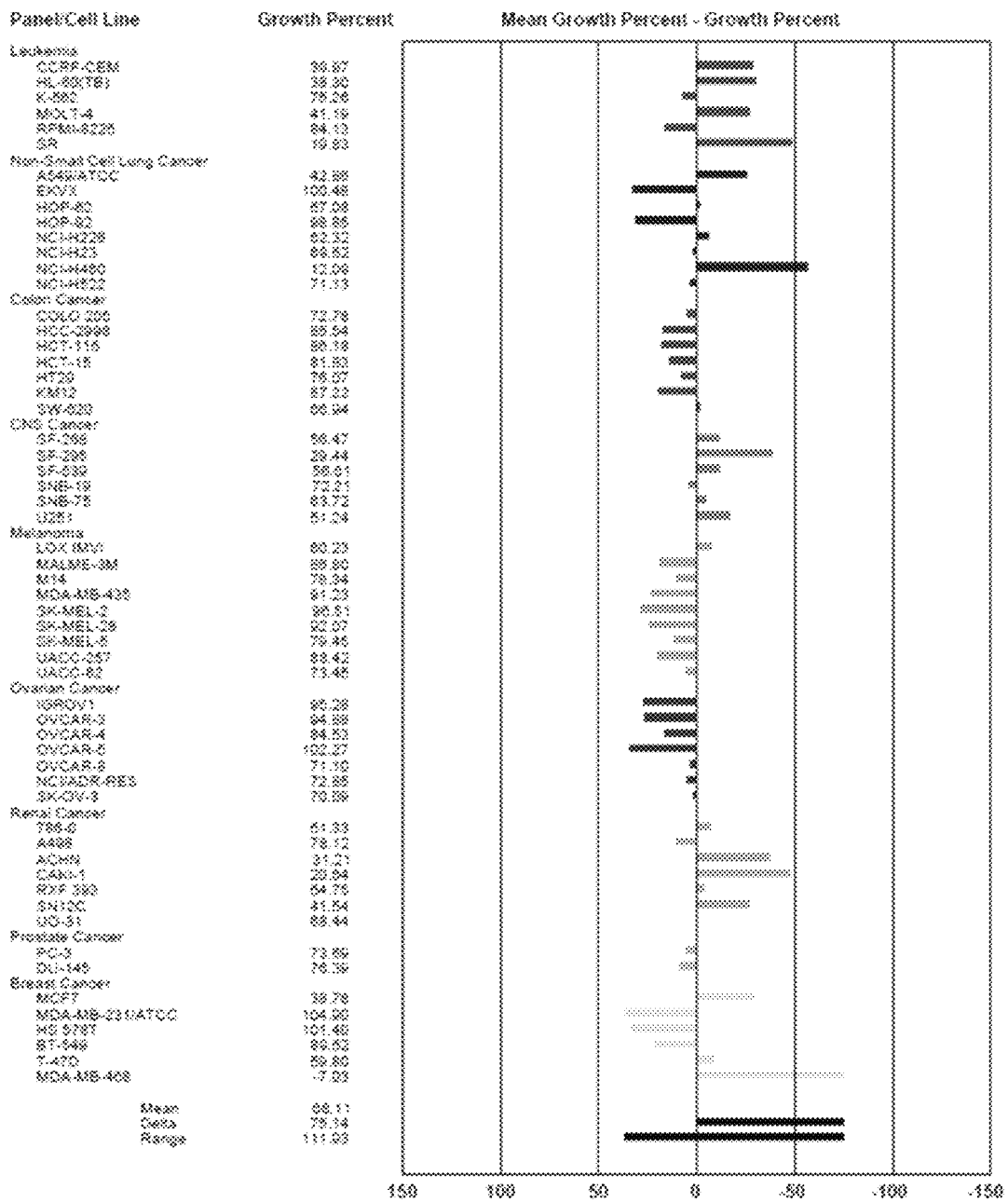
Figure 2E:
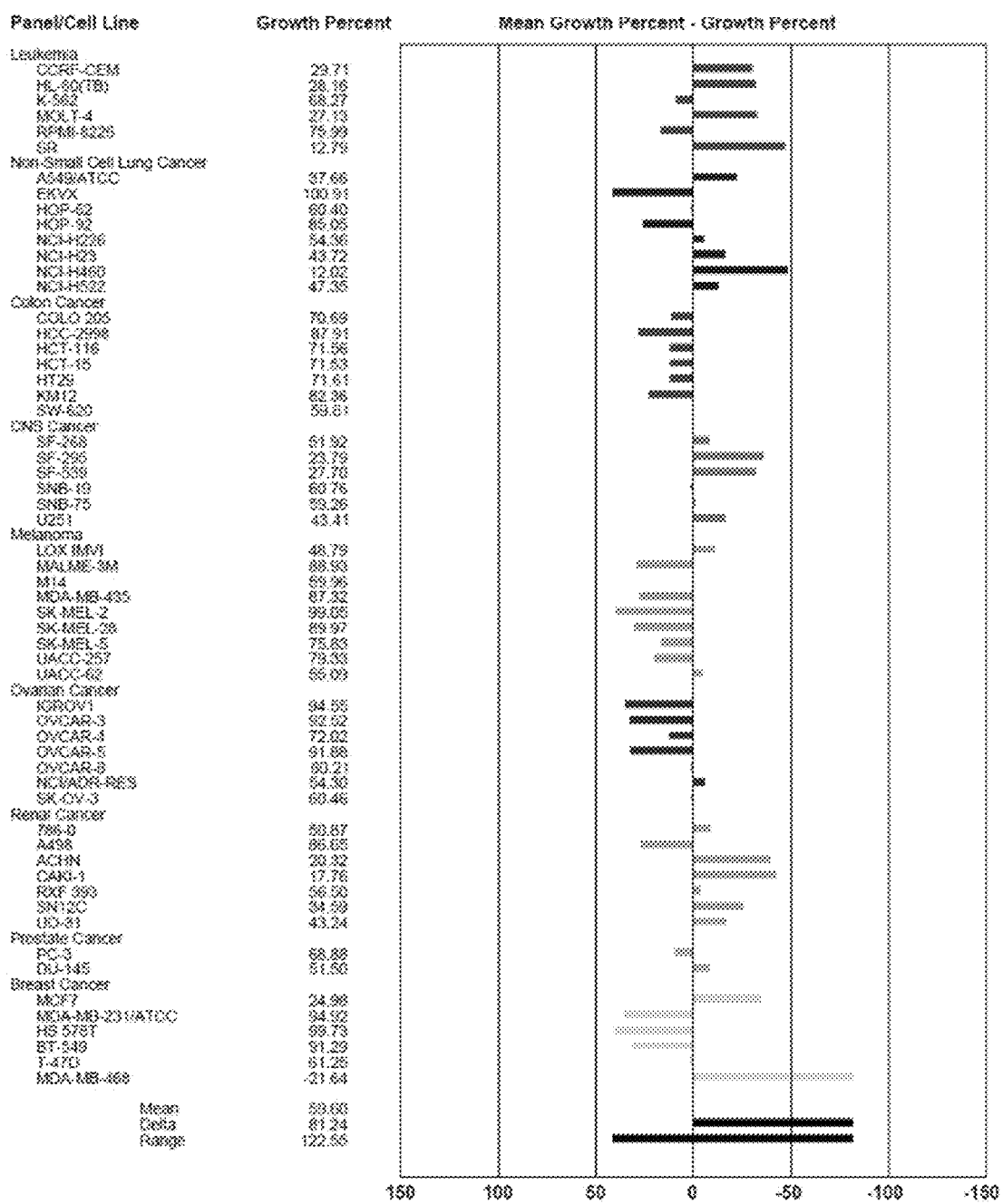

Described herein are compounds that may be selectively activated in cancer cells to release anti-cancer agents. For example, some compounds may be activated by reactive oxygen species, such as hydrogen peroxide, which may be found in elevated levels in certain types of cancer cells. Other compounds may be activated under hypoxic conditions, which are also found in certain types of cancer cells. Such compounds may not be activated in healthy cells, which may reduce toxicity associated with many known anti-cancer agents.

1. DEFINITIONS

The terminology used herein is for the purpose of describing particular embodiments only and is not intended to be limiting. As used in the specification and the appended claims, the singular forms "a," "and" and "the" include plural references unless the context clearly dictates otherwise.

Section headings as used in this section and the entire disclosure herein are not intended to be limiting.

For the recitation of numeric ranges herein, each intervening number with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

As used herein, the term "about" is used synonymously with the term "approximately." Illustratively, the use of the term "about" indicates that values slightly outside the cited values, namely, plus or minus 10%. Such values are thus encompassed by the scope of the claims reciting the terms "about" and "approximately."

"Administration" or "administering," as used herein, refers to providing, contacting, and/or delivery of a compound or compounds by any appropriate route to achieve the desired effect. Administration may include, but is not limited to, oral, sublingual, parenteral (e.g., intravenous, subcutaneous, intracutaneous, intramuscular, intraarticular, intraarterial, intrasynovial, intrasternal, intrathecal, intralesional or intracranial injection), transdermal, topical, buccal, rectal, vaginal, nasal, ophthalmic, via inhalation, and implants.

"Contacting," as used herein as in "contacting a cell," refers to contacting a cell directly or indirectly in vitro, ex vivo, or in vivo (i.e. within a subject, such as a mammal, including humans, mice, rats, rabbits, cats, and dogs). Contacting a cell, which also includes "reacting" a cell, can occur as a result of administration to a subject. Contacting encompasses administration to a cell, tissue, mammal, subject, patient, or human. Further, contacting a cell includes adding an agent to a cell culture. Other suitable methods may include introducing or administering an agent to a cell, tissue, mammal, subject, or patient using appropriate procedures and routes of administration as defined herein.

"Effective amount," as used herein, refers to a dosage of the compounds or compositions effective for eliciting a desired effect. This term as used herein may also refer to an amount effective at bringing about a desired in vivo effect in an animal, mammal, or human, such as reducing proliferation of a cancer cell.

"Electron withdrawing group," as used herein, refers to a group covalently linked to a carbon atom that forms a polarized bond, similar to a good leaving group, and can include groups such as halogens, nitro, cyano, carbonyl, and boronic acid or ester groups.

A "hydroxy protecting group," as used herein, is well known in the art and includes those described in detail in Protecting Groups in Organic Synthesis, T. W. Greene and P. G. M. Wuts, 3rd edition, John Wiley & Sons, 1999, the entirety of which is incorporated herein by reference. Exemplary hydroxy protecting groups may include, but are not limited to, acetyl (Ac), benzyl (Bn), benzoyl (Bz), ethers (e.g., methoxymethyl ether (MOM) and β-methoxyethoxymethyl ether (MEM)), silyl groups (e.g., trimethylsilyl (TMS), triethylsilyl (TES), triisopropylsilyl (TIPS), tri-iso-propylsilyloxymethyl (TOM) and t-butyldimethylsilyl (TBDMS)), trityl groups (e.g., dimethoxytrityl (DMT) and methoxytrityl (MMT)), and the like.

"Reducing proliferation of a cell," as used herein, refers to reducing, inhibiting, or preventing the survival, growth, or differentiation of a cell, including killing a cell. A cell can be derived from any organism or tissue type and includes, for example, a cancer cell (e.g., neoplastic cells, tumor cells, and the like).

As used herein, the term "subject" is intended to include human and non-human animals. Exemplary human subjects include a human patient having a disorder, e.g., cancer, or a normal subject. The term "non-human animals" includes all vertebrates, e.g., non-mammals (such as chickens, amphibians, reptiles) and mammals, such as non-human primates, domesticated and/or agriculturally useful animals (such as sheep, dogs, cats, cows, pigs, etc.), and rodents (such as mice, rats, hamsters, guinea pigs, etc.).

As used herein, the term "treat" or "treating" a subject having a disorder refers to administering a regimen to the subject, e.g., the administration of a compound or a composition comprising a compound, such that at least one symptom of the disorder is cured, healed, alleviated, relieved, altered, remedied, ameliorated, or improved. Treating includes administering an amount effective to alleviate, relieve, alter, remedy, ameliorate, improve or affect the disorder or the symptoms of the disorder. The treatment may inhibit deterioration or worsening of a symptom of a disorder.

Definitions of specific functional groups and chemical terms are described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5th Edition, John Wiley & Sons, Inc., New York, 2001; Larock, Comprehensive Organic Transformations, VCH Publishers, Inc., New York, 1989; Carruthers, Some Modern Methods of Organic Synthesis, 3rd Edition, Cambridge University Press, Cambridge, 1987; the entire contents of each of which are incorporated herein by reference.

The term "acyl" refers to an alkylcarbonyl, cycloalkylcarbonyl, heterocyclylcarbonyl, arylcarbonyl or heteroarylcarbonyl substituent, any of which may be further substituted (e.g., with one or more substituents).

The term "alkyl" refers to a straight or branched hydrocarbon chain, containing the indicated number of carbon atoms. For example, $C_1$-$C_{12}$ alkyl indicates that the alkyl group may have from 1 to 12 (inclusive) carbon atoms. The term "alkylene" refers to a divalent alkyl, e.g., —$CH_2$—, —$CH_2CH_2$—, —$CH_2CH_2CH_2$— or —$CH_2CH(CH_3)CH_2$—. An alkyl or alkylene may be optionally substituted.

The term "alkenyl" refers to a straight or branched hydrocarbon chain having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent. The term "alkenylene" refers to a divalent alkenyl, e.g., —CH=CH—, —CH=$CH_2CH_2$— or —CH=C=CH—. An alkenyl or alkenylene may be optionally substituted.

The term "alkynyl" refers to a straight or branched hydrocarbon chain having one or more triple bonds. Examples of alkynyl groups include, but are not limited to, ethynyl, propargyl, and 3-hexynyl. One of the triple bond carbons may optionally be the point of attachment of the alkynyl substituent. The term "alkynylene" refers to a divalent alkynyl, e.g., —C≡C— or —C≡C—$CH_2$—. An alkynyl or alkynylene may be optionally substituted.

The term "amino" refers to a group of the formula —$NR^1R^2$, wherein $R^1$ and $R^2$ are each independently selected from, for example, hydrogen, alkyl, cycloalkyl, heterocyclyl, aryl and heteroaryl, or $R^1$ and $R^2$, together with the nitrogen to which they are attached, may form a ring structure. Examples of amino groups include, but are not limited to, —$NH_2$, alkylamino groups such as —$NHCH_3$, —$NHCH_2CH_3$ and —$NHCH(CH_3)_2$, dialkylamino groups such as —$N(CH_3)_2$ and —$N(CH_2CH_3)_2$, and arylamino groups such as —NHPh. Examples of cyclic amino groups include, but are not limited to, aziridinyl, azetidinyl, pyrrolidinyl, piperidino, piperazinyl, perhydrodiazepinyl, morpholino, and thiomorpholino. The groups $R^1$ and $R^2$ may be optionally substituted.

The term "aryl" refers to an aromatic monocyclic, bicyclic, or tricyclic hydrocarbon ring system, wherein any ring atom capable of substitution can be substituted (e.g., with one or more substituents). Examples of aryl moieties include, but are not limited to, phenyl, naphthyl, and anthracenyl.

The term "arylalkyl" refers to an alkyl moiety in which an alkyl hydrogen atom is replaced with an aryl group. Arylalkyl includes groups in which more than one hydrogen atom has been replaced with an aryl group. Examples of arylalkyl groups include benzyl, 2-phenylethyl, 3-phenylpropyl, 9-fluorenyl, benzhydryl, and trityl groups.

The term "cycloalkyl" as used herein refers to nonaromatic, saturated or partially unsaturated cyclic, bicyclic, tricyclic or polycyclic hydrocarbon groups having 3 to 12 carbons. Any ring atom can be substituted (e.g., with one or more substituents). Cycloalkyl groups can contain fused rings. Fused rings are rings that share one or more common carbon atoms. Examples of cycloalkyl groups include, but are not limited to, cyclopropyl, cyclobutyl, cyclopentyl, cyclohexyl, cyclohexenyl, cyclohexadienyl, methylcyclohexyl, adamantyl, norbornyl and norbornenyl.

The term "halo" or "halogen" as used herein refers to any radical of fluorine, chlorine, bromine or iodine.

The term "haloalkyl" as used herein refers to an alkyl in which one or more hydrogen atoms are replaced with a halogen, and includes alkyl moieties in which all hydrogens have been replaced with halogens (e.g., perfluoroalkyl such as $CF_3$). Haloalkyl groups may contain an indicated number of carbon atoms. For example, $C_1$-$C_4$ haloalkyl indicates that the haloalkyl group may have 1, 2, 3 or 4 carbon atoms.

The term "heteroaryl" as used herein refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms independently selected from O, N, S, P and Si (e.g., carbon atoms and 1-3, 1-6, or 1-9 heteroatoms independently selected from O, N, S, P and Si if monocyclic, bicyclic, or tricyclic, respectively). Any ring atom can be substituted (e.g., with one or more substituents). Heteroaryl groups can contain fused rings, which are rings that share one or more common atoms. Examples of heteroaryl groups include, but are not limited to, radicals of pyridine, pyrimidine, pyrazine, pyridazine, pyrrole, imidazole, pyrazole, oxazole, isoxazole, furan, thiazole, isothiazole, thiophene, quinoline, isoquinoline, quinoxaline, quinazoline, cinnoline, indole, isoindole, indolizine, indazole, benzimidazole, phthalazine, pteridine, carbazole, carboline, phenanthridine, acridine, phenanthroline, phenazine, naphthyridines and purines.

The term "heterocyclyl" as used herein refers to a nonaromatic, saturated or partially unsaturated 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, S, Si and P (e.g., carbon atoms and 1-3, 1-6, or 1-9 heteroatoms of O, N, S, Si and P if monocyclic, bicyclic, or tricyclic, respectively). Any ring atom can be substituted (e.g., with one or more substituents). Heterocyclyl groups can contain fused rings, which are rings that share one or more common atoms. Examples of heterocyclyl groups include, but are not limited to, radicals of tetrahydrofuran, tetrahydrothiophene, tetrahydropyran, piperidine, piperazine, morpholine, pyrroline, pyrimidine, pyrrolidine, indoline, tetrahydropyridine, dihydropyran, thianthrene, pyran, benzopyran, xanthene, phenoxathiin, phenothiazine, furazan, lactones, lactams such as azetidinones and pyrrolidinones, sultams, sultones, and the like.

The term "hydroxy" refers to an —OH radical. The term "alkoxy" refers to an —O-alkyl radical. The term "aryloxy" refers to an —O-aryl radical.

The term "oxo" refers to an oxygen atom, which forms a carbonyl when attached to carbon, an N-oxide when attached to nitrogen, and a sulfoxide or sulfone when attached to sulfur.

The term "mercapto" or "thiol" refers to an —SH radical. The term "thioalkoxy" or "thioether" refers to an —S-alkyl radical. The term "thioaryloxy" refers to an —S-aryl radical.

The term "substituents" refers to a group "substituted" on an alkyl, alkenyl, alkynyl, cycloalkyl, cycloalkylalkyl, heterocyclyl, heterocyclylalkyl, aryl, arylalkyl, heteroaryl or heteroarylalkyl group at any atom of that group. Any atom can be substituted. Suitable substituents include, without limitation: acyl, acylamido, acyloxy, alkoxy, alkyl, alkenyl, alkynyl, amido, amino, carboxy, cyano, ester, halo, hydroxy, imino, nitro, oxo (e.g., C=O), phosphonate, sulfinyl, sulfonyl, sulfonate, sulfonamino, sulfonamido, thioamido, thiol, thioxo (e.g., C=S), and ureido. In embodiments, substituents on a group are independently any one single, or any combination of the aforementioned substituents. In embodiments, a substituent may itself be substituted with any one of the above substituents.

The above substituents may be abbreviated herein, for example, the abbreviations Me, Et, Ph, Ac and Ts represent methyl, ethyl, phenyl, acetyl and tosyl (p-toluenesulfonyl), respectively. A more comprehensive list of the abbreviations used by organic chemists of ordinary skill in the art appears in the first issue of each volume of the Journal of Organic Chemistry; this list is typically presented in a table entitled Standard List of Abbreviations. The abbreviations contained in said list, and all abbreviations used by organic chemists of ordinary skill in the art, are hereby incorporated by reference.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

Where substituent groups are specified by their conventional chemical formulae, written from left to right, they optionally encompass substituents resulting from writing the structure from right to left, e.g., —$CH_2O$— optionally also recites —$OCH_2$—.

In accordance with a convention used in the art, the group:

is used in structural formulas herein to depict the bond that is the point of attachment of the moiety or substituent to the core or backbone structure.

2. COMPOUNDS

Compounds may have the following formula (I):

wherein:

each $R^1$ is independently —$B(XR')_2$, wherein each X is independently selected from O and S, and each R' is independently selected from hydrogen and alkyl, or two R' are taken together to form an optionally substituted 5- to 8-membered ring;

each $R^2$ is independently selected from optionally substituted alkyl, alkoxy, amino, halo, and —$CH_2$—$N(R^a)_3$,⊕;

each $R^3$ is independently selected from:

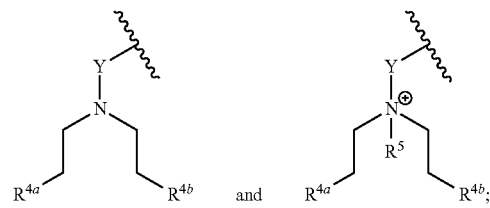

each $R^{4a}$ and $R^{4b}$ is independently selected from halo and —$OSO_2R^a$;

each Y is independently a bond or —CH$_2$—;

each R$^5$ is independently C$_1$-C$_4$ alkyl;

n is 0, 1 or 2;

p is 1 or 2;

each R$^a$ is independently selected from optionally substituted alkyl;

wherein if the compound of formula (I) bears a positive charge, it further comprises at least one counterion Z$\ominus$.

In embodiments, compounds of formula (I) may have the following structures:

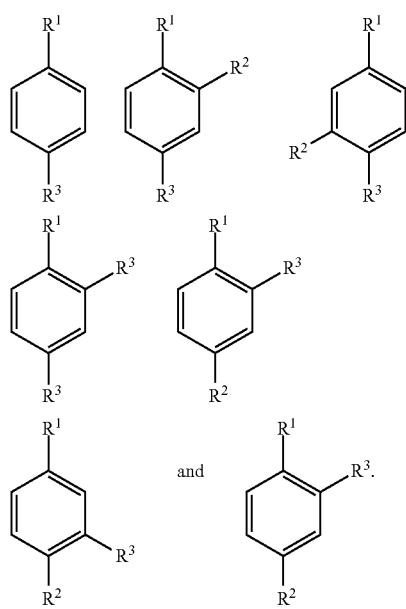

In embodiments, R$^1$ may be selected from the group consisting of:

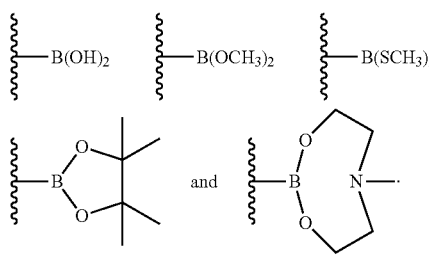

For example, in embodiments R$^1$ is selected from the group consisting of:

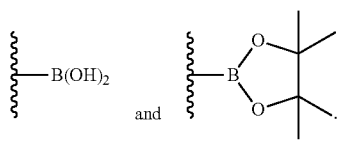

In some embodiments, n is 0. In some embodiments, n is 1. In some embodiments, R$^2$ is methyl.

In some embodiments, R$^3$ is selected from the group consisting of:

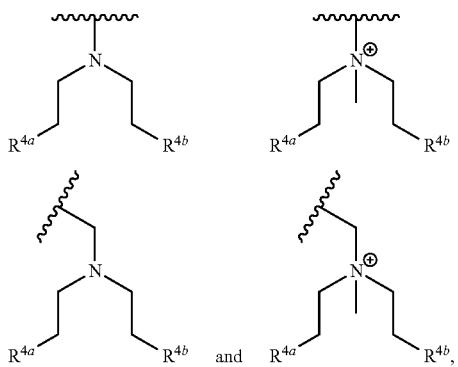

wherein each R$^{4a}$ and R$^{4b}$ is independently selected from chloro, bromo, and —OSO$_2$CH$_3$.

For example, compounds of formula (I) may be selected from the group consisting of:

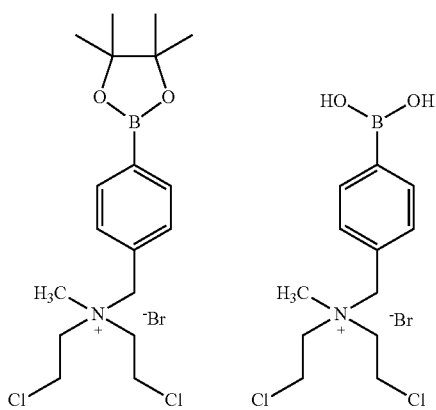

-continued

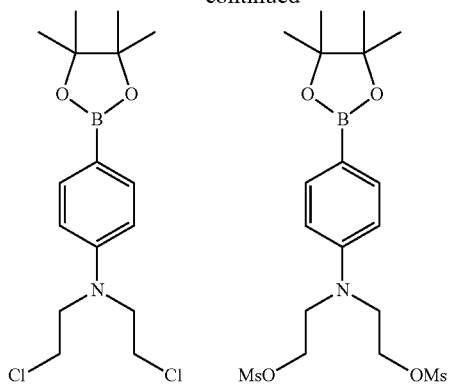

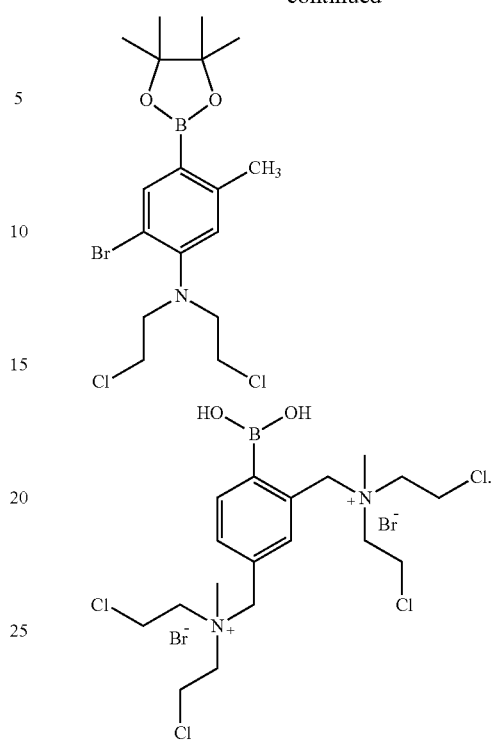

Compounds may have the following formula (Ia):

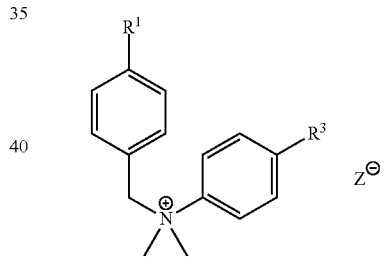

(Ia)

wherein:

R$^1$ is —B(XR')$_2$, wherein each X is independently selected from O and S, and each R' is independently selected from hydrogen and alkyl, or two R' are taken together to form an optionally substituted 5- to 8-membered ring;

R$^3$ is:

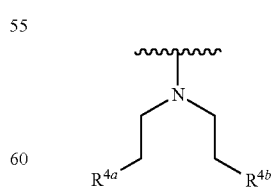

wherein each R$^{4a}$ and R$^{4b}$ is independently selected from halo and —OSO$_2$R$^a$; and each R$^a$ is independently selected from optionally substituted alkyl.

In embodiments, R¹ is selected from the group consisting of:

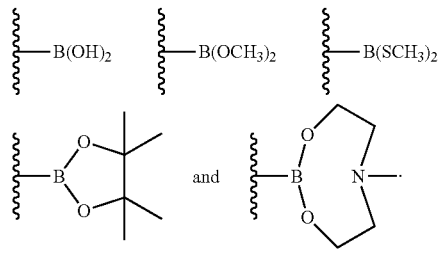

For example, in embodiments R¹ is selected from the group consisting of:

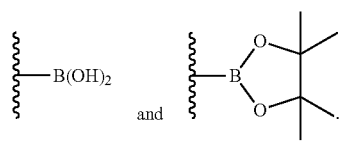

In embodiments each $R^{4a}$ and $R^{4b}$ is independently selected from chloro, bromo, and —OSO₂CH₃.

Compounds may have the following formula (II):

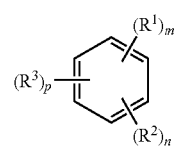

(II)

wherein:
each R¹ is independently —B(XR')₂, wherein each X is independently selected from O and S, and each R' is independently selected from hydrogen and alkyl, or two R' are taken together to form an optionally substituted 5- to 8-membered ring;
each R² is independently selected from optionally substituted alkyl, alkoxy, amino, halo and nitro;
each R³ is independently selected from:

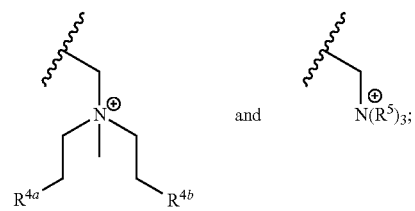

each $R^{4a}$ and $R^{4b}$ is independently selected from halo and —OSO₂Rᵇ;
each R⁵ is independently optionally substituted alkyl;
m is 1 or 2;
n is 0, 1 or 2;
p is 2; and
wherein the compound further comprises at least one counterion Z⊖.

In embodiments, compounds of formula (II) may have the following structures:

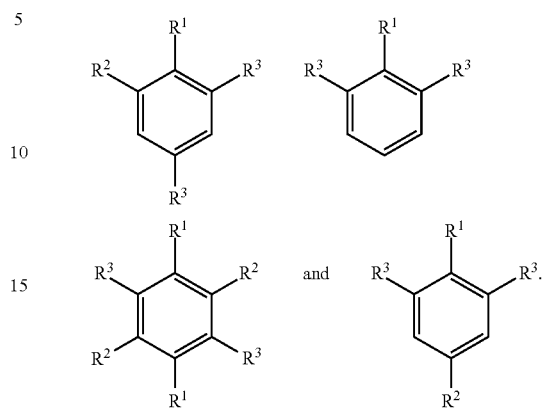

In embodiments, R¹ is selected from the group consisting of:

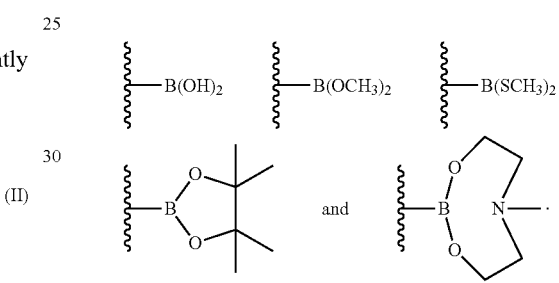

For example, in embodiments R¹ is:

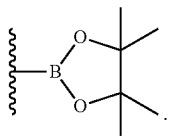

In embodiments, each R² is independently selected from the group consisting of alkoxy (e.g., methoxy, ethoxy, propoxy), halo (e.g., fluoro), nitro, —NH₂, alkylamino (e.g., —NHCH₃, —NHCH₂CH₃) and dialkylamino (e.g., dimethylamino, diethylamino).

In embodiments, R³ is selected from the group consisting of:

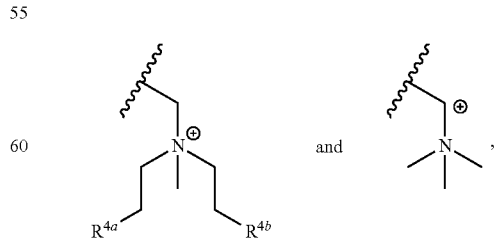

wherein each $R^{4a}$ and $R^{4b}$ is independently selected from chloro, bromo, and —OSO₂CH₃.

Compounds may have the following formula (IIa):

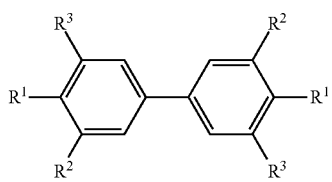

each $R^1$ is independently —B(XR')$_2$, wherein each X is independently selected from O and S, and each R' is independently selected from hydrogen and alkyl, or two R' are taken together to form an optionally substituted 5- to 8-membered ring;
each $R^2$ is independently selected from hydrogen, optionally substituted alkyl, alkoxy, amino, halo and nitro;
each $R^3$ is independently selected from:

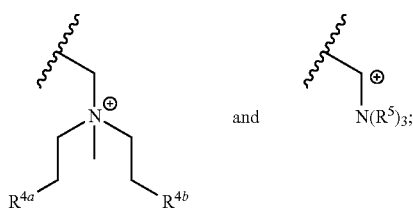

each $R^{4a}$ and $R^{4b}$ is independently selected from halo and —OSO$_2$R$^b$;
each $R^5$ is independently optionally substituted alkyl;
m is 1 or 2;
n is 0, 1 or 2;
p is 2; and
wherein the compound further comprises at least one counterion Z⊖.
In embodiments, each $R^1$ is selected from the group consisting of:

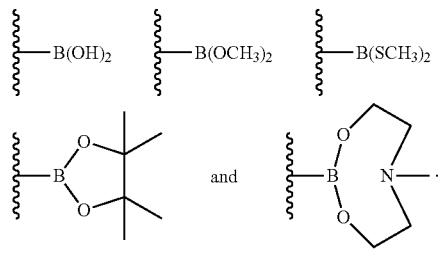

For example, in embodiments each $R^1$ is:

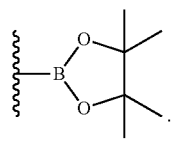

In embodiments, each $R^2$ is independently selected from the group consisting of alkoxy (e.g., methoxy, ethoxy, propoxy), halo (e.g., fluoro), nitro, —NH$_2$, alkylamino (e.g., —NHCH$_3$, —NHCH$_2$CH$_3$) and dialkylamino (e.g., dimethylamino, diethylamino).

In embodiments, each $R^3$ is independently selected from the group consisting of:

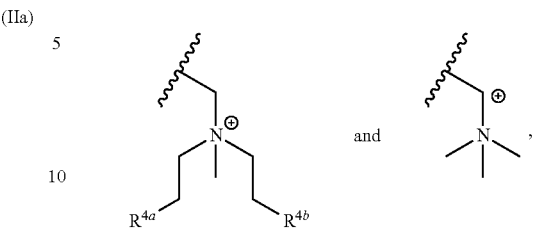

wherein each $R^{4a}$ and $R^{4b}$ is independently selected from chloro, bromo, and —OSO$_2$CH$_3$.
Compounds may have the following formula (III):

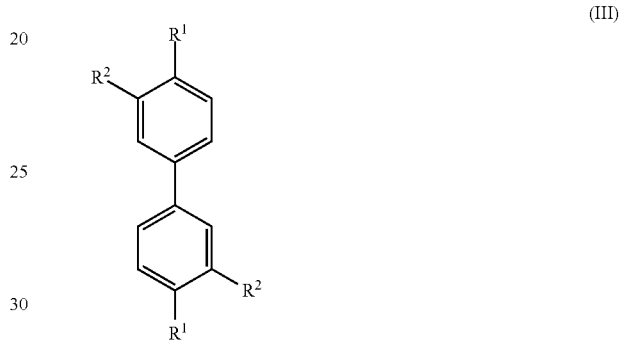

wherein:
each $R^1$ is independently selected from selected from the group consisting of:

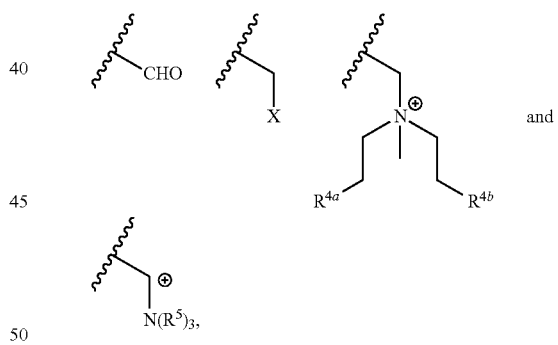

wherein at least one $R^1$ is other than —CHO;
each $R^2$ is independently selected from an electron-withdrawing group;
each X is independently halo;
each $R^{4a}$ and $R^{4b}$ is independently selected from halo and —OSO$_2$R$^b$; and
each $R^5$ is independently selected from optionally substituted alkyl;
wherein if the compound of formula (III) bears a positive charge, it further comprises at least one counterion Z⊖.
In embodiments, each $R^1$ is —CH$_2$X. In embodiments, each X is bromo.
In embodiments, each $R^1$ is —CH$_2$—N(R$^a$)$_3$⊕. In embodiments, each $R^a$ is methyl.
In embodiments, one $R^1$ is —CHO and the other is —CH$_2$—N(R$^a$)$_3$⊕.

In embodiments, each R[1] is:

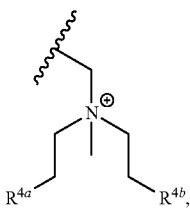

wherein each R[4a] and R[4b] is independently selected from chloro, bromo, and —OSO$_2$CH$_3$.

In embodiments, each R[2] is independently selected from nitro, cyano and carboxy.

In embodiments, the compound is selected from the group consisting of:

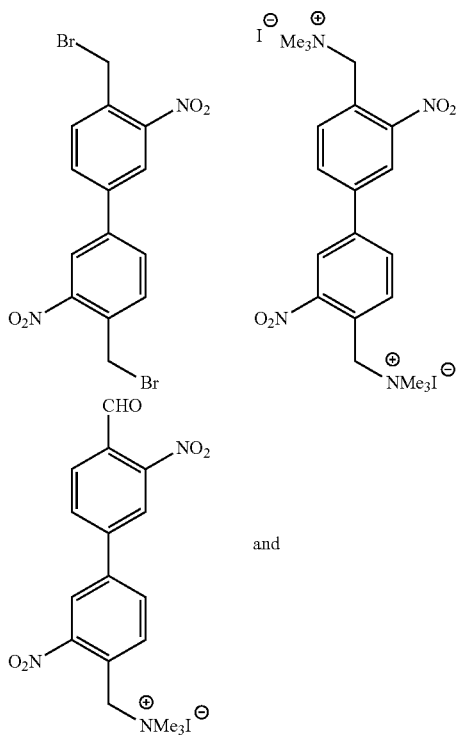

and

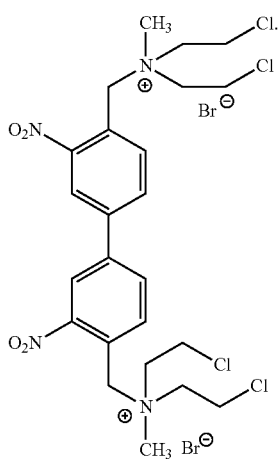

Compounds may have the following formula (IIIa):

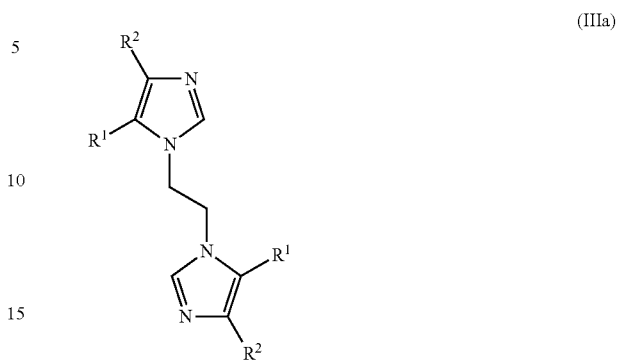

wherein:
each R[1] is independently selected from selected from the group consisting of:

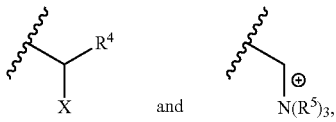

each R[2] is independently selected from an electron-withdrawing group;
each X is independently halo;
each R[4] is independently selected from the group consisting of —H and —COO(alkyl), and
each R[5] is independently selected from optionally substituted alkyl;
wherein if the compound of formula (III) bears a positive charge, it further comprises at least one counterion Z⊖.

In embodiments, each R[1] is —CH$_2$X. In embodiments, each X is chloro.

In embodiments, each R[1] is —CH(X)—R[4]. In embodiments, each X is chloro. In embodiments, each R[4] is —C(O)OC(CH$_3$)$_3$.

In embodiments, each R[1] is —CH$_2$—N(R$^a$)$_3$⊕. In embodiments, each R$^a$ is methyl.

In embodiments, each R[2] is independently selected from the group consisting of nitro, cyano and carboxy. In embodiments, each R[2] is nitro.

In embodiments, the compound is selected from the group consisting of:

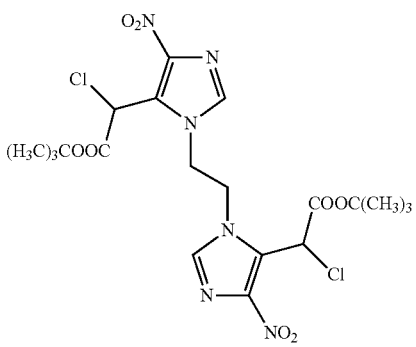

-continued

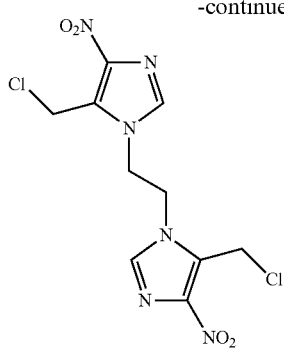

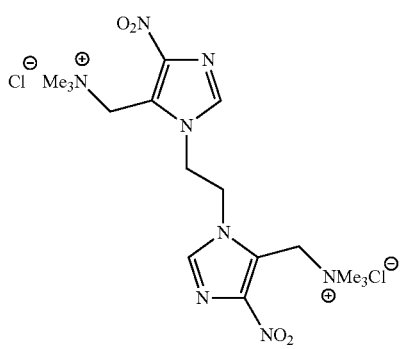
and
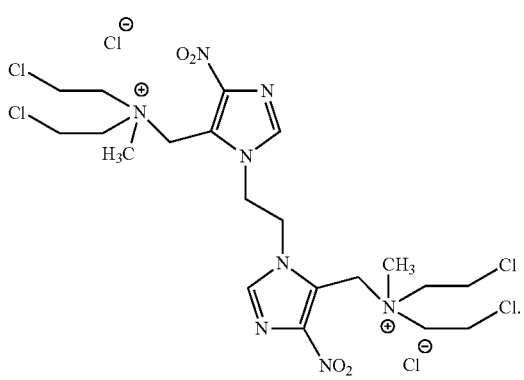

Compounds may have the following formula (IV):

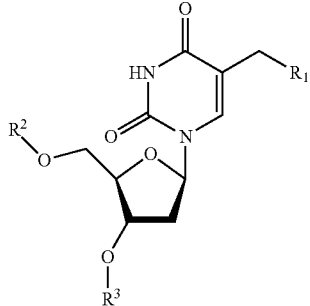
(IV)

wherein:
R¹ is selected from the group consisting of:

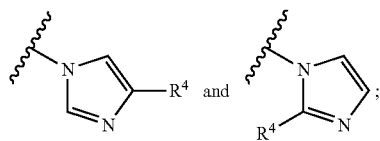

$R^2$ is selected from the group consisting of —H and a hydroxy protecting group;
$R^3$ is selected from the group consisting of —H and —P(N(CH(CH$_3$)$_2$)$_2$)(OCH$_2$CH$_2$CN); and
each $R^4$ is independently an electron withdrawing group.

In embodiments, $R^2$ is —H.
In embodiments, $R^2$ is a hydroxy protecting group. In embodiments, $R^2$ is a 4,4'-dimethoxytrityl group.
In embodiments, $R^3$ is —H.
In embodiments, $R^3$ is —P(N(CH(CH$_3$)$_2$)$_2$)(OCH$_2$CH$_2$CN).
In embodiments, each $R^4$ is independently selected from the group consisting of nitro, cyano and carboxy. In embodiments, each $R^4$ is nitro.

In embodiments, the compound is selected from the group consisting of:

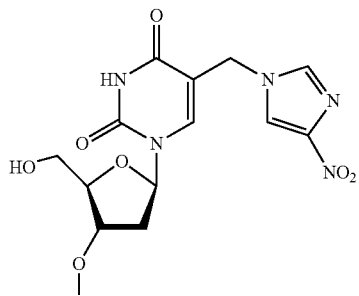

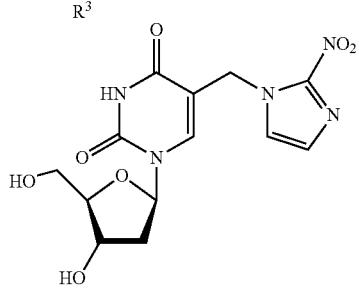

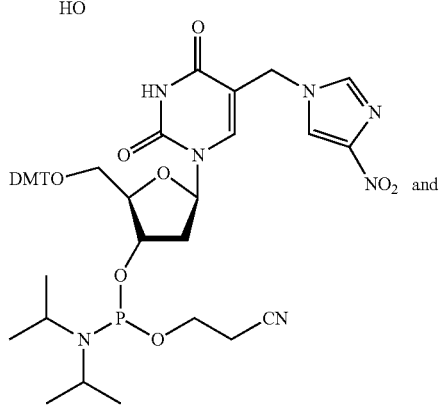
and

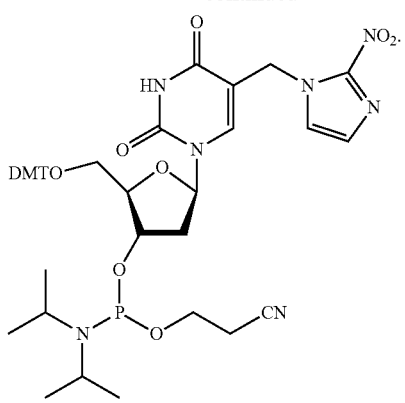

Compounds may have the one of the following formulae (Va)-(Vf):

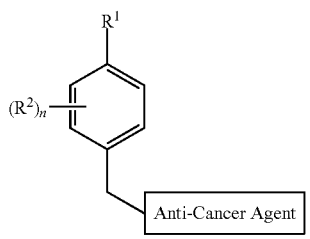
(Va)

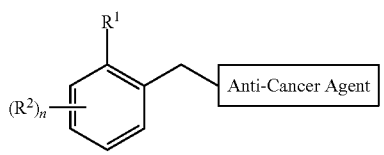
(Vb)

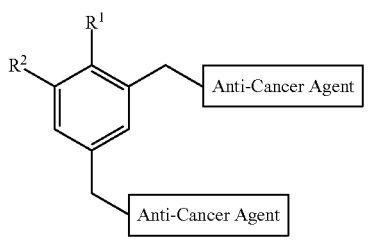
(Vc)

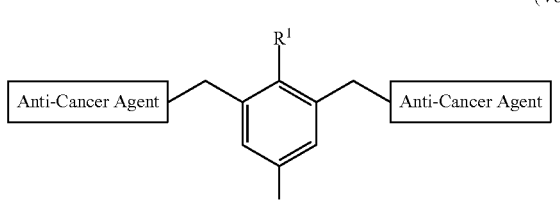
(Vd)

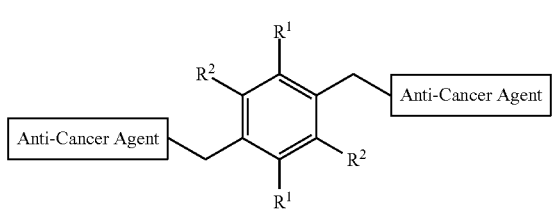
(Ve)

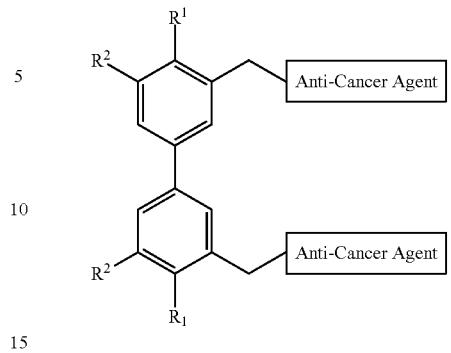
(Vf)

wherein:
each $R^1$ is independently —$B(XR')_2$, wherein each X is independently selected from O and S, and each R' is independently selected from hydrogen and alkyl, or two R' are taken together to form an optionally substituted 5- to 8-membered ring;
each $R^2$ is independently selected from optionally substituted alkyl, alkoxy, amino, halo, and —$CH_2$—$N(R^a)_3\oplus$; and
n is 0, 1 or 2.

In embodiments, $R^1$ is selected from the group consisting of:

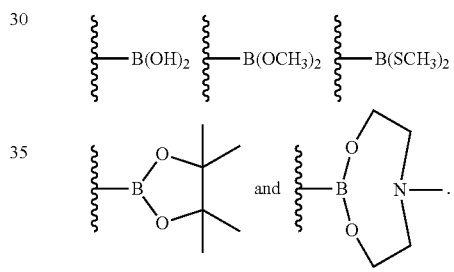

For example, in embodiments $R^1$ is:

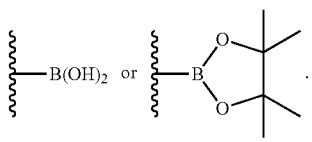

In some embodiments, the anti-cancer agent is an anti-cancer agent described herein. In some embodiments, the anti-cancer agent is linked to the remainder of the compound of formula (V) via a functional group such as a hydroxyl group, an amino group or a carboxy group. In some embodiments, the anti-cancer agent is modified with a functional group such that it can be linked to the remainder of the compound of formula (V).

It will be understood by the skilled artisan that compound having a boronic acid group (i.e. —$B(OH)_2$) may be in equilibrium with the corresponding boronic anhydride (also known as a boroxine). Accordingly, when compounds of the formulae herein have boronic acid groups, it is understood that the formulae are also intended to cover the boroxine forms.

Compounds of formula (I), (Ia), (II), (IIa), (III), (IIIa), (IV), (Va), (Vb), (Vc), (Vd), (Ve) and (Vf) include compounds that differ only in the presence of one or more isotopically enriched atoms. For example, compounds may have the present structures except for the replacement of hydrogen by deuterium or tritium, or the replacement of a carbon by a $^{13}$C- or $^{14}$C-enriched carbon.

A compound of formula (I), (Ia), (II), (IIa), (III), (IIIa), (IV), (Va), (Vb), (Vc), (Vd), (Ve) or (Vf) can be in the form of a salt, e.g., a pharmaceutically acceptable salt. The term "pharmaceutically acceptable salt" includes salts of the active compounds that are prepared with relatively nontoxic acids or bases, depending on the particular substituents found on the compounds. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulfuric acid, methanesulfonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts, alkaline earth metal salts, e.g. calcium or magnesium salts; and salts formed with suitable organic ligands, e.g. quaternary ammonium salts.

Neutral forms of the compounds may be regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of this disclosure.

Compounds of formula (I), (Ia), (II), (IIa), (III), (IIIa), (IV), (Va), (Vb), (Vc), (Vd), (Ve) and (Vf) can be, for example, an enantiomerically enriched isomer of a stereoisomer described herein. Enantiomer, as used herein, refers to either of a pair of chemical compounds whose molecular structures have a mirror-image relationship to each other. For example, a compound may have an enantiomeric excess of at least about 10%, 15%, 20%, 25%, 30%, 35%, 40%, 45%, 50%, 55%, 60%, 65%, 70%, 75%, 80%, 85%, 90%, 95%, 96%, 97%, 98%, or 99%.

In some embodiments, a preparation of a compound of formula (I), (Ia), (II), (IIa), (III), (IIIa), (IV), (Va), (Vb), (Vc), (Vd), (Ve) or (Vf) may be enriched for isomers (subject isomers) which are diastereomers of the compound. Diastereomer, as used herein, refers to a stereoisomer of a compound having two or more chiral centers that is not a mirror image of another stereoisomer of the same compound. For example, the compound may have a purity corresponding to a compound having a selected diastereomer of at least about 60%, 65%, 70%, 75%, 80%, 85%, 90%, 95%, 96%, 97%, 98%, or 99%.

When no specific indication is made of the configuration at a given stereocenter in a compound, any one of the configurations or a mixture of configurations is intended.

Compounds may be prepared in racemic form or as individual enantiomers or diastereomers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. The enantiomers also may be obtained from kinetic resolution of the racemate of corresponding esters using lipase enzymes.

A compound of formula (I), (Ia), (II), (IIa), (III), (IIIa), (IV), (Va), (Vb), (Vc), (Vd), (Ve) or (Vf) can also be modified by appending appropriate functionalities to enhance selective biological properties. Such modifications are known in the art and include those that increase biological penetration into a given biological system (e.g., blood, lymphatic system, central nervous system), increase oral availability, increase solubility to allow administration by injection, alter metabolism, and/or alter rate of excretion. Examples of these modifications include, but are not limited to, esterification with polyethylene glycols, derivatization with pivolates or fatty acid substituents, conversion to carbamates, hydroxylation of aromatic rings, and heteroatom substitution in aromatic rings.

Preparation of Compounds

Compounds described herein may be prepared according to a variety of methods. Representative syntheses of exemplary compounds of formula (I) are illustrated in Schemes 1-9.

Scheme 1. Exemplary Synthesis

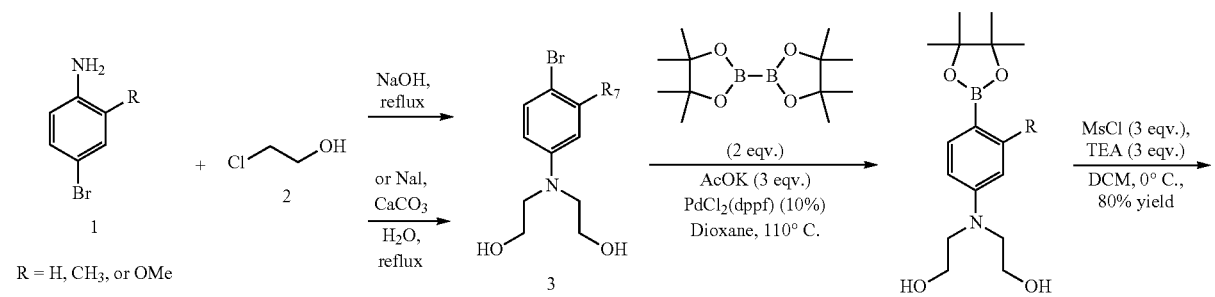

-continued
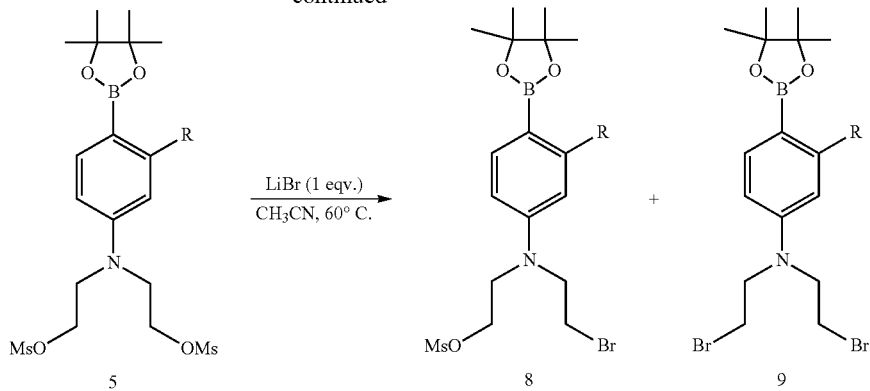
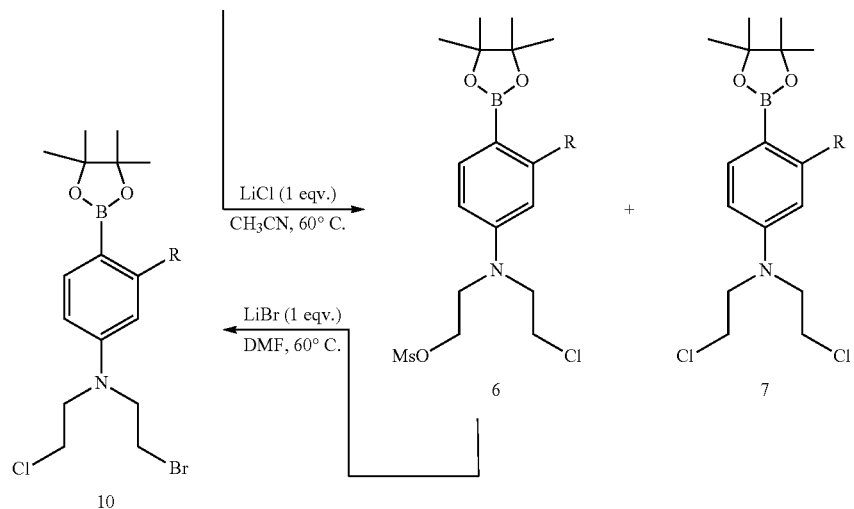
R = H, CH₃, or OMe

Compounds of general formula Ic (R=OMe) have previously been synthesized (Zysman-Colman, Eli et al. *Canadian Journal of Chemistry*, 2009, 87, 440-447). Compound 1 can be converted into 2 as illustrated in Scheme 1 (Lin, Song-Wen et al. *Bioorganic & Medicinal Chemistry Letters*, 2011, 21, 940-943). The boronation of 3 can be catalyzed by PdCl$_2$ (dppf) using KOAc as base to form compound 4 (Wang, Lianhui et al. *Advanced Synthesis & Catalysis*, 2010, 352, 2002-2010). 4 can be converted into 5 by treatment with methanesulfonyl chloride (Ferlin, M. G. et al. *Bioorganic Medicinal Chemistry*, 2004, 12, 771-777). Compounds 6-9 can be obtained by treating 5 with lithium bromide or lithium chloride respectively and 6 can converted to 10.

Scheme 2. Exemplary Synthesis

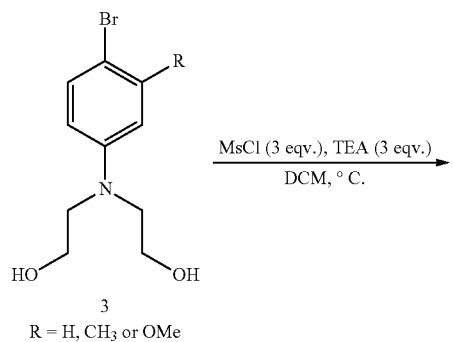

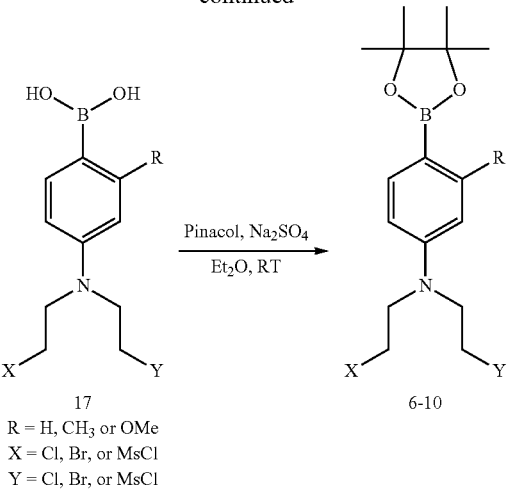

17
R = H, CH$_3$ or OMe
X = Cl, Br, or MsCl
Y = Cl, Br, or MsCl

Compounds 3 can be converted to compounds 11-16 by the same procedures as 6-10. Boron acid 17 can be obtained by treatment of 11-16 with butyllithium followed by boron ester (White, James R. et al. *Tetrahedron Letters*, 2010, 51, 3913-3917). 6-10 can also be synthesized by the reaction of 17 and pinacol (White, James R. et al. *Tetrahedron Letters*, 2010, 51, 3913-3917).

Scheme 3. Exemplary Synthesis

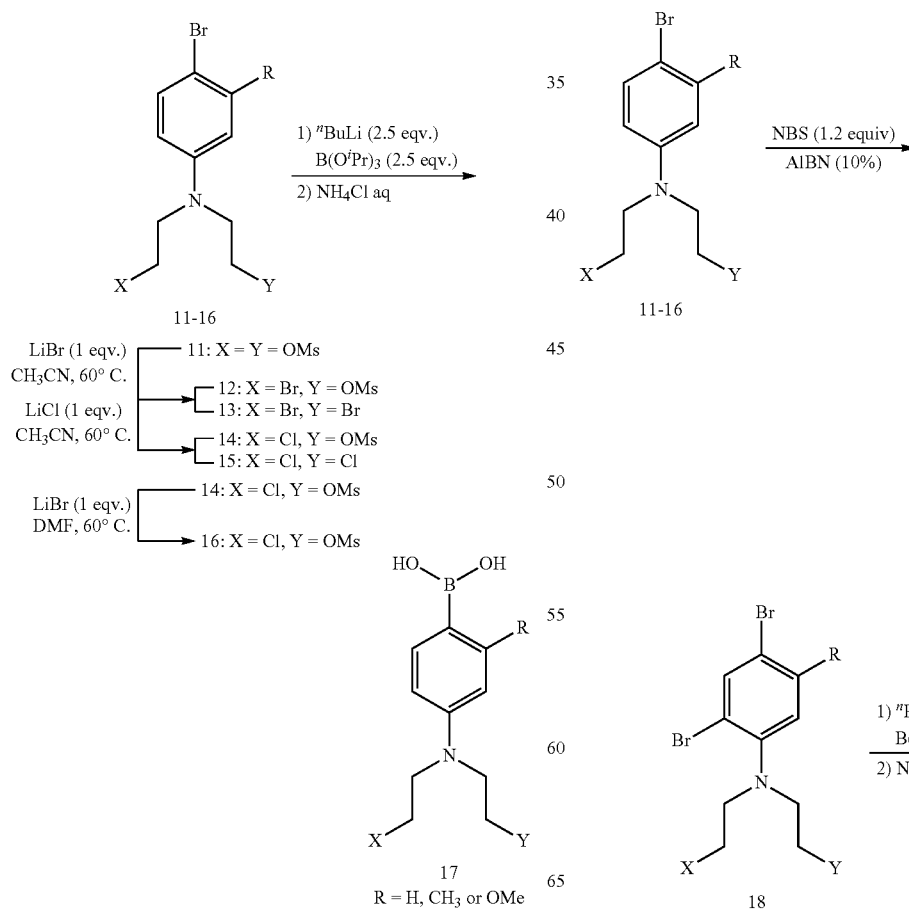

33
-continued

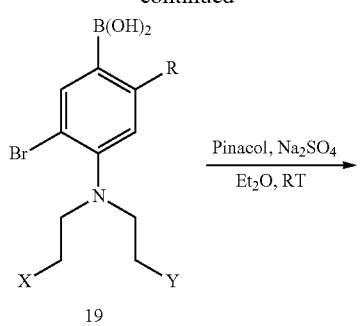

19

R = H, CH₃ or OMe
X = Cl, Br or OMs
Y = Cl, Br or OMS

Bromination of 11-16 can produce 18 by reacting with NBS using AIBN as the catalyst. Boronic acid 19 and boronic ester 20 can be obtained with the procedures as illustrated in Scheme 3, Scheme 4. Exemplary Synthesis

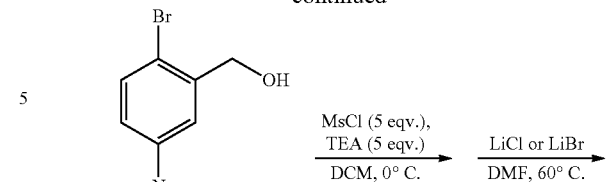

34
-continued

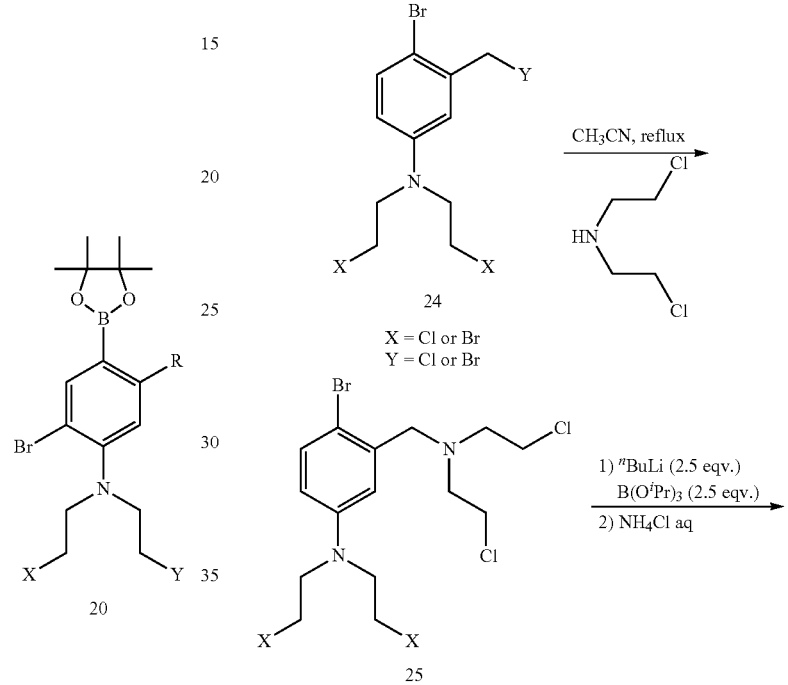

X = Cl or Br
Y = Cl or Br

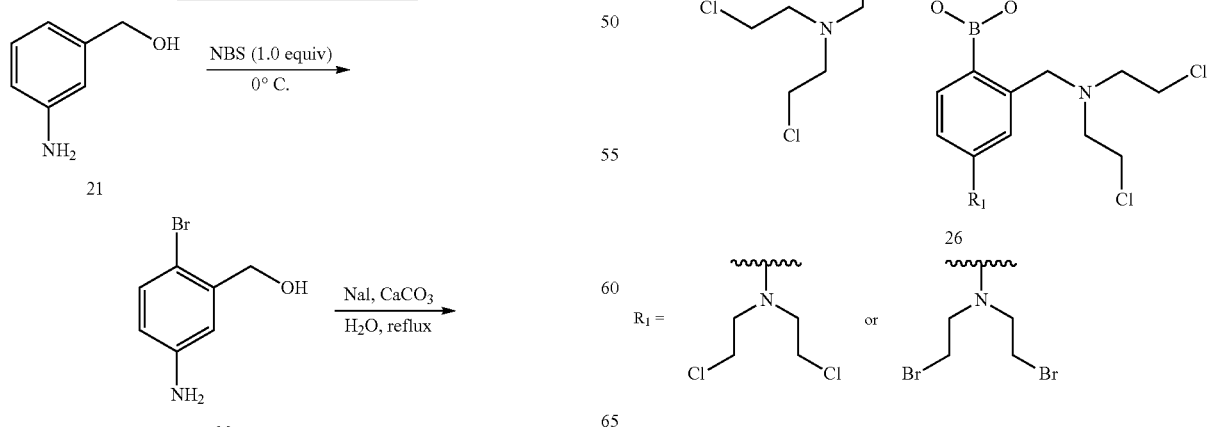

Compound 21 can be converted into 23 as illustrated in Scheme 4. 23 can be converted into 24 by treatment with methanesulfonyl chloride followed by lithium bromide or lithium chloride respectively. 24 can be converted to 25 by treated with bis(2-chloroethyl)amine. 26 can be obtained by the boronation of 25 using butyllithium as base (Kevin R. Flower et al. *Dalton Trans.* 2011, 40, 11696-11697).

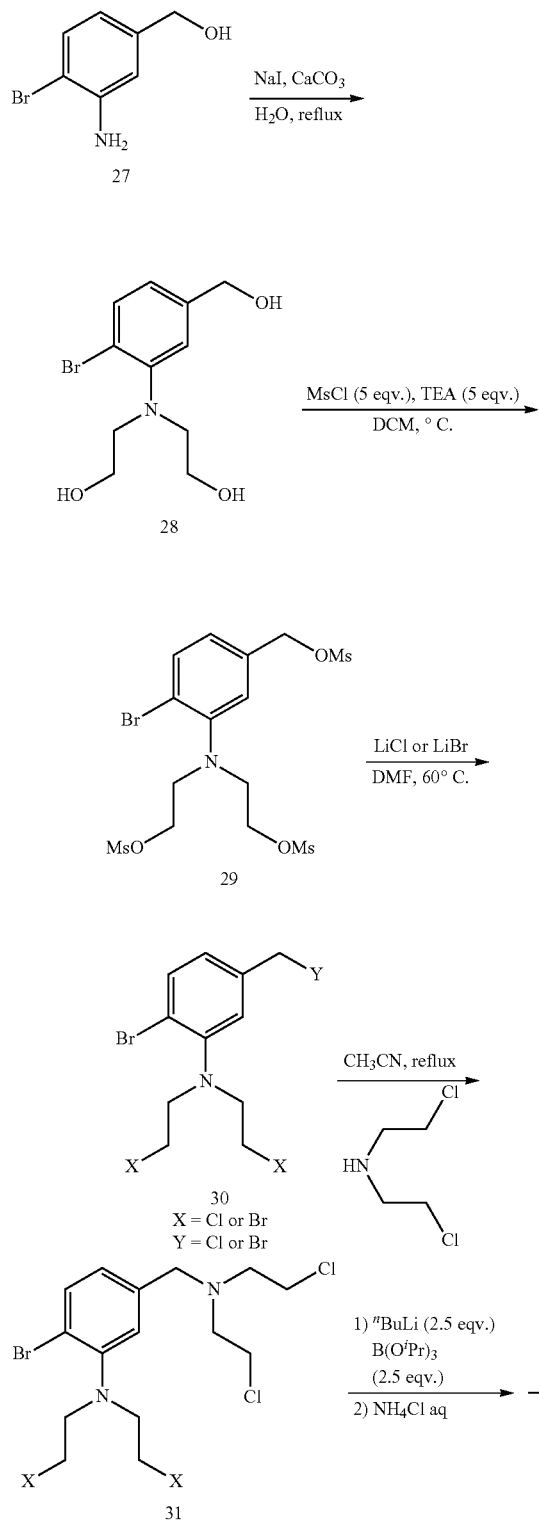

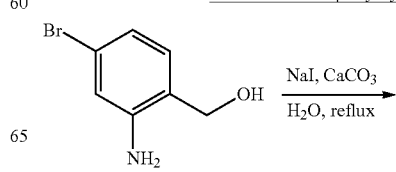

Compound 27 can be converted into 28 as illustrated in Scheme 5. 28 can be converted to 29 by treatment with methanesulfonyl chloride followed by lithium bromide or lithium chloride respectively. 30 can be converted to 31 by treated with bis(2-chloroethyl)amine. 32 can be obtained by the boronation of 31 using butyllithium as a base. 32 can be converted to boronic ester 33 and salt 34 can be obtained by treating 33 with iodomethane.

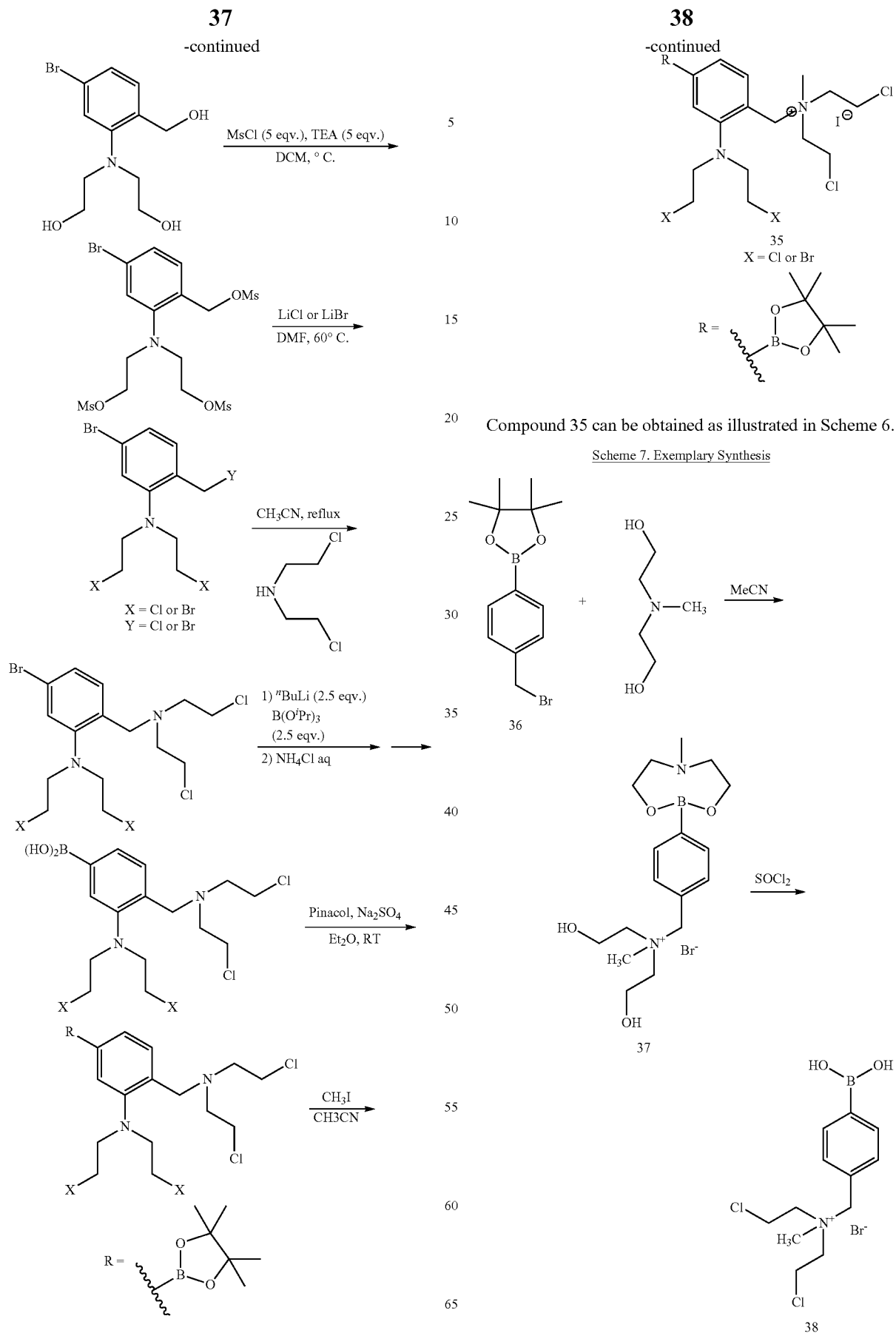
Compound 35 can be obtained as illustrated in Scheme 6.
Scheme 7. Exemplary Synthesis

39
-continued

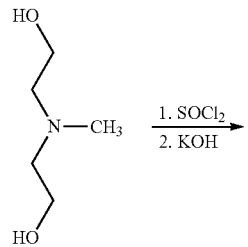
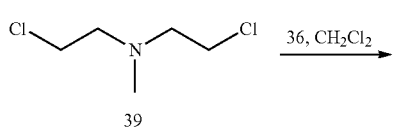
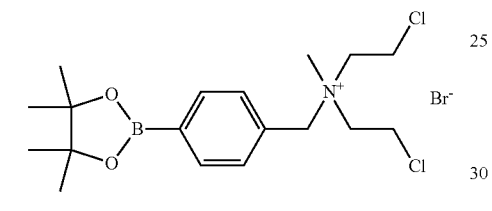

Compound 36 can be converted into 37 as illustrated in Scheme 7. SOCl$_2$ treatment of 37 can produce boronic acid 38. Compound 40 can be obtained by the reaction of 36 and nitrogen mustards 39 which can be easily synthesized from 2,2'-(methylazanediyl)diethanol.

Scheme 8. Exemplary Synthesis

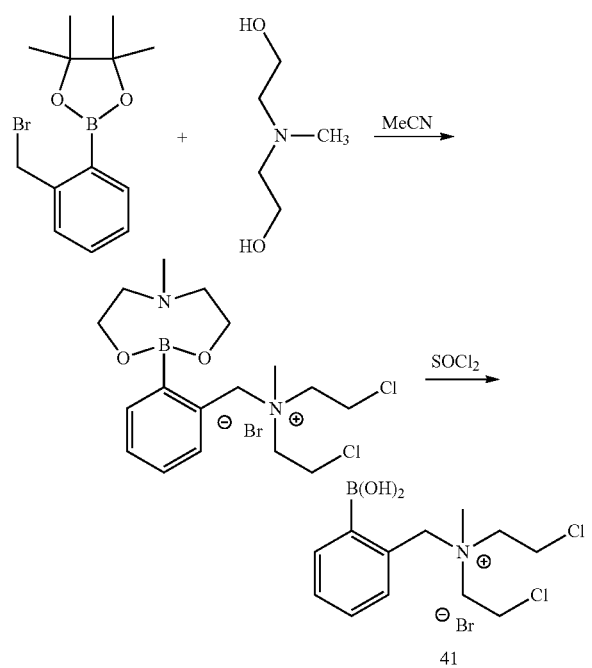

40
-continued

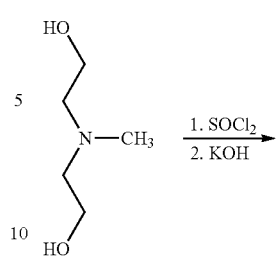
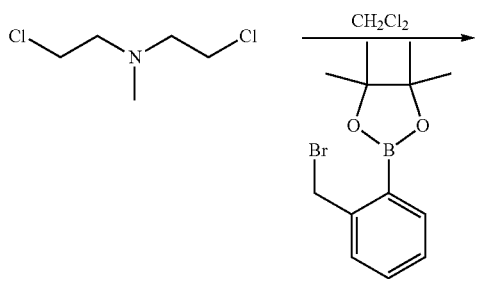
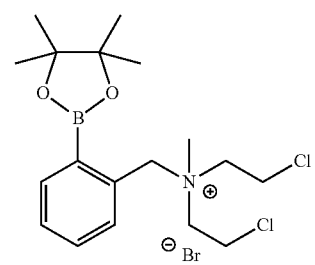

Compounds 41 and 42 can be obtained as illustrated in Scheme 8.

Scheme 9. Exemplary Synthesis

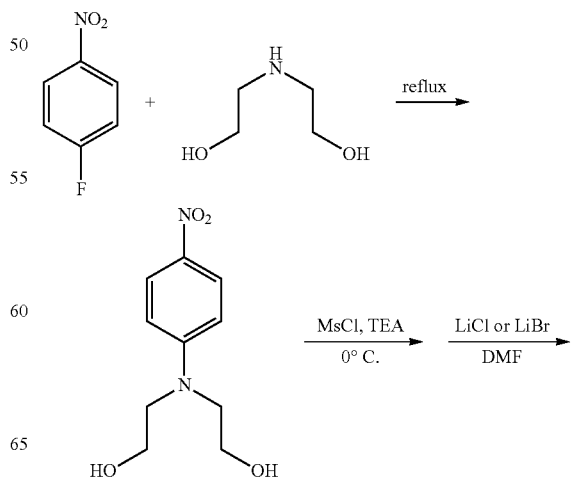

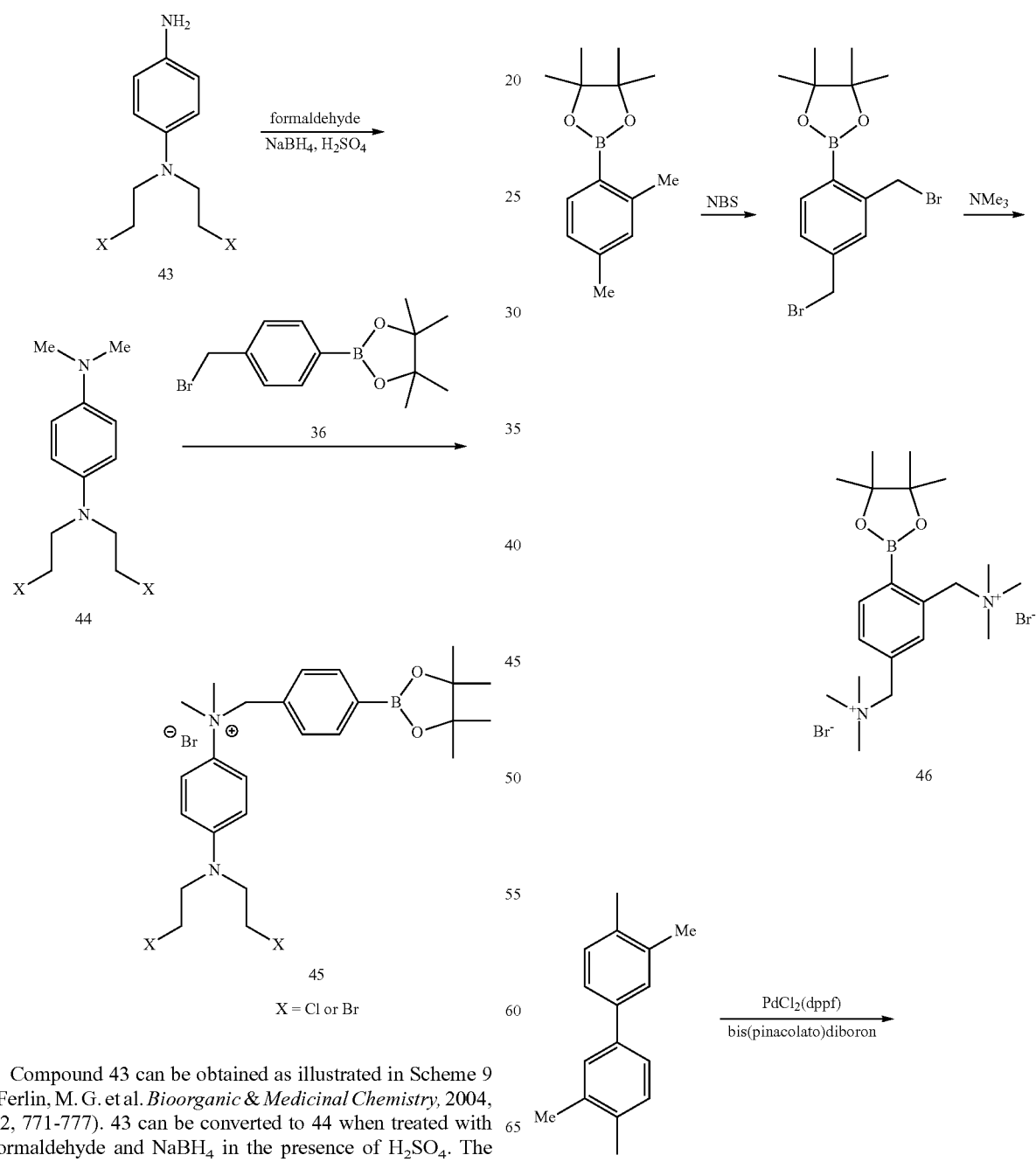
Compounds of formula (II) can be synthesized as illustrated in Scheme 10, as generally described in Peng et al. *Chem. Eur. J.* 2012, 18, 3250.
Compound 43 can be obtained as illustrated in Scheme 9 (Ferlin, M. G. et al. *Bioorganic & Medicinal Chemistry*, 2004, 12, 771-777). 43 can be converted to 44 when treated with formaldehyde and NaBH$_4$ in the presence of H$_2$SO$_4$. The reaction of 44 and 36 can produce compound 45.

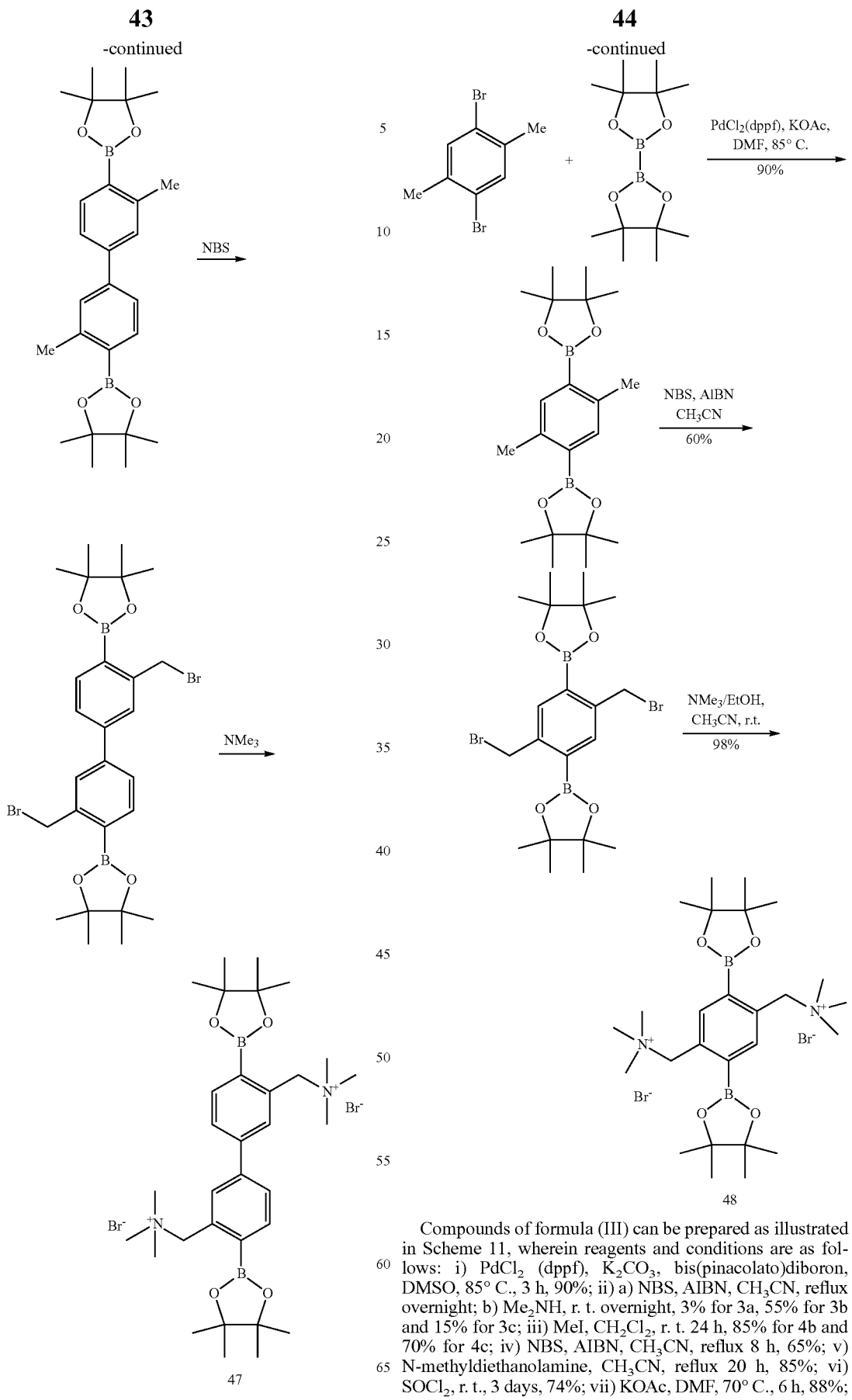

Compounds of formula (III) can be prepared as illustrated in Scheme 11, wherein reagents and conditions are as follows: i) PdCl$_2$ (dppf), K$_2$CO$_3$, bis(pinacolato)diboron, DMSO, 85° C., 3 h, 90%; ii) a) NBS, AIBN, CH$_3$CN, reflux overnight; b) Me$_2$NH, r. t. overnight, 3% for 3a, 55% for 3b and 15% for 3c; iii) MeI, CH$_2$Cl$_2$, r. t. 24 h, 85% for 4b and 70% for 4c; iv) NBS, AIBN, CH$_3$CN, reflux 8 h, 65%; v) N-methyldiethanolamine, CH$_3$CN, reflux 20 h, 85%; vi) SOCl$_2$, r. t., 3 days, 74%; vii) KOAc, DMF, 70° C., 6 h, 88%; viii) 10% KOH, reflux 24 h, 50%.

Scheme 11. Exemplary Syntheses
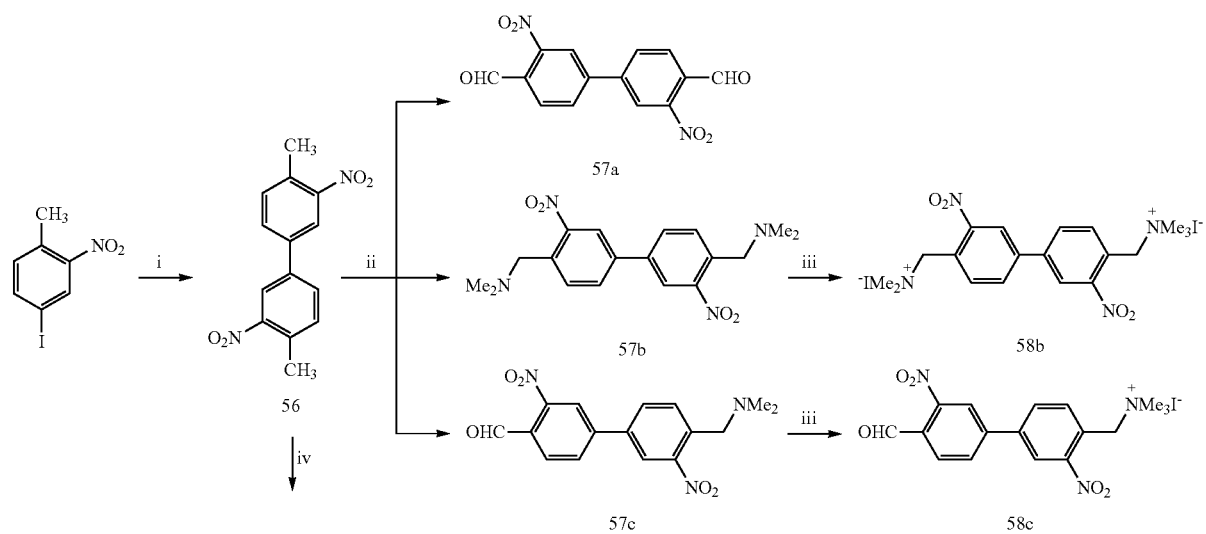
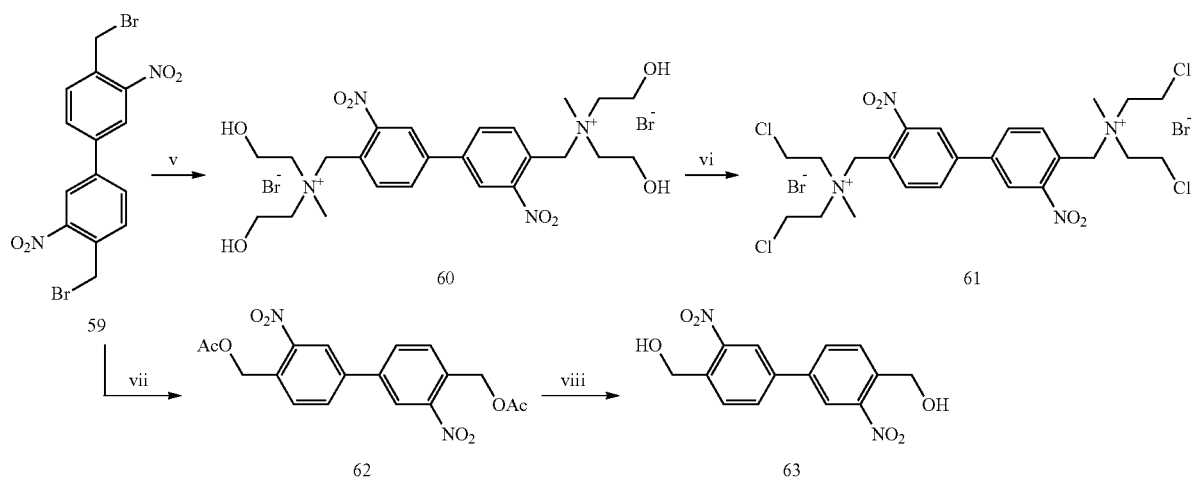

Compounds of formula (IIIa) can be prepared as illustrated in Scheme 12, wherein reagents and conditions are as follows: ix) BrCH$_2$CH$_2$Br, t-BuOK, DMF, r. t. 3 days, 45%; x) Cl$_2$CHCOO$^t$Bu, t-BuOK, DMF, −25° C., 1 h, 30%; xi) HOAc, reflux, 4 h, 70%; xii) Me$_3$N, EtOH, 40° C., 24 h, 60%.

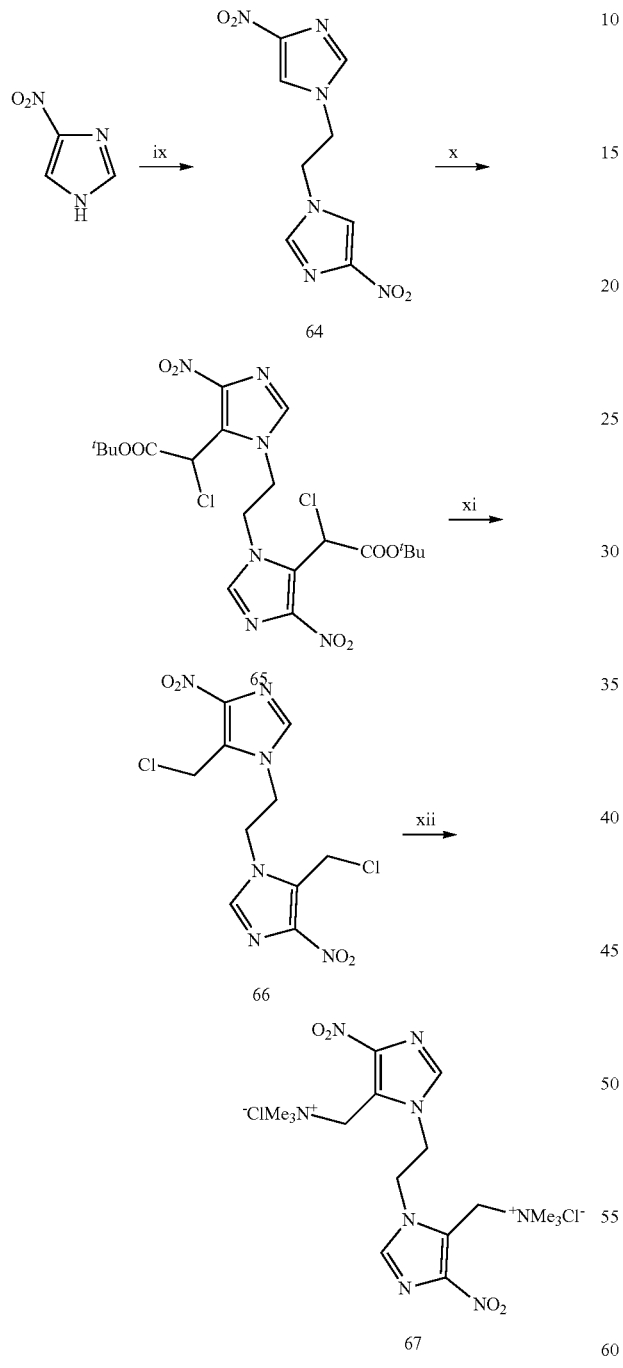

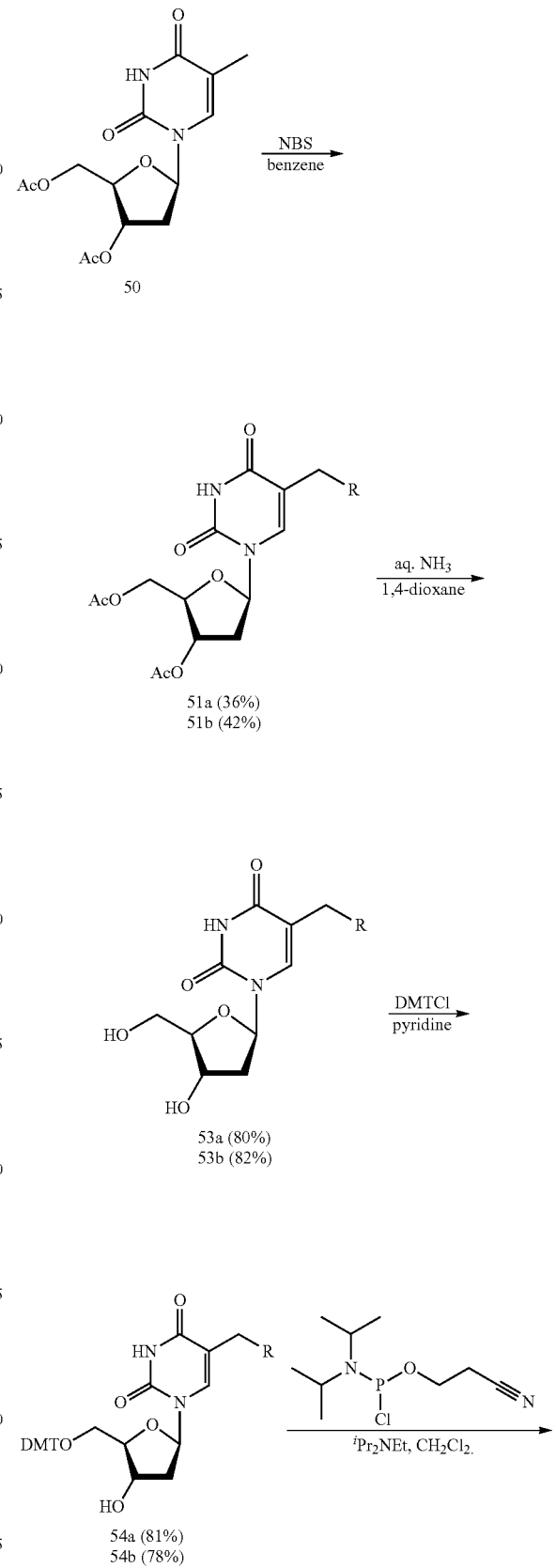

Compounds of formula (IV) such as compounds 55a,b can be prepared as illustrated in Scheme 13. Treatment of 50 with NBS can produce 51. After deprotection, 53 can be selectively protected by treatment with DMTCl in the presence of pyridine to yield 54, which can then be converted to 55.

-continued

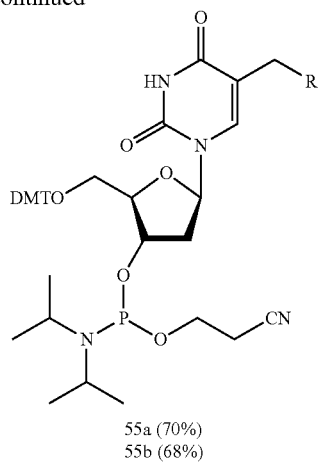

55a (70%)
55b (68%)

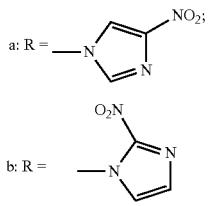

Other methods of synthesizing the compounds of the formulae herein will be evident to those of ordinary skill in the art. Synthetic chemistry transformations and protecting group methodologies (protection and deprotection) useful in synthesizing the compounds are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

Evaluation of Compounds

Compounds may be evaluated using standard methods such as NMR spectroscopy and mass spectrometry. To test the activities of compounds, standard assays may be used.

For example, compounds of formulae (I), (Ia), (II), (IIa), (III), (IIIa) and (IV), and compounds of formulae (Va), (Vb), (Vc), (Vd), (Ve) and (Vf) wherein the anti-cancer agent is an alkylating agent, may be evaluated to determine abilities to promote DNA interstrand crosslinks (ICLs). Such assays involve the use of a sample oligonucleotide duplex, such as a $^{32}$P-labeled compound, and incubating it in the presence of a compound of interest in a suitable buffer. Denaturing polyacrylamide gel electrophoresis (PAGE) will separate crosslinked DNA from single-stranded DNA, and the gel can be visualized using appropriate techniques. Compounds of formulae (I), (Ia), (II) and (IIa), which may be activated in the presence of hydrogen peroxide, can be evaluated in the presence or absence of hydrogen peroxide to evaluate selectivity. Compounds of formulae (III), (IIIa) and (V), which may be activated under hypoxic conditions and under radiation (e.g., by UV light of about 350 nm), can be evaluated in the presence or absence of such conditions to evaluate selectivity.

Compounds can also be evaluated for their activities in cancer cell lines. For example, compounds can be evaluated against a panel of 60 cell lines by the Developmental Therapeutics Program of the National Cancer Institute. Compound activities may further be compared to those in healthy cell lines.

Compounds can also be evaluated in animal models. For example, compounds can be tested using mouse xenografts as generally described in Cheng et al. Cancer Research 2012, 72(10): 2634-44.

Pharmaceutical Compositions

While a compound described herein, such as a compound of formula (I), (Ia), (II), (IIa), (III), (IIIa), (IV), (Va), (Vb), (Vc), (Vd), (Ve) or (Vf), may be administered alone in the methods described herein, it may also be presented as one or more pharmaceutical compositions (e.g., formulations). A compound described herein may be formulated with one or more pharmaceutically acceptable carriers, adjuvants, excipients, diluents, fillers, buffers, stabilizers, preservatives, lubricants, or other materials well known to those skilled in the art and optionally other therapeutic or prophylactic agents.

Accordingly, the disclosure may provide a pharmaceutical composition comprising at least one compound of formula (I), (Ia), (II), (IIa), (III), (IIIa), (IV), (Va), (Vb), (Vc), (Vd), (Ve) or (Vf). The methods described herein include administration of one or more pharmaceutical compositions, as discussed herein, in which a compound described herein is admixed together with one or more pharmaceutically acceptable carriers, excipients, buffers, adjuvants, stabilizers, or other materials, as described herein.

Suitable carriers, excipients, etc. can be found in standard pharmaceutical texts, for example, Remington's Pharmaceutical Sciences, 18th edition, Mack Publishing Company, Easton, Pa., 1990.

The pharmaceutical compositions may conveniently be presented in unit dosage form and may be prepared by any methods known in the art of pharmacy. Such methods include the step of bringing into association the active compound(s) with the carrier which constitutes one or more accessory ingredients. In general, the pharmaceutical compositions are prepared by uniformly and intimately bringing into association the active compound with liquid carriers or finely divided solid carriers or both, and then if necessary shaping the product.

Pharmaceutical compositions may be in the form of liquids, solutions, suspensions, emulsions, elixirs, syrups, tablets, lozenges, granules, powders, capsules, cachets, pills, ampoules, suppositories, pessaries, ointments, gels, pastes, creams, sprays, mists, foams, lotions, oils, boluses, electuaries, or aerosols.

Pharmaceutical compositions suitable for oral administration (e.g. by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or molding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g. sodium lauryl sulfate); and preservatives (e.g. methyl p-hydroxybenzoate, propyl p-hydroxybenzoate, sorbic acid). Molded tablets may be made by molding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Pharmaceutical compositions suitable for parenteral administration (e.g. by injection, including cutaneous, subcutaneous, intramuscular, intravenous and intradermal), include aqueous and nonaqueous isotonic, pyrogen-free, sterile injection solutions which may contain anti-oxidants, buffers, preservatives, stabilizers, bacteriostats, and solutes which render the pharmaceutical composition isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such pharmaceutical compositions include Sodium Chloride Injection, Ringer's Solution, or Lactated Ringer's Injection. The pharmaceutical compositions may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets. Pharmaceutical compositions may be in the form of liposomes or other microparticulate systems which are designed to target the active compound to blood components or one or more organs.

Pharmaceutical compositions suitable for topical administration (e.g. transdermal, intranasal, ocular, buccal, and sublingual) may be formulated as an ointment, cream, suspension, lotion, powder, solution, past, gel, spray, aerosol, or oil. Alternatively, a pharmaceutical composition may comprise a patch or a dressing such as a bandage or adhesive plaster impregnated with active compounds and optionally one or more excipients or diluents.

Pharmaceutical compositions suitable for topical administration in the mouth include lozenges comprising the active compound in a flavored basis, usually sucrose and acacia or tragacanth; pastilles comprising the active compound in an inert basis such as gelatin and glycerin, or sucrose and acacia; and mouthwashes comprising the active compound in a suitable liquid carrier.

Pharmaceutical compositions suitable for topical administration to the eye also include eye drops wherein the active compound is dissolved or suspended in a suitable carrier, especially an aqueous solvent for the active compound.

Pharmaceutical compositions suitable for nasal administration, wherein the carrier is a solid, include a coarse powder having a particle size, for example, in the range of about 20 to about 500 microns which is administered in the manner in which snuff is taken, i.e. by rapid inhalation through the nasal passage from a container of the powder held close up to the nose. Suitable pharmaceutical compositions wherein the carrier is a liquid for administration as, for example, nasal spray, nasal drops, or by aerosol administration by nebulizer, include aqueous or oily solutions of the active compound.

Pharmaceutical compositions suitable for administration by inhalation include those presented as an aerosol spray from a pressurized pack, with the use of a suitable propellant, such as dichlorodifluoromethane, trichlorofluoromethane, dichoro-tetrafluoroethane, carbon dioxide, or other suitable gases. Further pharmaceutical compositions suitable for inhalation include those presented as a nebulizer.

Pharmaceutical compositions suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical pharmaceutical compositions may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream pharmaceutical compositions.

Suitable emulgents and emulsion stabilizers include Tween 60, Span 80, cetostearyl alcohol, myristyl alcohol, glyceryl monostearate and sodium lauryl sulfate. The choice of suitable oils or fats for the pharmaceutical composition is based on achieving the desired cosmetic properties, since the solubility of the active compound in most oils likely to be used in pharmaceutical emulsion pharmaceutical compositions may be very low. Thus the cream should preferably be a non-greasy, non-staining and washable product with suitable consistency to avoid leakage from tubes or other containers. Straight or branched chain, mono- or dibasic alkyl esters such as diisoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Pharmaceutical compositions suitable for rectal administration may be presented as a suppository with a suitable base comprising, for example, cocoa butter or a salicylate.

Pharmaceutical compositions suitable for vaginal administration may be presented as pessaries, tampons, creams, gels, pastes, foams or spray pharmaceutical compositions containing in addition to the active compound, such carriers as are known in the art to be appropriate.

Dosages

It will be appreciated that appropriate dosages of the compounds and compositions comprising the active compounds, can vary from patient to patient. Determining the optimal dosage will generally involve the balancing of the level of therapeutic benefit against any risk or deleterious side effects of the treatments described herein. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound may be in the range of about 100 μg to about 250 mg per kilogram body weight of the subject per day.

Anti-Cancer Agents

In the compounds of formula (V), the compound comprises an anti-cancer agent. Exemplary anti-cancer/chemotherapeutic agents include, but are not limited to, the following:

alkylating agents (including, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), bendamustine (Treakisym®, Ribomustin®, Treanda®) chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexylen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), estramustine (Emcyt®, Estracit®), fotemustine, irofulven, mannosulfan, mitobronitol, nimustine, procarbazine, ranimustine, semustine, triaziquone, treosulfan, and Dacarbazine (DTIC-Dome®).

anti-EGFR antibodies (e.g., cetuximab (Erbitux®), panitumumab (Vectibix®), and gefitinib (Iressa®)).

anti-Her-2 antibodies (e.g., trastuzumab (Herceptin®) and other antibodies from Genentech).

antimetabolites (including, without limitation, folic acid antagonists (also referred to herein as antifolates), pyrimidine analogs, purine analogs and adenosine deaminase inhibitors): methotrexate (Rheumatrex®, Trexall®), 5-fluorouracil (Adrucil®, Efudex®, Fluoroplex®), floxuridine (FUDF®), carmofur, cytarabine (Cytosar-U®, Tarabine PFS), 6-mercaptopurine (Puri-Nethol®)), 6-thioguanine (Thioguanine Tabloid®), fludarabine phosphate (Fludara®), pentostatin (Nipent®), pemetrexed (Alimta®), raltitrexed (Tomudex®), cladribine (Leustatin®), clofarabine (Clofarex®, Clolar®), mercaptopurine (Puri-Nethol®), capecitabine (Xeloda®), nelarabine (Arranon®), azacitidine (Vidaza®), decitabine (Dacogen®), enocitabine (Sunrabin®), sapacitabine, tegafur-uracil, tiazofurine, tioguanine, trofosfamide, and gemcitabine (Gemzar®).

vinca alkaloids: vinblastine (Velban®, Velsar®), vincristine (Vincasar®, Oncovin®), vindesine (Eldisine®), vinorelbine (Navelbine®), vinflunine (Javlor®).

platinum-based agents: carboplatin (Paraplat®, Paraplatin®), cisplatin (Platinol®), oxaliplatin (Eloxatin®), nedaplatin, satraplatin, triplatin.

anthracyclines: daunorubicin (Cerubidine®, Rubidomycin®), doxorubicin (Adriamycin®), epirubicin (Ellence®), idarubicin (Idamycin®), mitoxantrone (Novantrone®), valrubicin (Valstar®), aclarubicin, amrubicin, liposomal doxorubicin, liposomal daunorubicin, pirarubicin, pixantrone, zorubicin.

topoisomerase inhibitors: topotecan (Hycamtin®), irinotecan (Camptosar®), etoposide (Toposar®, VePesid®), teniposide (Vumon®), lamellarin D, SN-38, camptothecin (e.g., IT-101), belotecan, rubitecan.

taxanes: paclitaxel (Taxol®), docetaxel (Taxotere®), larotaxel, cabazitaxel, ortataxel, tesetaxel.

antibiotics: actinomycin (Cosmegen®), bleomycin (Blenoxane®), hydroxyurea (Droxia®, Hydrea®), mitomycin (Mitozytrex®, Mutamycin®).

immunomodulators: lenalidomide (Revlimid®), thalidomide (Thalomid®).

immune cell antibodies: alemtuzamab (Campath®), gemtuzumab (Myelotarg®), rituximab (Rituxan®), tositumomab (Bexxar®).

interferons (e.g., IFN-alpha (Alferon®, Roferon-A®, Intron®-A) or IFN-gamma (Actimmune®)).

interleukins: IL-1, IL-2 (Proleukin®), IL-24, IL-6 (Sigosix®), IL-12.

HSP90 inhibitors (e.g., geldanamycin or any of its derivatives). In certain embodiments, the HSP90 inhibitor is selected from geldanamycin, 17-alkylamino-17-desmethoxygeldanamycin ("17-AAG") or 17-(2-dimethylaminoethyl) amino-17-desmethoxygeldanamycin ("17-DMAG").

anti-androgens which include, without limitation nilutamide (Nilandron®) and bicalutamide (Caxodex®).

antiestrogens which include, without limitation tamoxifen (Nolvadex®), toremifene (Fareston®), letrozole (Femara®), testolactone (Teslac®), anastrozole (Arimidex®), bicalutamide (Casodex®), exemestane (Aromasin®), flutamide (Eulexin®), fulvestrant (Faslodex®), raloxifene (Evista®, Keoxifene®) and raloxifene hydrochloride.

anti-hypercalcaemia agents which include without limitation gallium (III) nitrate hydrate (Ganite®) and pamidronate disodium (Aredia®).

apoptosis inducers which include without limitation ethanol, 2-[[3-(2,3-dichlorophenoxy)propyl]amino]-(9Cl), gambogic acid, elesclomol, embelin and arsenic trioxide (Trisenox®).

Aurora kinase inhibitors which include without limitation binucleine 2.

Bruton's tyrosine kinase inhibitors which include without limitation terreic acid.

calcineurin inhibitors which include without limitation cypermethrin, deltamethrin, fenvalerate and tyrphostin 8.

CaM kinase II inhibitors which include without limitation 5-Isoquinolinesulfonic acid, 4-[{2S)-2-[(5-isoquinolinylsulfonyl)methylamino]-3-oxo-3-{4-phenyl-1-piperazinyl)propyl]phenyl ester and benzenesulfonamide.

CD45 tyrosine phosphatase inhibitors which include without limitation phosphonic acid.

CDC25 phosphatase inhibitors which include without limitation 1,4-naphthalene dione, 2,3-bis[(2-hydroxyethyl)thio]-(9Cl).

CHK kinase inhibitors which include without limitation debromohymenialdisine.

cyclooxygenase inhibitors which include without limitation 1H-indole-3-acetamide, 1-(4-chlorobenzoyl)-5-methoxy-2-methyl-N-(2-phenylethyl)-(9Cl), 5-alkyl substituted 2-arylaminophenylacetic acid and its derivatives (e.g., celecoxib (Celebrex®), rofecoxib (Vioxx®), etoricoxib (Arcoxia®), lumiracoxib (Prexige®), valdecoxib (Bextra®) or 5-alkyl-2-arylaminophenylacetic acid).

cRAF kinase inhibitors which include without limitation 3-(3,5-dibromo-4-hydroxybenzylidene)-5-iodo-1,3-dihydroindol-2-one and benzamide, 3-(dimethylamino)-N-[3-[(4-hydroxybenzoyl)amino]-4-methylphenyl]-(9Cl).

cyclin dependent kinase inhibitors which include without limitation olomoucine and its derivatives, purvalanol B, roascovitine (Seliciclib®), indirubin, kenpaullone, purvalanol A and indirubin-3'-monooxime.

cysteine protease inhibitors which include without limitation 4-morpholinecarboxamide, N-[(1S)-3-fluoro-2-oxo-1-(2-phenylethyl)propyl]amino]-2-oxo-1-(phenylmeth-yl)ethyl]-(9Cl).

DNA intercalators which include without limitation plicamycin (Mithracin®) and daptomycin (Cubicin®).

DNA strand breakers which include without limitation bleomycin (Blenoxane®).

E3 ligase inhibitors which include without limitation N-((3,3,3-trifluoro-2-trifluoromethyl)propionyl)sulfanilamide.

EGF Pathway Inhibitors which include, without limitation tyrphostin 46, EKB-569, erlotinib (Tarceva®), gefitinib (Iressa®), lapatinib (Tykerb®) and those compounds that are generically and specifically disclosed in WO 97/02266, EP 0 564 409, WO 99/03854, EP 0 520 722, EP 0 566 226, EP 0 787 722, EP 0 837 063, U.S. Pat. No. 5,747,498, WO 98/10767, WO 97/30034, WO 97/49688, WO 97/38983 and WO 96/33980.

farnesyltransferase inhibitors which include without limitation ahydroxyfarnesylphosphonic acid, butanoic acid, 2-[(2S)-2-[[(2S,3S)-2-[[(2R)-2-amino-3-mercaptopropyl]amino]-3-methylpent-yl]oxy]-1-oxo-3-phenylpropyl]amino]-4-(methylsulfonyl)-1-methylethylester (2S)-(9Cl), tipifarnib (Zarnestra®), and manumycin A.

Flk-1 kinase inhibitors which include without limitation 2-propenamide, 2-cyano-3-[4-hydroxy-3,5-bis(1-methylethyl)phenyl]-N-(3-phenylpropyl)-(2E-)-(9Cl).

glycogen synthase kinase-3 (GSK3) inhibitors which include without limitation indirubin-3'-monooxime.

histone deacetylase (HDAC) inhibitors which include without limitation suberoylanilide hydroxamic acid (SAHA), [4-(2-amino-phenylcarbamoyl)-benzyl]-carbamic acid pyridine-3-ylmethylester and its derivatives, butyric acid, pyroxamide, trichostatin A, oxamflatin, apicidin, depsipeptide, depudecin, trapoxin, vorinostat (Zolinza®), and compounds disclosed in WO 02/22577.

I-kappa B-alpha kinase inhibitors (IKK) which include without limitation 2-propenenitrile, 3-[(4-methylphenyl)sulfonyl]-(2E)-(9Cl).

imidazotetrazinones which include without limitation temozolomide (Methazolastone®, Temodar®) and its derivatives (e.g., as disclosed generically and specifically in U.S. Pat. No. 5,260,291) and Mitozolomide.

insulin tyrosine kinase inhibitors which include without limitation hydroxyl-2-naphthalenylmethylphosphonic acid.

c-Jun-N-terminal kinase (JNK) inhibitors which include without limitation pyrazoleanthrone and epigallocatechin gallate.

mitogen-activated protein kinase (MAP) inhibitors which include without limitation benzenesulfonamide, N-[2-[[[3-(4-chlorophenyl)-2-propenyl]methyl]amino]methyl]phenyl]-N-(2-hy-droxyethyl)-4-methoxy-(9Cl).

MDM2 inhibitors which include without limitation trans-4-iodo, 4'-boranyl-chalcone.

MEK inhibitors which include without limitation butanedinitrile, bis[amino[2-aminophenyl)thio]methylene]-(9Cl).

MMP inhibitors which include without limitation Actinonin, epigallocatechin gallate, collagen peptidomimetic and non-peptidomimetic inhibitors, tetracycline derivatives marimastat (Marimastat®), prinomastat, incyclinide (Metastat®), shark cartilage extract AE-941 (Neovastat®), Tanomastat, TAA211, MMI270B or AAJ996.

mTor inhibitors which include without limitation rapamycin (Rapamune®), and analogs and derivatives thereof, AP23573 (also known as ridaforolimus, deforolimus, or MK-8669), CCI-779 (also known as temsirolimus) (Torisel®) and SDZ-RAD.

NGFR tyrosine kinase inhibitors which include without limitation tyrphostin AG 879.

p38 MAP kinase inhibitors which include without limitation Phenol, 4-[4-(4-fluorophenyl)-5-(4-pyridinyl)-1H-imidazol-2-yl]-(9Cl), and benzamide, 3-(dimethylamino)-N-[3-[(4-hydroxylbenzoyl)amino]-4-methylphenyl]-(9Cl).

p56 tyrosine kinase inhibitors which include without limitation damnacanthal and tyrphostin 46.

PDGF pathway inhibitors which include without limitation tyrphostin AG 1296, tyrphostin 9, 1,3-butadiene-1,1,3-tricarbonitrile, 2-amino-4-(1H-indol-5-yl)-(9Cl), imatinib (Gleevec®) and gefitinib (Iressa®) and those compounds generically and specifically disclosed in European Patent No.: 0 564 409 and PCT Publication No.: WO 99/03854.

phosphatidylinositol 3-kinase inhibitors which include without limitation wortmannin, and quercetin dihydrate.

phosphatase inhibitors which include without limitation cantharidic acid, cantharidin, and L-leucinamide.

protein phosphatase inhibitors which include without limitation cantharidic acid, cantharidin, L-P-bromotetramisole oxalate, 2(5H)-furanone, 4-hydroxy-5-(hydroxymethyl)-3-(1-oxohexadecyl)-(5R)-(9Cl) and benzylphosphonic acid.

PKC inhibitors which include without limitation 1-H-pyrollo-2,5-dione,3-[1-3-(dimethylamino)propyl]-1H-indol-3-yl]-4-(1H-indol-3-yl)-(9Cl), Bisindolylmaleimide IX, Sphinogosine, staurosporine, and Hypericin.

PKC delta kinase inhibitors which include without limitation rottlerin.

polyamine synthesis inhibitors which include without limitation DMFO.

PTP1B inhibitors which include without limitation L-leucinamide.

protein tyrosine kinase inhibitors which include, without limitation tyrphostin Ag 216, tyrphostin Ag 1288, tyrphostin Ag 1295, geldanamycin, genistein and 7H-pyrrolo[2,3-d]pyrimidine derivatives as generically and specifically described in PCT Publication No.: WO 03/013541 and U.S. Publication No.: 2008/0139587.

SRC family tyrosine kinase inhibitors which include without limitation PP1 and PP2.

Syk tyrosine kinase inhibitors which include without limitation piceatannol.

Janus (JAK-2 and/or JAK-3) tyrosine kinase inhibitors which include without limitation tyrphostin AG 490 and 2-naphthyl vinyl ketone.

retinoids which include without limitation isotretinoin (Accutane®, Amnesteem®, Cistane®, Claravis®, Sotret®) and tretinoin (Aberel®, Aknoten®, Avita®, Renova®, Retin-A®, Retin-A MICRO®, Vesanoid®).

RNA polymerase II elongation inhibitors which include without limitation 5,6-dichloro-1-beta-D-ribofuranosylbenzimidazole.

serine/Threonine kinase inhibitors which include without limitation 2-aminopurine.

sterol biosynthesis inhibitors which include without limitation squalene epoxidase and CYP2D6.

VEGF pathway inhibitors, which include without limitation anti-VEGF antibodies, e.g., bevacizumab, and small molecules, e.g., sunitinib (Sutent®), sorafinib (Nexavar®), ZD6474 (also known as vandetanib) (Zactima™), SU6668, CP-547632 and AZD2171 (also known as cediranib) (Recentin™).

Examples of chemotherapeutic agents are also described in the scientific and patent literature, see, e.g., Bulinski (1997) J. Cell Sci. 110:3055-3064; Panda (1997) Proc. Natl. Acad. Sci. USA 94:10560-10564; Muhlradt (1997) Cancer Res. 57:3344-3346; Nicolaou (1997) Nature 387:268-272; Vasquez (1997) Mol. Biol. Cell. 8:973-985; Panda (1996) J. Biol. Chem. 271:29807-29812.

Other exemplary anti-cancer agents include alitretinon, altretamine, aminopterin, aminolevulinic acid, amsacrine (Amsidine®), asparaginase (crisantaspase, Erwinase®), atrasentan, bexarotene (Targretin®), carboquone, demecolcine, efaproxiral, elsamitrucin, etoglucid, hydroxycarbamide, leucovorin, lonidamine, lucanthone, masoprocol, methyl aminolevulinate, mitoguazone, mitotane (Lysodren®), oblimersen, omacetaxine (Genasense®), pegaspargase (Oncaspar®), porfimer sodium (Photofrin®), prednimustine, sitimagene ceradenovec (Cerepro®), talaporfin, temoporfin, trabectedin (Yondelis®), and verteporfin.

3. METHODS OF USE

The disclosure further provides a method of treating cancer in a subject in need of treatment, comprising administering the subject a therapeutically effective amount of a compound described herein, such as a compound of formula (I), (Ia), (II), (IIa), (III), (IIIa), (IV), (Va), (Vb), (Vc), (Vd), (Ve) or (Vf). In embodiments, the subject is a human.

The disclosure further provides a method of reducing the proliferation of a cancer cell, comprising contacting the cancer cell with an effective amount of a compound described herein, such as a compound of formula (I), (Ia), (II), (IIa), (III), (IIIa), (IV), (Va), (Vb), (Vc), (Vd), (Ve) or (Vf).

The methods described herein can be used with any cancer, for example those described by the National Cancer Institute. The cancer can be a carcinoma, a sarcoma, a myeloma, a leukemia, a lymphoma or a mixed type. Exemplary cancers described by the National Cancer Institute include:

Digestive/gastrointestinal cancers such as anal cancer; bile duct cancer; extrahepatic bile duct cancer; appendix cancer; carcinoid tumor, gastrointestinal cancer; colon cancer; colorectal cancer including childhood colorectal cancer; esophageal cancer including childhood esophageal cancer; gallbladder cancer; gastric (stomach) cancer including childhood gastric (stomach) cancer; hepatocellular (liver) cancer including adult (primary) hepatocellular (liver) cancer and childhood (primary) hepatocellular (liver) cancer; pancreatic cancer including childhood pancreatic cancer; sarcoma, rhabdomyosarcoma; islet cell pancreatic cancer; rectal cancer; and small intestine cancer;

Endocrine cancers such as islet cell carcinoma (endocrine pancreas); adrenocortical carcinoma including childhood adrenocortical carcinoma; gastrointestinal carcinoid tumor; parathyroid cancer; pheochromocytoma; pituitary tumor; thyroid cancer including childhood thyroid cancer; childhood multiple endocrine neoplasia syndrome; and childhood carcinoid tumor;

Eye cancers such as intraocular melanoma; and retinoblastoma;

Musculoskeletal cancers such as Ewing's family of tumors; osteosarcoma/malignant fibrous histiocytoma of the bone; childhood rhabdomyosarcoma; soft tissue sarcoma including adult and childhood soft tissue sarcoma; clear cell sarcoma of tendon sheaths; and uterine sarcoma;

Breast cancer such as breast cancer including childhood and male breast cancer and pregnancy;

Neurologic cancers such as childhood brain stem glioma; brain tumor; childhood cerebellar astrocytoma; childhood cerebral astrocytoma/malignant glioma; childhood ependymoma; childhood medulloblastoma; childhood pineal and supratentorial primitive neuroectodermal tumors; childhood visual pathway and hypothalamic glioma; other childhood brain cancers; adrenocortical carcinoma; central nervous system lymphoma, primary; childhood cerebellar astrocytoma; neuroblastoma; craniopharyngioma; spinal cord tumors; central nervous system atypical teratoid/rhabdoid tumor; central nervous system embryonal tumors; and childhood supratentorial primitive neuroectodermal tumors and pituitary tumor;

Genitourinary cancers such as bladder cancer including childhood bladder cancer; renal cell (kidney) cancer; ovarian cancer including childhood ovarian cancer; ovarian epithelial cancer; ovarian low malignant potential tumor; penile cancer; prostate cancer; renal cell cancer including childhood renal cell cancer; renal pelvis and ureter, transitional cell cancer; testicular cancer; urethral cancer; vaginal cancer; vulvar cancer; cervical cancer; Wilms tumor and other childhood kidney tumors; endometrial cancer; and gestational trophoblastic tumor;

Germ cell cancers such as childhood extracranial germ cell tumor; extragonadal germ cell tumor; ovarian germ cell tumor; and testicular cancer;

Head and neck cancers such as lip and oral cavity cancer; oral cancer including childhood oral cancer; hypopharyngeal cancer; laryngeal cancer including childhood laryngeal cancer; metastatic squamous neck cancer with occult primary; mouth cancer; nasal cavity and paranasal sinus cancer; nasopharyngeal cancer including childhood nasopharyngeal cancer; oropharyngeal cancer; parathyroid cancer; pharyngeal cancer; salivary gland cancer including childhood salivary gland cancer; throat cancer; and thyroid cancer;

Hematologic/blood cell cancers such as a leukemia (e.g., acute lymphoblastic leukemia including adult and childhood acute lymphoblastic leukemia; acute myeloid leukemia including adult and childhood acute myeloid leukemia; chronic lymphocytic leukemia; chronic myelogenous leukemia; and hairy cell leukemia); a lymphoma (e.g., AIDS-related lymphoma; cutaneous T-cell lymphoma; Hodgkin's lymphoma including adult and childhood Hodgkin's lymphoma and Hodgkin's lymphoma during pregnancy; non-Hodgkin's lymphoma including adult and childhood non-Hodgkin's lymphoma and non-Hodgkin's lymphoma during pregnancy; mycosis fungoides; Sezary syndrome; Waldenstrom's macroglobulinemia; and primary central nervous system lymphoma); and other hematologic cancers (e.g., chronic myeloproliferative disorders; multiple myeloma/plasma cell neoplasm; myelodysplastic syndromes; and myelodysplastic/myeloproliferative disorders);

Lung cancer such as non-small cell lung cancer; and small cell lung cancer;

Respiratory cancers such as malignant mesothelioma, adult; malignant mesothelioma, childhood; malignant thymoma; childhood thymoma; thymic carcinoma; bronchial adenomas/carcinoids including childhood bronchial adenomas/carcinoids; pleuropulmonary blastoma; non-small cell lung cancer; and small cell lung cancer;

Skin cancers such as Kaposi's sarcoma; Merkel cell carcinoma; melanoma; and childhood skin cancer;

AIDS-related malignancies;

Other childhood cancers, unusual cancers of childhood and cancers of unknown primary site;

and metastases of the aforementioned cancers.

When a compound of formula (I), (Ia), (II), (IIa), (III), (IIIa), (IV), (Va), (Vb), (Vc), (Vd), (Ve) or (Vf) contacts a cancer cell (e.g., in a sample or in a subject), the compound may react to produce an active anti-cancer agent. By contrast, the compound may not undergo a reaction in a healthy cell.

For example, an exemplary compound of formula (I) may react with hydrogen peroxide in a cancer cell as illustrated in Scheme 14.

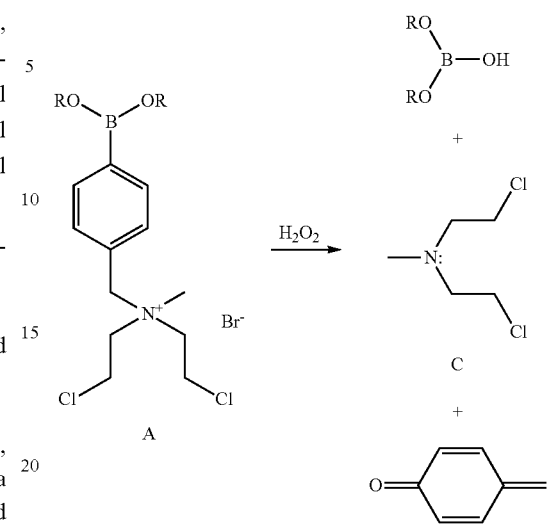

Scheme 14.

Compound C is a nitrogen mustard which may subsequently alkylate DNA, e.g., via formation of an interstrand cross-link. Another exemplary compound of formula (I) may react with hydrogen peroxide in a cancer cell as illustrated in Scheme 15.

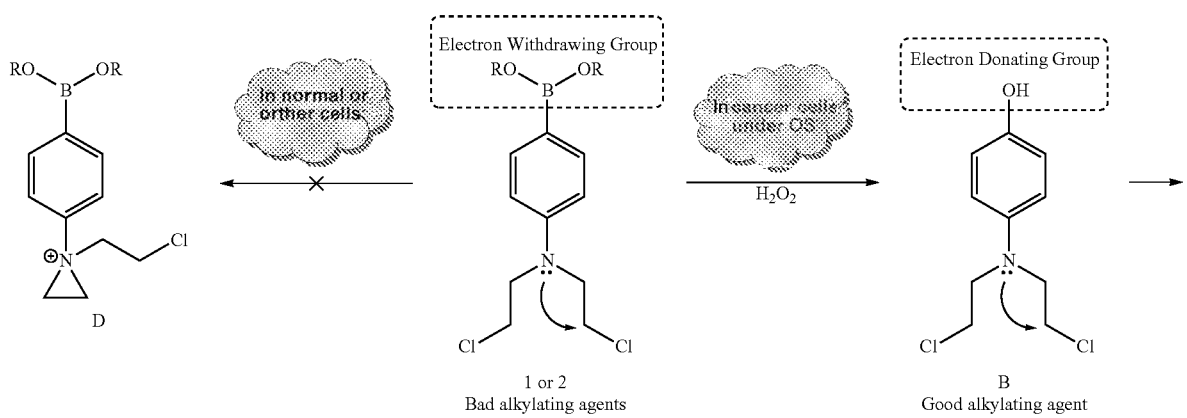

Scheme 15.

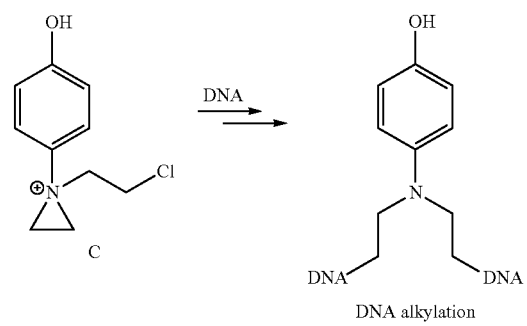

DNA alkylation

A compound of formula (II) may react with hydrogen peroxide in a cancer cell as illustrated in Scheme 16.
Scheme 16.
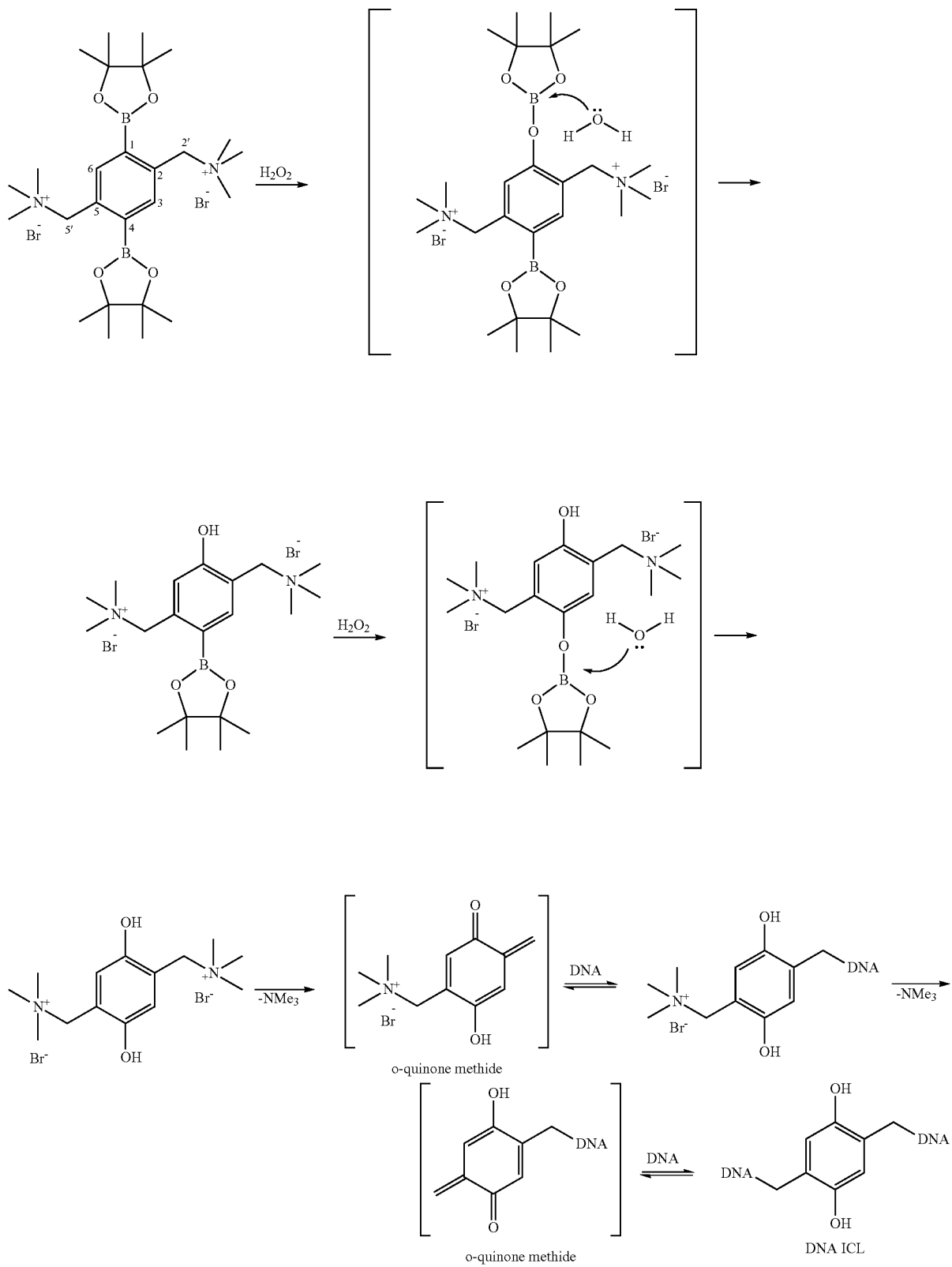

Compounds of formula (IV) may react under hypoxic conditions, and after irradiation, as illustrated in Scheme 17.

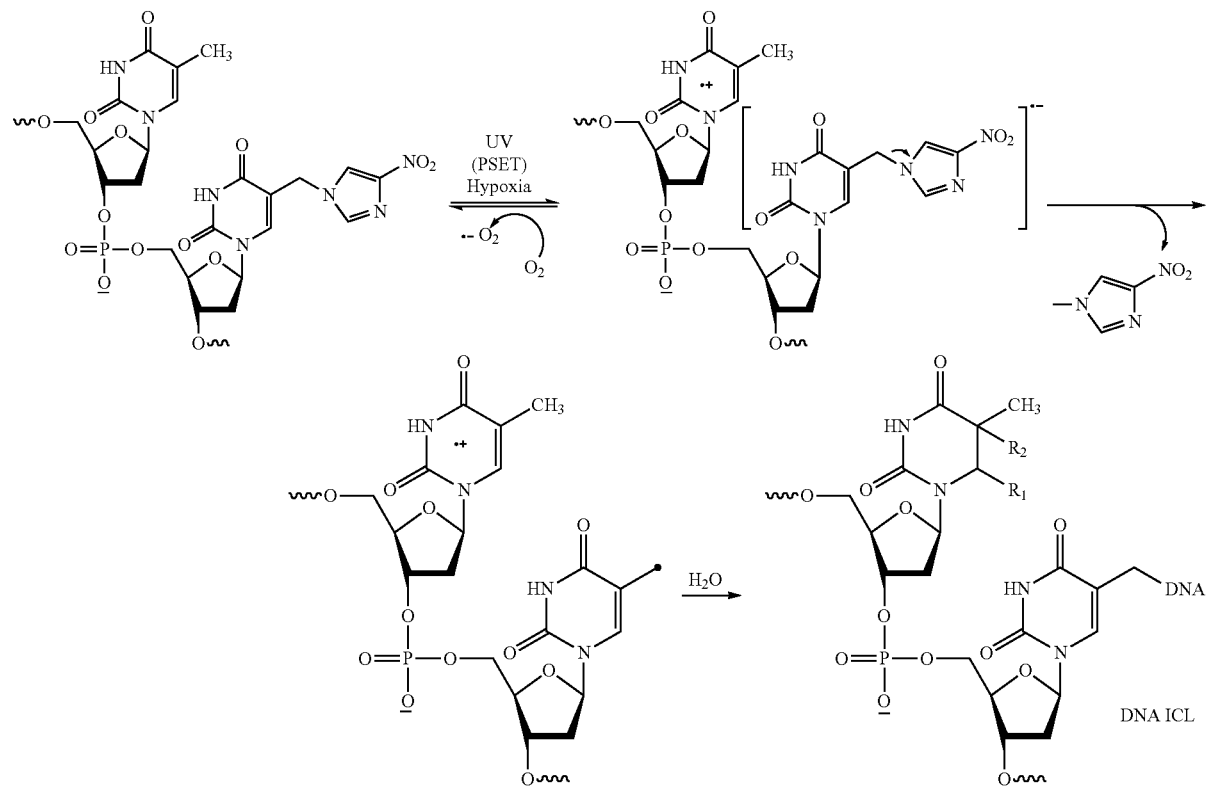

Scheme 17.

Cancer Combination Therapy

A compound described herein may be used in combination with other known therapies. Administered "in combination," as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

A compound described herein and the at least one additional therapeutic agent can be administered simultaneously, in the same or in separate compositions, or sequentially. For sequential administration, the compound described herein can be administered first, and the additional agent can be administered subsequently, or the order of administration can be reversed.

In some embodiments, a compound described herein are administered in combination with other therapeutic treatment modalities, including surgery, radiation, cryosurgery, and/or thermotherapy. Such combination therapies may advantageously utilize lower dosages of the administered agent and/or other chemotherapeutic agent, thus avoiding possible toxicities or complications associated with the various therapies. The phrase "radiation" includes, but is not limited to, external-beam therapy which involves three dimensional, conformal radiation therapy where the field of radiation is designed to conform to the volume of tissue treated; interstitial-radiation therapy where seeds of radioactive compounds are implanted using ultrasound guidance; and a combination of external-beam therapy and interstitial-radiation therapy.

In some embodiments, the compound described herein is administered with at least one additional therapeutic agent, such as a chemotherapeutic agent. In certain embodiments, the compound described herein is administered in combination with one or more additional chemotherapeutic agents, e.g., with one or more chemotherapeutic agents described herein.

In some embodiments, the compound described herein is administered in combination with a chemotherapeutic agent. Exemplary classes of chemotherapeutic agents include those described herein.

It will be readily apparent to those skilled in the art that other suitable modifications and adaptations of the compounds and methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples which are merely intended only to illustrate some aspects and embodiments of the disclosure, and should not be viewed as limiting to the scope of the disclosure. The disclosures of all journal references, U.S. patents and publications referred to herein are hereby incorporated by reference in their entireties.

EXAMPLES

General Experimental and Analytical Details

Unless otherwise specified, chemicals were purchased from Aldrich or Fisher Scientific and were used as received without further purification. $T_4$ polynucleotide kinase was obtained from New England Biolabs. Oligonucleotides were synthesized via standard automated DNA synthesis techniques using an Applied Biosystems model 394 instrument in a 1.0 M scale using commercial 1000 Å CPG-succinyl-nucleoside supports. Deprotection of the nucleobases and phosphate moieties as well as cleavage of the linker were carried out under mild deprotection conditions using a mixture of 40% aq. $MeNH_2$ and 28% aq. $NH_3$ (1:1) at room temperature for 2 h. Radiolabeling was carried out according to the standard protocols (Maniatis, T.; Fritsch, E. F.; Sambrook, J. Molecular Cloning; Cold Spring Harbor Laboratory, Cold Spring Harbor, N.Y., 1982). [$\gamma$-$^{32}$P]ATP and [$\alpha$-$^{32}$P]ATP was purchased from Perkin-Elmer Life Sciences. Quantification of radiolabeled oligonucleotides was carried out using a Molecular Dynamics Phosphorimager equipped with ImageQuant Version 5.2 software. $^1$H NMR and $^{13}$C NMR spectra were taken on either a Bruker DRX 300 or DRX 500 MHz spectrophotometer. High resolution mass spectrometry was performed at University of Kansas Mass Spectrometry Lab.

Example 1

Compound Synthesis

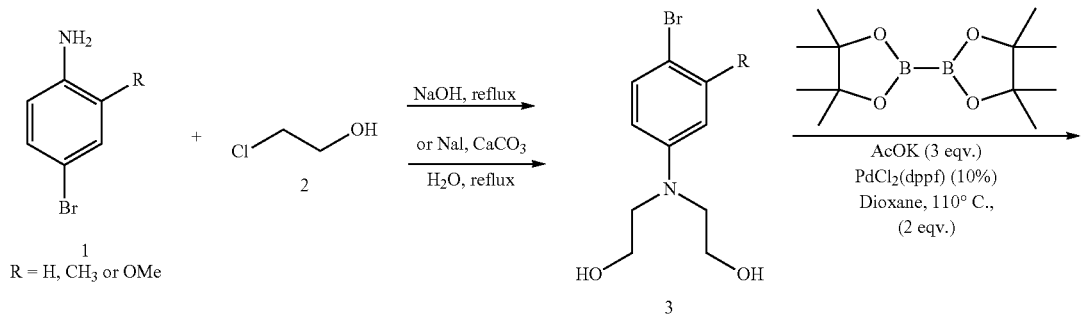

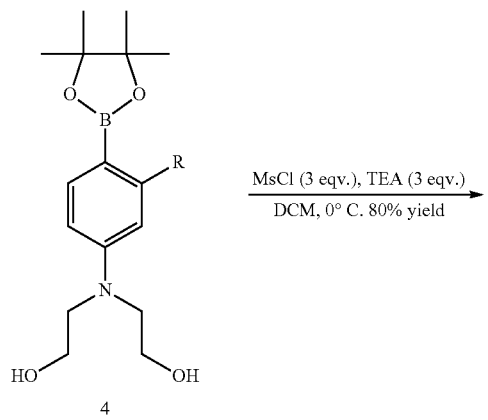

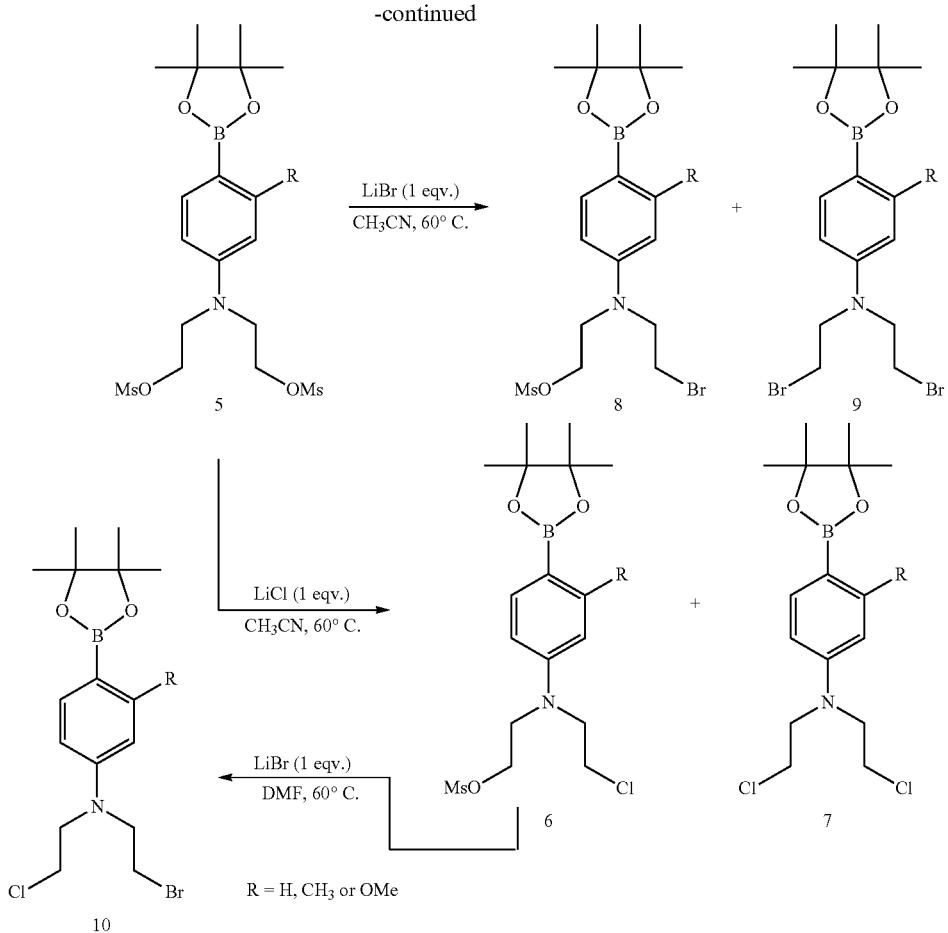

2,2'-(4-bromophenylazanediyl)diethanol (3a, R═H)

Procedure A: Sodium hydroxide (8.0 g, 0.2 mol) was added to a solution of 4-bromoaniline (17.1 g, 0.1 mol) in 2-chloroethanol (20 mL), after stirred at 100° C. for 3 days, the result mixture was cooled to room temperature, then 1 N NaOH aqueous solution was added to make sure PH>7. The mixture was exacted with dichloromethane and washed with water, after evaporation of the solvent, the residue was purified by column chromatography (Hexane/Ethyl Acetate=1:2) to afford white solid 3a, the yield was 58% after the starting material and mono-substitute product was recycled. $^1$H NMR (CDCl$_3$, 300 MHz): δ 3.51 (t, J=4.8 Hz, 4H), 3.78 (t, J=4.8 Hz, 4H), 3.92 (s, 2H), 6.53 (d, J=9.3 Hz, 2H), 7.28 (d, J=9.3 Hz, 2H); $^{13}$C NMR (CDCl$_3$, 75 MHz): δ 55.3, 60.5, 108.8, 114.2, 131.9, 146.8; HRMS-ES (m/z) [M+H]$^+$ calcd: for $C_{10}H_{14}BrNO_2$: 260.0286. Found: 260.0302. Procedure B: 4-bromoaniline (17.1 g, 0.1 mol), 2-chloroethanol (20 mL), CaCO$_3$ (20.0 g) and NaI (1.4 g) were added to 250 mL water and reflux overnight. The mixture was exacted with dichloromethane and washed with water, after evaporation of the solvent, the residue was purified by column chromatography (Hexane/Ethyl Acetate=1:2) to afford white solid 3a, the yield was 80%.

2,2'-(4-(4,4,5,5-tetramethyl-1,3,2-dioxaborolan-2-yl)phenylazanediyl)diethanol (4a, R═H)

2,2'-(4-bromophenylazanediyl)diethanol (3.8 g, 14.7 mmol), bis(pinacolaco) (7.4 g, 29.4 mmol), KOAc (4.3 g, 43.9 mol) and PdCl$_2$ (dppf) (1.1 g, 1.5 mmol) were dissolved in dioxane (100 ml). The mixture was flushed with argon for 30 minutes, and then refluxed overnight. The mixture was cooled to room temperature, extracted with ethyl acetate, washed with brine, dried over Na$_2$SO$_4$ and concentrated in vacuo, the residue was purified by column chromatography (Hexane/Ethyl Acetate=1:2) to afford white foam 4 (2.52 g, 50%). $^1$H NMR (CDCl$_3$, 300 MHz): δ 1.35 (s, 12H), 3.59 (t, J=4.8 Hz, 4H), 3.82 (t, J=4.8 Hz, 4H), 4.08 (s, 2H), 6.64 (d, J=8.7 Hz, 2H), 7.68 (d, J=8.7 Hz, 2H); $^{13}$C NMR (CDCl$_3$, 75 MHz): δ 24.8, 55.1, 60.6, 83.3, 111.4, 136.3, 150.1; HRMS-ES (m/z) [M+H]$^+$ calcd: for $C_{16}H_{27}NO_4B$: 308.2033. Found: 308.2013.

2,2'-(4-(4,4,5,5-tetramethyl-1,3,2-dioxaborolan-2-yl)phenylazanediyl)bis(ethane-2,1-diyl)dimethanesulfonate (5a, R═H)

A stirred solution of 7 (2.0 g, 5.83 mmol) and Et$_3$N (2.3 mL, 17.5 mmol) in dry CH$_2$Cl$_2$ (50 mL) was treated dropwise at 0° C. with MsCl (1.4 mL, 17.5 mmol). After 30 min, the mixture was exacted with CH$_2$Cl$_2$ and washed with brine water, dried over Na$_2$SO$_4$ and concentrated in vacuo, the residue was purified by column chromatography (Hexane/Ethyl Acetate=1:1) and followed by single recrystallization to afford white crystal solid 5a (2.1 g, 80%). $^1$H NMR (CDCl$_3$, 300 MHz): δ 1.33 (s, 12H), 2.96 (s, 6H), 3.81 (t, J=5.7 Hz, 4H), 4.37 (t, J=5.7 Hz, 4H), 6.71 (d, J=9.0 Hz, 2H), 7.71 (d, J=9.0 Hz, 2H); $^{13}$C NMR (CDCl$_3$, 75 MHz): δ 24.9, 37.4, 50.4, 66.4, 83.4, 111.4, 136.7, 137.0, 148.5; HRMS-ES (m/z) [M+Na]+ calcd: for $C_{18}H_{30}NO_8S_2BNa$: 486.1404. Found: 486.1387.

N,N-bis(2-chloroethyl)-4-(4,4,5,5-tetramethyl-1,3,2-dioxaborolan-2-yl)aniline (7a, R=H)

A mixture of 5a (926 mg, 2 mmol) and LiCl (84 mg, 2 mmol) in acetonitrile (5 mL) was stirred at 60° C. for 18 h. After removal of solvent, the residue was purified by column chromatography (Hexane/Ethyl Acetate=6:1) to afford white solid 7a (233 mg, 34%). $^1$H NMR: (CDCl$_3$, 300 MHz): δ 1.35 (s, 12H), 3.66 (t, J=6.9 Hz, 4H), 4.37 (t, J=6.9 Hz, 4H), 6.68 (d, J=8.7 Hz, 2H), 7.73 (d, J=8.7 Hz, 2H); $^{13}$C NMR (CDCl$_3$, 75 MHz): δ 24.8, 40.3, 53.3, 83.5, 111.0, 136.7, 148.3; HRMS-ES (m/z) [M+H]+ calcd: for $C_{16}H_{25}NO_2Cl_2B$: 344.1355. Found: 344.1365.

Further elution with Hexane/Ethyl Acetate 3:1 gave white oil 6a (226 mg, 28%). $^1$H NMR (CDCl$_3$, 300 MHz): δ 1.34 (s, 12H), 2.95 (s, 3H), 3.66 (t, J=6.3 Hz, 2H), 3.75-3.83 (m, 4H), 4.34 (t, J=5.7 Hz, 2H), 6.70 (d, J=8.7 Hz, 2H), 7.72 (d, J=8.7 Hz, 2H); $^{13}$C NMR (CDCl$_3$, 75 MHz): δ 24.9, 37.5, 40.4, 50.3, 53.2, 66.4, 83.4, 111.2, 136.7, 148.5; HRMS-ES (m/z) [M+H]+ calcd: for $C_{17}H_{28}NO_5SBCl$: 404.1470. Found: 404.1497.

2-((2-bromoethyl)(4-(4,4,5,5-tetramethyl-1,3,2-dioxaborolan-2-yl)phenyl)amino)ethyl methanesulfonate (9a, R=H)

A mixture of 5a (926 mg, 2 mmol) and LiBr (170 mg, 2 mmol) in acetonitrile (10 mL) was stirred at 60° C. for 20 h. After removal of solvent, the residue was purified by column chromatography (Hexane/Ethyl Acetate=6:1) to afford white solid 1e (276 mg, 32%). $^1$H NMR (CDCl$_3$, 300 MHz): δ 1.35 (s, 12H), 3.66 (t, J=7.2 Hz, 4H), 3.79 (t, J=7.2 Hz, 4H), 6.68 (d, J=8.4 Hz, 2H), 7.73 (d, J=8.4 Hz, 2H); $^{13}$C NMR (CDCl$_3$, 75 MHz): δ 24.8, 40.3, 53.2, 83.4, 110.9, 136.7, 148.4.

Further elution with Hexane/Ethyl Acetate 3:1 gave white oil 8a (277 mg, 31%). $^1$H NMR (CDCl$_3$, 300 MHz): δ 1.34 (s, 12H), 2.97 (s, 3H), 3.66 (t, J=6.9 Hz, 2H), 3.76-3.85 (m, 4H), 4.37 (t, J=5.7 Hz, 2H), 6.70 (d, J=8.4 Hz, 2H), 7.72 (d, J=8.4 Hz, 2H); $^{13}$C NMR (CDCl$_3$, 75 MHz): δ 24.9, 37.5, 40.4, 50.3, 53.2, 66.4, 83.4, 111.2, 136.7, 148.5; HRMS-ES (m/z) [M–H+Na]+ calcd: for $C_{17}H_{26}NO_5SBrBNa$: 469.0706. Found: 469.0721.

N-(2-bromoethyl)-N-(2-chloroethyl)-4-(4,4,5,5-tetramethyl-1,3,2-dioxaborolan-2-yl)aniline (10a, R=H)

A mixture of 6a (806 mg, 2 mmol) and LiBr (170 mg, 2 mmol) in DMF (2 mL) was stirred at 60° C. for 30 min. The mixture was exacted with $CH_2Cl_2$ and washed with brine water, dried over $Na_2SO_4$ and concentrated in vacuo, the residue was purified by column chromatography (Hexane/Ethyl Acetate=10:1) to afford white foam 10a (696 g, 90%). $^1$H NMR (CDCl$_3$, 500 MHz): δ 1.35 (s, 12H), 3.49 (t, J=7.5 Hz, 2H), 3.66 (t, J=6.9 Hz, 4H), 3.77-3.78 (m, 2H), 3.84 (t, J=7.5 Hz, 2H), 6.68 (d, J=8.5 Hz, 2H), 7.73 (d, J=8.5 Hz, 2H); $^{13}$C NMR (CDCl$_3$, 75 MHz): δ 24.8, 40.3, 53.2, 83.4, 110.9, 136.7, 148.4.

Example 2

Compound Synthesis

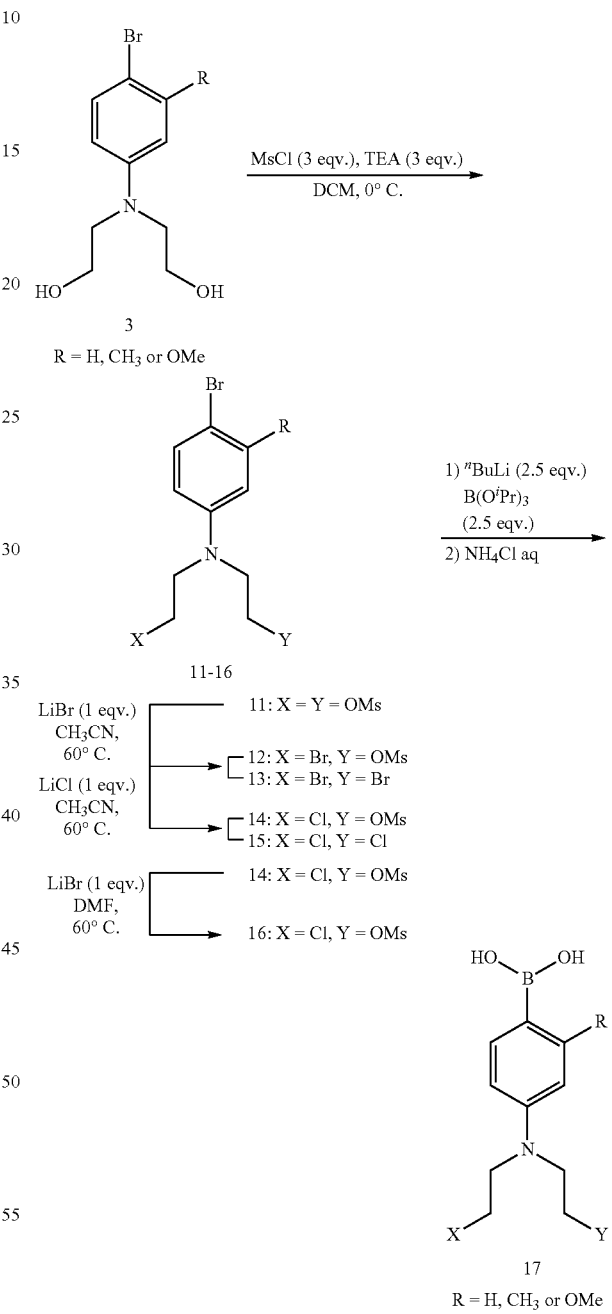

11a-16a (R=H) were prepared using the procedure described above in Example 1:11a (92% yield), 12a (22% yield), 13a (32% yield), 14a (30% yield), 15a (25% yield), 16a (95% yield). 15a (25% yield) $^1$H NMR (CDCl$_3$, 300 MHz): δ 3.62-3.66 (m, 4H), 3.71-3.76 (m, 4H), 6.60 (d, J=9.0 Hz, 2H), 7.35 (d, J=9.0 Hz, 2H); $^{13}$C NMR (CDCl$_3$, 75 MHz): δ 40.4, 53.5, 109.7, 113.8, 132.5, 145.2.

4-(bis(2-chloroethyl)amino)phenylboronic acid (17a, R=H)

A solution of 15a (600 mg, 2 mmol) in 20 mL dry THF was cooled to −78° C. under Ar, "BuLi (2 mL, 2.6 M in Hexane) was added slowly at the same temperature within 10 min. After stirred for 30 min, B(O$^i$Pr)$_3$ (940 mg, 5 mmol) was added, the mixture was allowed to warm to room temperature and stirred overnight, then quenched by NH$_4$Cl solution at 0° C. The mixture was exacted with CH$_2$Cl$_2$ and washed with water, dried over Na$_2$S$_4$ and concentrated in vacuo, the residue was purified by column chromatography (Hexane/Ethyl Acetate=1:1) to afford white solid 17a (200 mg, 38%). $^1$H NMR (DMSO-d$_6$+D$_2$O, 300 MHz): δ 3.68 (t, J=4.2 Hz, 4H), 3.76-3.85 (t, J=4.2 Hz, 4H), 6.68 (d, J=8.4 Hz, 2H), 7.57 (d, J=8.4 Hz, 2H); $^{13}$C NMR (DMSO-d$_6$, 75 MHz): δ 41.7, 52.3, 111.4, 136.2, 148.6.

N,N-bis(2-chloroethyl)-3-methyl-4-(4,4,5,5-tetramethyl-1,3,2-dioxaborolan-2-yl)aniline (17b, R=CH$_3$)

15b (1.3 g, 4.2 mmol) was dissolved in 20 mL dry THF, the mixture was cooled to −78° C. under Ar. "BuLi (2.6 M in hexane) (4.5 mL) was added within 10 min. After stirred for 30 min at the same temperature, B(O$^i$P)$_3$ (2.5 mL, 11 mmol) was added. The resulting mixture was allowed to warm to room temperature slowly. After stirred overnight, NH$_4$Cl solution was added slowly at 0° C., and exacted with ethyl acetate and washed with water, the mixture was dried over Na$_2$SO$_4$ followed by filtration. After the solvent was removed, pinacol (1.0 g), Na$_2$SO$_4$ (2.0 g) and 10 mL Et$_2$O were added, the mixture was stirred for 8 h. The residue was purified by column chromatography (Hexane/Ethyl Acetate=1:20) to afford oil 17b (35% for two steps). $^1$H NMR (CDCl$_3$, 300 MHz): δ 1.33 (s, 12H), 2.58 (s, 3H), 3.64 (t, J=6.3, 4H), 3.79 (t, J=6.9, 4H), 6.51-6.53 (m, 1H), 7.75 (d, J=9.3 Hz, 1H).

Example 3

Compound Synthesis

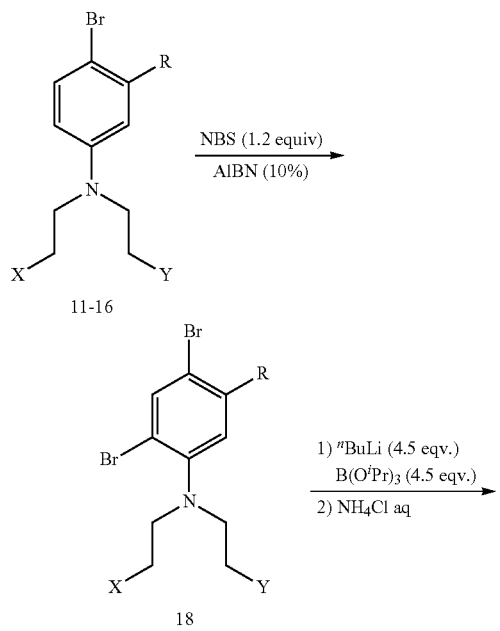

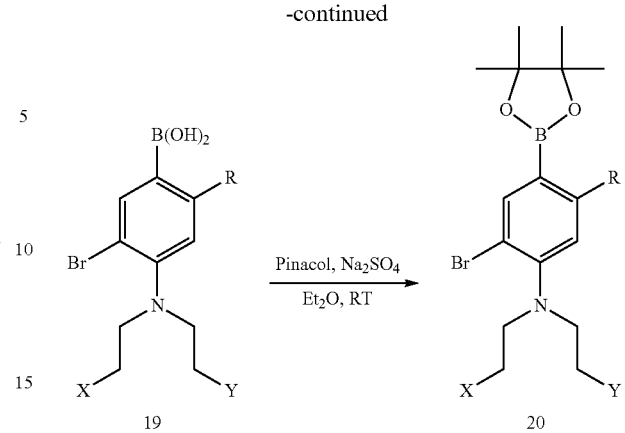

R = H, CH$_3$ or OMe
X = Cl, Br or OMs
Y = Cl, Br or OMs

2,4-dibromo-N,N-bis(2-chloroethyl)-5-methylaniline (18b, X=Y=Cl, R=CH$_3$)

15b (X=Y=Cl, R=CH$_3$) (6.1 g, 20 mmol), NBS (4.3 g, 24 mmol) and AIBN (330 mg, 2 mmol) were dissolved in CH$_3$CN (20 mL), after refluxed for 8 h, the mixture was exacted with EtOAc and washed with water, and the solvent was removed in vacuum, the residue was purified by column chromatography (Hexane/Ethyl Acetate=1:10) to afford white solid 18b (60% yield). $^1$H NMR (CDCl$_3$, 300 MHz): δ 2.36 (s, 3H), 3.48-3.52 (m, 8H), 7.13 (s, 1H), 7.76 (s, 1H).

2-bromo-N,N-bis(2-chloroethyl)-5-methyl-4-(4,4,5,5-tetramethyl-1,3,2-dioxaborolan-2-yl)aniline (19b, X=Y=Cl, R=CH$_3$)

18b (2.5 g, 6.5 mmol) was dissolved in 40 mL dry THF, the mixture was cooled to −78° C. under Ar. "BuLi (2.6 M in hexane) (8 mL) was added within 10 min. After stirred for 30 min at the same temperature, B(O$^i$P)$_3$ (4.3 mL, 19 mmol) was added. The resulting mixture was allowed to warm to room temperature slowly. After stirred overnight, NH$_4$Cl solution was added slowly at 0° C., and exacted with ethyl acetate and washed with water, the mixture was dried over Na$_2$SO$_4$ followed by filtration. After the solvent was removed, pinacol (1.0 g), Na$_2$SO$_4$ (2.0 g) and 10 mL Et$_2$O were added, the mixture was stirred for 8 h. The residue was purified by column chromatography (Hexane/Ethyl Acetate=1:20) to afford oil 19b (20% for two steps). $^1$H NMR (CDCl$_3$, 500

MHz): δ 1.34 (s, 12H), 2.52 (s, 3H), 2.98 (t, J=4.2, 2H), 3.47-3.53 (m, 4H), 3.68 (t, J=4.2, 2H), 6.29 (s, 1H), 7.52 (s, 1H).

Example 4

Compound Synthesis

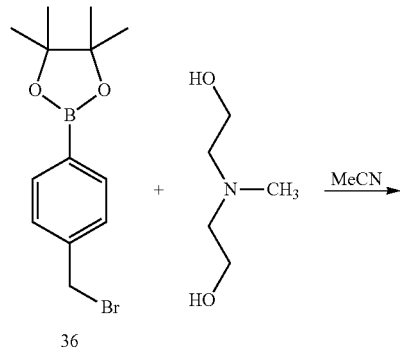

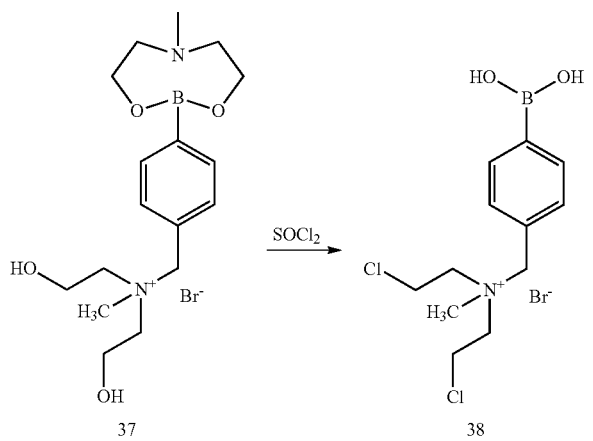

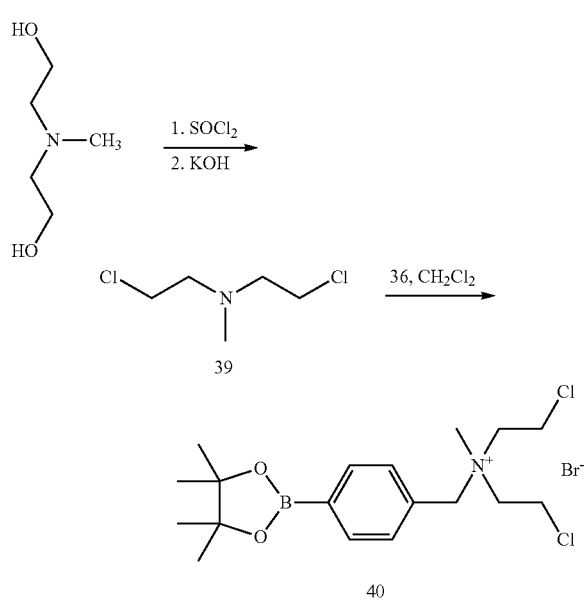

N,N-Bis(2-hydroxyethyl)-N-methyl-N-[4-(6-methyl-1,3,6,2-dioxazaborocan-2-yl)phenyl]methanaminium bromide (37)

A solution of 4-(bromomethyl)phenylboronic acid pinacol ester (0.3 g, 1 mmol) and N-methyldiethanolamine (0.36 g, 3 mmol) in anhydrous $CH_3$ CN (10 mL) was stirred at room temperature for overnight. After filtration, the product 37 was obtained as white solid (0.31 g, 75%). $^1$H NMR (DMSO-$d_6$, 300 MHz): δ 2.22 (s, 3H), 2.98 (s, 3H), 2.94-3.03 (m, 2H), 3.25-3.32 (m, 2H), 3.33-3.38 (m, 2H), 3.46-3.54 (m, 2H), 3.87-4.00 (m, 8H), 4.62 (s, 2H), 5.31 (t, J=4.8 Hz, 2H), 7.42 (d, J=7.8 Hz, 2H), 7.60 (d, J=7.8 Hz, 2H); $^{13}$C NMR (DMSO-$d_6$, 75 MHz): δ 134.0, 132.2, 126.8, 67.2, 63.0, 62.3, 60.3, 55.3, 48.6, 47.6. HRMS-ES (m/z) [M+H—Br]$^+$ calcd. for $C_{17}H_{31}BN_2O_4$, 337.2413. Found, 337.2161.

N,N-Bis(2-chloroethyl)-N-methyl-N-(4-boronophenyl)methanaminium bromide (38)

N,N-Bis(2-hydroxyethyl)-N-methyl-N-[4-(6-methyl-1,3,6,2-dioxazaborocan-2-yl)phenyl]methanaminium bromide (0.21 g, 0.5 mmol) was added in portion to thinoyl chloride, and stirred at r. t. for 4-5 days. The reaction solution was concentrated in vacuum at 20□. The residue was dispersed with EtOH/Et$_2$O, then filtered to yield 38 (0.12 g, 70%). $^1$H NMR (DMSO-$d_6$, 500 MHz): δ 3.07 (s, 3H), 3.63-3.69 (m, 2H), 3.79-3.82 (m, 2H), 4.13-4.20 (m, 4H), 4.71 (s, 2H), 7.52 (d, J=7.5 Hz, 2H), 7.91 (d, J=7.5 Hz, 2H), 8.24 (s, 2H); $^{13}$C NMR (DMSO-$d_6$, 75 MHz): δ 135.1, 132.6, 129.2, 66.1, 61.4, 47.9, 36.5; HRMS-ES (m/z) [M+H—Br]$^+$ calcd. for $C_{12}H_{20}BCl_2NO_2$, 290.1000. Found, 290.0861.

N,N-Bis(2-chloroethyl)-N-methyl-N-[4-(4,4,5,5-tetramethyl-1,3,2-dioxaborolan-2-yl)phenyl]methanaminium bromide (40)

A solution of N-methyldiethanolamine (3 g, 25 mmol) in $CH_2Cl_2$ (5 mL) was slowly added dropwise to thionyl chloride (10 mL) in ice-water bath, then stirred at r. t. for 2 days. After evaporated, the residue was dispersed with $CH_3$ CN/Et$_2$O, then was filtered to give N,N-bis(2-chloroethyl) methyl ammonium hydrochloride (4.1 g, 85%).

In a beaker are successively placed N,N-bis(2-chloroethyl) methyl ammonium hydrochloride (0.96 g, 5 mmol), ice (20 g) and potassium hydroxide (0.34 g, 5.5 mmol). The mixture was stirred for 5 min, then $CH_2Cl_2$ (20 mL) was added. The organic phase was washed in a separation funnel with water, and dried over anhydrous Na$_2$SO$_4$. After filtering and concentrating to a half volume, 4-(bromomethyl)phenylboronic acid pinacol ester (0.15 g, 0.5 mmol) was added into the organic phase, then stirred at r. t. for 3 days. After evaporation, the target product 40 was obtained as white powder (0.1 g, 45%). The filtrate was concentrated to recover material 4-(bromomethyl)phenylboronic acid pinacol ester (45 mg, 30%). $^1$H NMR (DMSO-$d_6$, 500 MHz): δ 3.09 (s, 3H), 3.65-3.70 (m, 2H), 3.82-3.87 (m, 2H), 4.16-4.20 (m, 4H), 4.79 (s, 2H), 7.60 (d, J=8.0 Hz, 2H), 7.80 (d, J=8.0 Hz, 2H); $^{13}$C NMR (DMSO-$d_6$, 75 MHz): δ 135.3, 133.1, 130.7, 84.5, 65.9, 61.5, 47.8, 36.5, 25.1; HRMS-ES (m/z) [M+H—Br]$^+$ calcd. for $C_{18}H_{30}BCl_2NO_2$, 372.1783. Found, 372.1582.

Example 5

Compound Synthesis

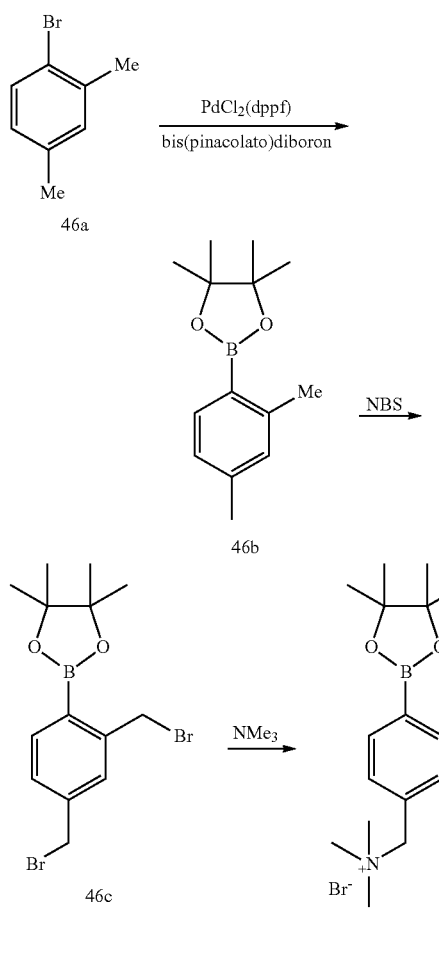

2-(2,4-Bismethylphenyl)-4,4,5,5-tetramethyl-[1,3,2]dioxaborolane (46b)

1-Bromo-2,4-dimethylbenzene (46a: 0.74 g, 4 mmol), bis(pinacolato)diboron (1.53 g, 6 mmol), KOAc (1.18 g, 12 mmol), and PdCl$_2$ (dppf) (98 mg, 0.12 mmol) were dissolved in DMF (40 mL) under argon atmosphere. The mixture was heated at 85° C. for 48 h, cooled and then water (100 mL) was added, and the mixture was extracted with CH$_2$Cl$_2$ (3×50 mL). The combined organic layer was washed with water and brine, and then dried over Na$_2$SO$_4$, filtrated, and the solvent was evaporated. The crude product was purified through column chromatography with 0-50% EtOAc in hexane to provide compound 46b as white solid (0.74 g, 80%). $^1$H NMR (300 MHz, CDCl$_3$) δ 1.34 (s, 12H), 2.32 (s, 3H), 2.52 (s, 3H), 7.90-7.03 (m, 2H), 7.66 (d, J=8.0 Hz, 1H); $^{13}$C NMR (500 MHz, CDCl$_3$) δ 145.0, 140.9, 136.1, 130.8, 125.6, 83.3, 24.9, 22.2, 21.5

2-(2,4-Bisbromomethylphenyl)-4,4,5,5-tetramethyl-[1,3,2]dioxaborolane (46c)

Compound 37b (0.83 g, 3.6 mmol) was dissolved in CH$_3$CN (55 mL), and NBS (1.6 g, 9 mmol) and AIBN (62.9 mg) were added. The mixture was refluxed at 90° C. for 3 h. Then the mixture was concentrated and dissolved in DCM (100 mL). The organic phase was washed with H$_2$O (3×50 mL) and dried with anhydrous Na$_2$SO$_4$. The solution was evaporated and the residue was subjected to column chromatography on silica gel with 0-50% DCM in hexane to give the desired product 46c as a white solid (0.7 g, 50%). $^1$H NMR (300 MHz, CDCl$_3$) δ 1.37 (s, 12H), 4.46 (s, 2H), 4.90 (s, 2H), 7.30 (d, J=7.7 Hz, 1H) 7.41 (s, 1H), 7.80 (d, J=7.7 Hz, 1H); $^{13}$C NMR (500 MHz, CDCl$_3$) δ 144.9, 140.8, 137.0, 130.5, 128.1, 84.0, 33.3, 32.7, 24.9; HRMS (EI) m/z Calcd for $C_{14}H_{19}BBr_2O_2$ [M]$^+$ 387.9845. Found 387.9829.

1,4-Di(trimethyl)-[2,5-di(4',4',5',5'-tetramethyl-[1',3',2']dioxaborolan-2'-yl)-benzyl]-ammonium bromide (46)

Compound 46c (0.182 g, 0.47 mmol) was suspended in CH$_3$CN (10 mL), and 4.2 M trimethylamine (0.34 mL, 1.41 mmol) in ethanol was added dropwise with stirring. The reaction mixture was stirred at rt for 12 h and concentrated resulting in 46 as a white solid (0.22 g, 93%). $^1$H NMR (300 MHz, DMSO) δ 1.36 (s, 12H), 3.09 (s, 18H), 4.66 (s, 2H), 4.84 (s, 2H), 7.70-7.76 (m, 2H), 8.00 (d, J=7.6 Hz, 1H); $^{13}$C NMR (500 MHz, DMSO) δ 137.7, 137.2, 134.1, 133.8, 131.7, 84.6, 66.8, 66.3, 52.3, 51.8, 24.5; HRMS (ESI) m/z Calcd for $C_{20}H_{37}BBr_2N_2O_2$ [(M−2Br)/2]$^+$ 174.1474. Found 174.1460.

Example 6

Compound Synthesis

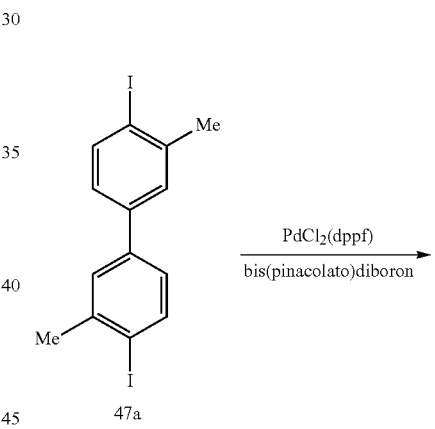

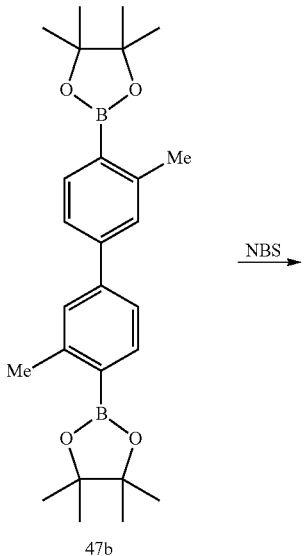

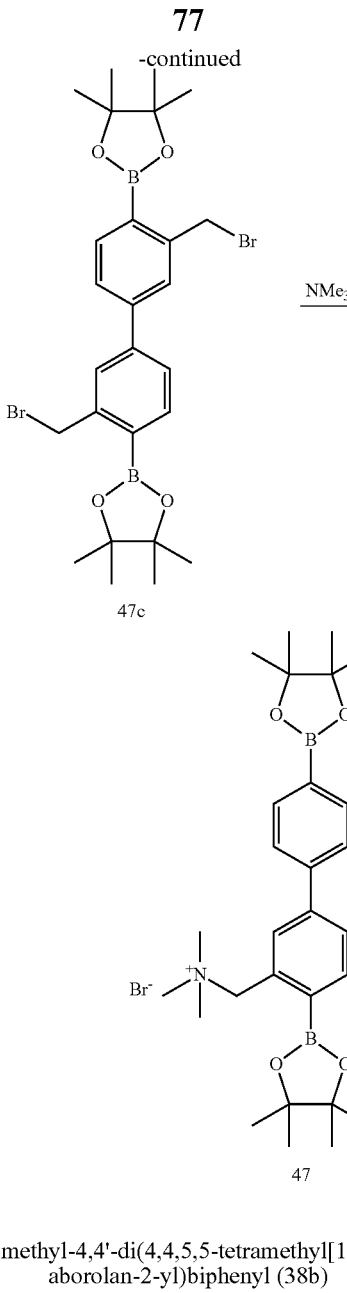

were added. The mixture was refluxed at 90° C. for 6 h. Then the mixture was concentrated and dissolved in DCM (100 mL). The organic phase was washed with H$_2$O (3×50 mL) and dried over anhydrous Na$_2$SO$_4$. The solution was evaporated and the residue was subjected to column chromatography on silica gel with 0-50% DCM in hexane to give the desired product 47c as a white solid (0.89 g, 50%). $^1$H NMR (300 MHz, CDCl$_3$) δ 1.39 (s, 24H), 4.98 (s, 4H), 7.50-7.54 (m, 2H), 7.62 (s, 1H), 7.87-7.91 (m, 2H); $^{13}$C NMR (500 MHz, CDCl$_3$) δ 145.0, 143.1, 137.1, 128.8, 126.3, 84.0, 33.9, 24.9.

3,3'-Di(trimethyl)-[4,4'-di(4,4,5,5-tetramethyl-[1,3,2] dioxaborolan-2-yl)-biphenyl]-ammonium bromide (47)

Compound 47c (0.1 g, 0.17 mmol) was suspended in CH$_3$CN (5 mL), and 4.2 M trimethylamine (0.12 mL, 0.51 mmol) in ethanol was added dropwise with stirring. The reaction mixture was stirred at rt for 12 h and concentrated resulting in 47 as a white solid (0.12 g, 99%). $^1$H NMR (300 MHz, DMSO) δ 1.37 (s, 24H), 3.10 (s, 18H), 4.87 (s, 4H), 7.90-8.08 (m, 6H); $^{13}$C NMR (500 MHz, DMSO) δ 141.6, 137.6, 134.6, 132.3, 127.9, 84.5, 66.6, 52.4, 24.5; HRMS (ESI) m/z Calcd for C$_{32}$H$_{52}$B$_2$Br$_2$N$_2$O$_4$ [(M−2Br)/2]$^+$275.2056. Found 275.1998.

Example 7

Compound Synthesis

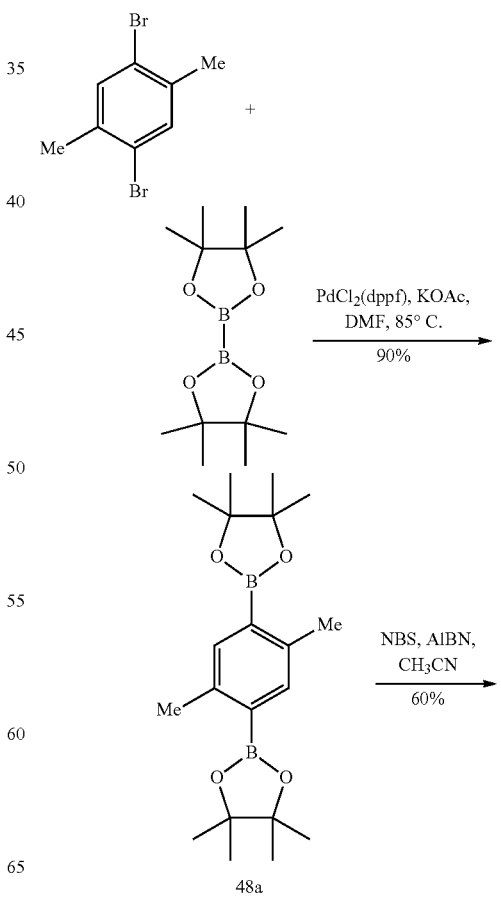

3,3'-Dimethyl-4,4'-di(4,4,5,5-tetramethyl[1,3,2]dioxaborolan-2-yl)biphenyl (38b)

4,4'-Diiodo-3,3'-dimethylbiphenyl 47a (4.34 g, 10 mmol), bis(pinacolato)diboron (7.62 g, 30 mmol), and PdCl2(dppf) (490 mg, 0.6 mmol) were dissolved in DMF (100 mL) under argon atmosphere. The mixture was heated at 85° C. for 48 h, cooled and then water (200 mL) was added. The mixture was extracted with CH$_2$Cl$_2$ (3×100 mL). The combined organic layer was washed with water and brine, dried over Na$_2$SO$_4$, filtrated, and the solvent was evaporated. The crude product was purified through column chromatography with 0-50% EtOAc in hexane to provide compound 47b as white solid (3.91 g, 90%). $^1$H NMR (300 MHz, CDCl$_3$) δ 1.38 (s, 24H), 2.64 (s, 6H), 7.35-7.46 (m, 2H), 7.80-7.90 (m, 1H); $^{13}$C NMR (500 MHz, CDCl$_3$) δ 145.4, 143.3, 136.5, 128.6, 123.6, 83.5, 24.9, 22.4.

3,3'-Dibromomethyl-4,4'-di(4,4,5,5-tetramethyl[1,3,2]dioxaborolan-2-yl)biphenyl (47c)

Compound 47b (1.31 g, 3 mmol) was dissolved in CH$_3$CN (45 mL), and NBS (1.34 g, 7.5 mmol) and AIBN (52.4 mg)

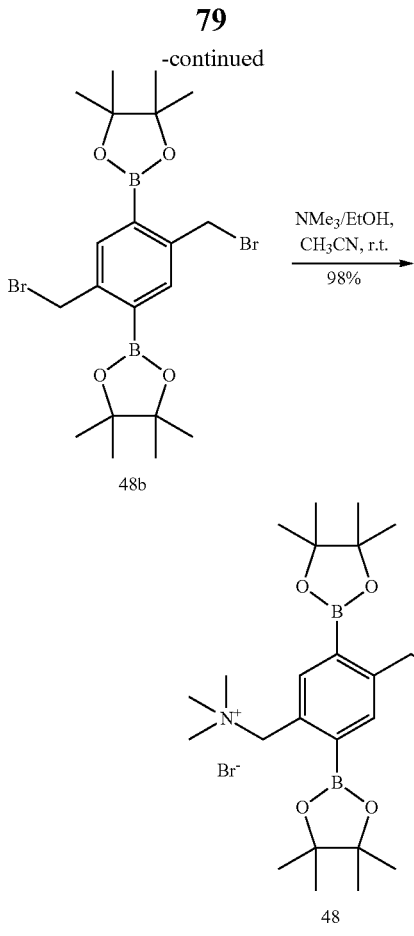

1,4-Dimethyl-2,5-di(4',4',5',5'-tetramethyl[1',3',2']dioxaborolan-2'-yl)benzene (48a)

2,5-dibromo-p-xylene (1.06 g, 4 mmol), bis(pinacolato)diboron (3.05 g, 12 mmol), KOAc (2.36 g, 24 mmol), and PdCl$_2$(dppf) (196 mg, 0.24 mmol) were dissolved in DMF (40 mL) under argon atmosphere. The mixture was heated at 85° C. for 48 h, cooled and then water (100 ml) was added, the mixture was extracted with CH$_2$Cl$_2$(3×50 ml). The combined organic layer was washed with water and brine, and then dried over Na$_2$SO$_4$, and the solvent was evaporated. The crude product was purified through column chromatography with 0-50% EtOAc in hexane to provide compound 48a as white solid (1.28 g, 90%). $^1$H NMR (300 MHz, CDCl$_3$) δ 1.39 (s, 24H), 2.51 (s, 6H), 7.57 (s, 2H); $^{13}$C NMR (500 MHz, CDCl$_3$) δ 140.58, 136.94, 83.43, 24.91, 21.52.

1,4-Dibromomethyl-2,5-di(4',4',5',5'-tetramethyl[1',3',2']dioxaborolan-2'-yl)benzene (48b)

Compound 48a (1.08 g, 3 mmol) was dissolved in CH$_3$CN (45 mL), and NBS (1.34 g, 7.5 mmol) and AIBN (52.4 mg) were added. The mixture was refluxed at 90° C. for 6 h. Then the mixture was concentrated and dissolved in DCM (100 ml). The organic phase was washed with H$_2$O (3×50 ml) and dried with anhydrous Na$_2$SO4. The solution was evaporated and the residue was subject to column chromatography on silica gel with 0-50% DCM in hexane to give the desired product 48b as a white solid (0.71 g, 60%). $^1$H NMR (300 MHz, CDCl$_3$) δ 1.38 (s, 24H), 4.88 (s, 4H), 7.79 (s, 2H); $^{13}$C NMR (500 MHz, CDCl$_3$) δ 143.36, 137.85, 84.13, 33.43, 24.90.

1,4-Di-trimethyl-[2,5-di(4',4',5',5'-tetramethyl-[1',3',2']dioxaborolan-2'-yl)-benzyl]-ammonium bromide (48)

Compound 48b (0.1 g, 0.19 mmol) was suspended in CH$_3$CN (5 ml), and 4.2 M trimethylamine (0.14 ml, 0.57 mmol) in ethanol was added dropwise with stirring. The reaction mixture was concentrated after 12 h at rt and gave 48 as white solid (0.12 g, 95%). $^1$H NMR (300 MHz, DMSO) δ 1.35 (s, 24H), 3.05 (s, 18H), 4.86 (s, 4H), 8.02 (s, 2H). $^{13}$C NMR (500 MHz, DMSO) δ 141.57, 134.66, 84.76, 65.84, 52.10, 24.49; HRMS (ESI) m/z Calcd for C$_{26}$H$_{48}$B$_2$Br$_2$N$_2$O$_4$ [(M−2Br)/2]$^+$ 237.1900. Found 237.1862.

Example 8

Compound Synthesis

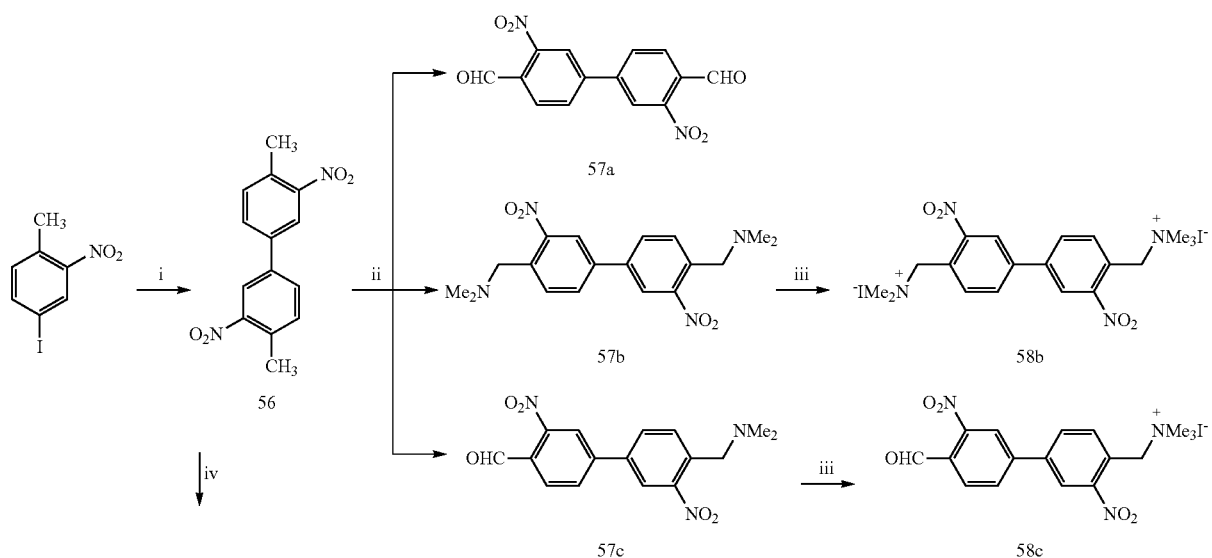

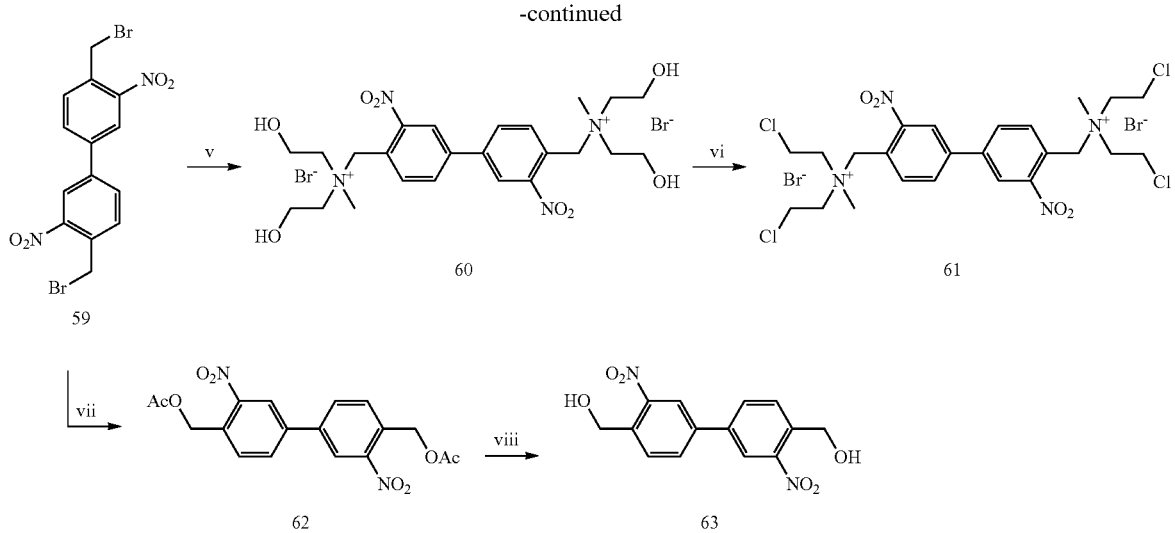

Reagents and conditions: i) PdCl$_2$ (dppf), K$_2$ CO$_3$, bis(pinacolato)diboron, DMSO, 85° C., 3 h, 90%; ii) a) NBS, AIBN, CH$_3$ CN, reflux overnight; b) Me$_2$ NH, r. t. overnight, 3% for 57a, 55% for 57b and 15% for 57c; iii) MeI, CH$_2$Cl$_2$, r. t. 24 h, 85% for 58b and 70% for 58c; iv) NBS, AIBN, CH$_3$ CN, reflux 8 h, 65%; v) N-methyldiethanolamine, CH$_3$ CN, reflux 20 h, 85%; vi) SOCl$_2$, r. t., 3 days, 74%; vii) KOAc, DMF, 70° C., 6 h, 88%; viii) 10% KOH, reflux 24 h, 50%.

3,3'-Dinitroditoluene (56)

To a oven-dried Schlenk tube was added 4-iodo-2-nitrotoluene (1.97 g, 7.5 mmol), catalyst PdCl2(dppf).CH$_2$Cl$_2$ (0.31 g, 0.38 mmol), anhydrous potassium carbonate (3.11 g, 22.5 mmol) and bis(pinacolato)diboron (0.95 g, 3.75 mmol). Anhydrous DMSO (40 mL) was added into the mixture, and the resulted solution was stirred at 85° C. for 3 h under argon. The reaction solution was cooled to room temperature, and added H$_2$O and EtOAc. The combined organic phase was washed with H$_2$O and brine, respectively. After evaporation, the crude product was purified by flash chromatography (elute hexane/EtOAc: 10/1) to afford 2 (1.84 g, 90%) as white solid. $^1$H NMR (CDCl$_3$, 300 MHz): δ 8.24 (d, J=1.5 Hz, 2H), 7.60 (dd, J=7.95, 1.65 Hz, 2H), 7.50 (d, J=7.95 Hz, 2H), 2.68 (s, 6H).

N,N-Dimethyl-o-nitrobenzylamine dimer (57b)

The reaction mixture of 56 (0.544 g, 2 mmol), N-bromosuccinimide (0.9 g, 5 mmol) and AIBN (21.8 mg) in anhydrous CH$_3$ CN (20 mL) was refluxed for 3 h, then added more N-bromosuccinimide (0.53 g, 3 mmol) and AIBN (13 mg). The reaction was continuously refluxed overnight. After cooled to 0° C., a solution of Me$_2$ NH in THF (2M, 10 mL, 20 mmol) was added dropwise and stirred overnight at r. t. The residue removed solvent in vacuo was dissolved with CH$_2$Cl$_2$ and washed with sat. aq. NaHCO$_3$, brine, respectively, and dried over anhydrous Na$_2$SO$_4$. After removing solvent, the crude product was purified by flash column chromatography (gradient elution, CH$_2$Cl$_2$/Me$_2$CO: 10/1→5/1→3/1) to yield compound 57a (18 mg, 3%), 57b (0.4 g, 55%) and 57c (0.1 g, 15%).

N,N-Dimethyl-o-nitrobenzaldehyde dimer (57a)

$^1$H NMR (DMSO-d$_6$, 300 MHz): δ10.28 (s, 2H), 8.64 (d, J=1.8 Hz, 2H), 8.42 dd, J=8.1, 1.8 Hz, 2H), 8.09 (d, J=8.1 Hz, 2H).

N,N-Dimethyl-o-nitrobenzylamine dimer (57b)

$^1$H NMR (CDCl$_3$, 300 MHz): δ 8.10 (d, J=1.2 Hz, 2H), 7.81 (dd, J=8.1, 1.5 Hz, 2H), 7.77 (d, J=8.1 Hz, 2H), 3.78 (s, 4H), 2.29 (s, 12H).

N,N-Dimethyl-2-nitro-4-(3-nitro-4-formylphenyl)benzylamine (57c)

$^1$H NMR (CDCl$_3$, 300 MHz): δ 10.50 (s, 1H), 8.36 (d, J=1.5 Hz, 1H), 8.17 (s, 1H), 8.13 (d, J=8.0 Hz, 1H), 8.05 (d, J=8.0 Hz, 1H), 7.87 (d, J=1.2 Hz, 2H), 3.82 (s, 2H), 2.30 (s, 6H). $^{13}$C NMR (CDCl$_3$, 75 MHz) δ 187.5, 150.3, 150.2, 144.3, 137.3, 135.9, 132.3, 132.0, 130.9, 130.7, 130.2, 123.1, 122.8, 57.0, 45.7

N,N,N-trimethyl-o-nitrophenylmethanaminium iodide dimer (58b)

The mixture of 57b (0.18 g, 0.5 mmol) and iodomethane (0.71 g, 5 mmol) in anhydrous CH$_2$Cl$_2$ (5 mL) was stirred for 12 h at r. t., then added additional iodomethane (0.71 g, 5 mmol) and continuously stirred for 12 h. After evaporation, the residue was dispensed with CH$_2$Cl$_2$ and filtered to give 58b (0.27 g, 84%) as yellow solid.

The compound 58c was synthesized using the same procedure in 70% yield.

1-(Bromomethyl)-2-nitrobenzene dimer (59)

The reaction mixture of 56 (0.544 g, 2 mmol), N-bromosuccinimide (0.9 g, 5 mmol) and AIBN (21.8 mg) in anhydrous CH$_3$ CN (20 mL) was refluxed for 3 h, then added more N-bromosuccinimide (0.53 g, 3 mmol) and AIBN (13 mg). The reaction was continuously refluxed 5 h. After cooled to r. t. and concentrated, the residue was purified by flash column chromatography (elution, hexane/EtOAc 5/1) to yield compound 59 (0.6 g, 65%) as yellow solid.

N,N-Bis(2-hydroxyethyl)-N-methyl-N-(2-nitrophenyl)methanaminium bromide dimer (60)

The mixture of 1-(bromomethyl)-2-nitrobenzene dimer 59 (0.1 g, 0.23 mmol) and N-methyldiethanolamine (0.14 g, 1.2 mmol) in anhydrous acetonitrile (5 mL) was stirred under reflux for 20 h, and cooled to r. t. The precipitate was filtered and washed with anhydrous acetonitrile to afford compound 60 (0.133 g, 85%) as white solid.

N,N-Bis(2-chloroethyl)-N-methyl-N-(2-nitrophenyl)methanaminium bromide dimer (61)

Thionyl chloride was added dropwise to compound 60 (0.68 g, 1 mmol) with stirring under argon at ice-bath. The mixture was stirred at r. t. for 3 days. Removing thionyl chloride in vacuum, the residue was dispensed with cold ethanol and evaporated to remove thionyl chloride as much as possible. The crude solid was washed with EtOH/Et$_2$O (1/1) and filtered. The target product 61 (0.55 g, 74%) was obtained as white solid.

2-Nitrobenzyl acetate dimer (62)

The mixture of 1-(bromomethyl)-2-nitrobenzene dimer 59 (0.43 g, 1 mmol) and potassium acetate (0.4 g, 4 mmol) in anhydrous DMF (40 mL) was stirred at 70° C. for 6 h, and cooled to r. t. After evaporation, the residue was dispensed with ice-water, and extracted with EtOAc. The combined organic phase was washed with H$_2$O, brine, respectively, and dried over anhydrous Na$_2$SO$_4$. After removing solvent, the crude product was purified by flash column chromatography (elution, hexane/EtOAc:3/1) to yield compound 62 (0.34 g, 88%) as white solid.

2-Nitrophenyl methanol dimer (63)

To a suspension of compound 62 (70 mg, 0.18 mmol) in H$_2$O (10 mL) was added 10% aq. KOH solution (0.5 mL). The reaction mixture was heated under reflux for 24 h. The reaction solution was cooled to r. t., and adjusted to pH 7 with 1 M HCl, then concentrated to half volume. The solution was kept at 0° C. for 2 h, and filtered. The crude precipitate was purified by silica gel column (elute hexane/EtOAc:1/1) to afford 63 (27 mg, 50%) as white solid.

Example 9

Compound Synthesis

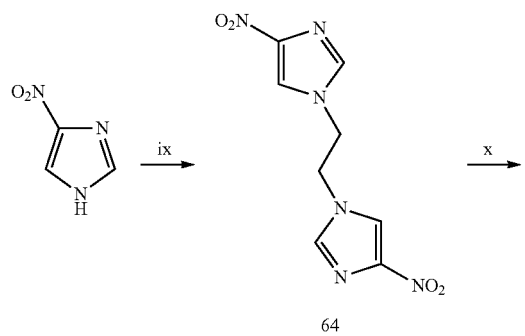

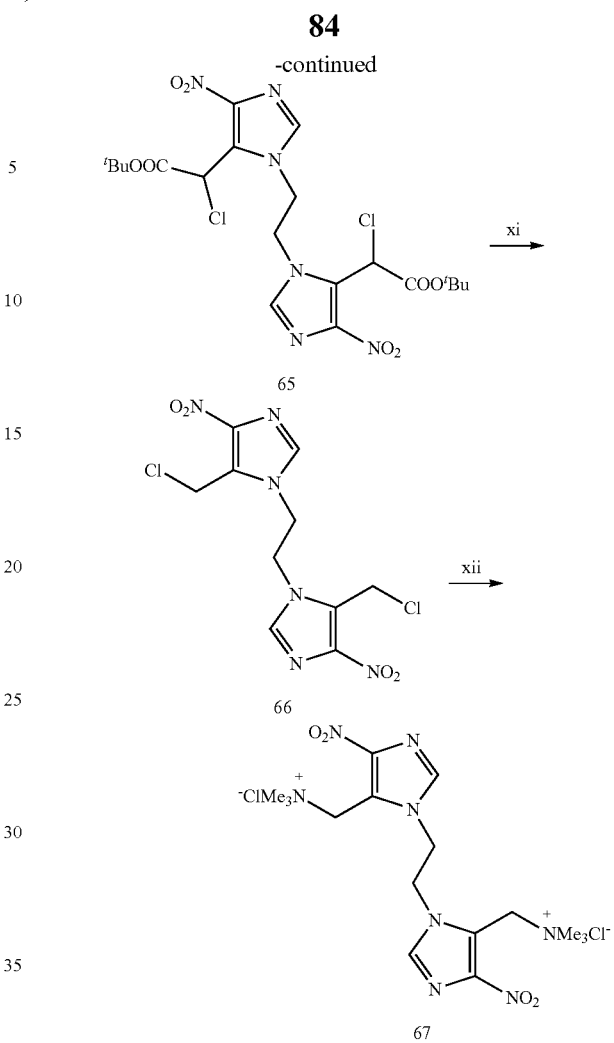

Reagents and conditions: ix) BrCH$_2$CH$_2$Br, t-BuOK, DMF, r. t. 3 days, 45%; x) Cl$_2$CHCOO$^t$Bu, t-BuOK, DMF, −25° C., 1 h, 30%; xi) HOAc, reflux, 4 h, 70%; xii) Me$_3$N, EtOH, 40° C., 24 h, 60%.

4-Nitro-1-(2-(4-nitro-1H-imidazol-1-yl)ethyl)-1H-imidazole (64)

$^t$BuOK (5 g, 44 mmol) was added in portions to a suspension of 4-nitroimidazole in anhydrous DMF (100 mL) at 0° C., then the reaction mixture was stirred at r. t. for 3 h, a solution of 1,2-dibromoethane in anhydrous DMF (20 mL) was added into the above mixture. The reaction solution was stirred at r. t. for 3 days, and was poured into ice-water (200 mL) for standing up for 2 h, then filtered. The filtered cake was washed with EtOH/CH$_2$Cl$_2$ (1/1) and dried to provide 64 (2.3 g, 45%) as off-white solid, which was pure enough to be used next step.

5-(tert-butoxycarbonylchloromethyl)-1-(2-(tert-butoxycarbonylchloromethyl)-4-nitro-1H-imidazol-1-yl)ethyl)-4-nitro-1H-imidazole (65)

To a stirred solution of $^t$BuOK (0.7 g, 6 mmol) in anhydrous DMF (10 mL) was added dropwise a suspension of compound 64 (0.252 g, 1 mmol) and tert-butyl 2,2,-dichloroacetate (0.56 g, 3 mmol) in anhydrous DMF (50 mL) under nitrogen keeping temperature at −25° C. The deep purple solution was stirred at −25° C. for further 1 h, then poured into cold HCl (0.5 M, 20 mL), and extracted with EtOAc. The combined organic phase was washed with H₂O, brine, respectively, dried over anhydrous Na₂SO₄. After removing solvent, the crude product was purified by chromatography (elution, CH₂Cl₂/EtOAc: 25/1) to yield compound 65 (0.17 g, 30%) as white solid.

5-(Chloromethyl)-1-(2-(5-(chloromethyl)-4-nitro-1H-imidazol-1-yl)ethyl)-4-nitro-1H-imidazole (66)

A mixture of compound 65 (1.54 g, 3 mmol) in acetic acid (25 mL) was refluxed for 4 h under nitrogen. After evaporation in vacuo, the residue was purified by silica gel column (elution, CH₂Cl₂/MeOH: 15/1) to provide compound 66 (0.73 g, 70%) as pale-yellow solid.

5-(N,N,N-trimethylmethanaminium iodide)-1-(2-(5-(N,N,N-trimethyl methanaminium iodide)-4-nitro-1H-imidazol-1-yl)ethyl)-4-nitro-1H-imidazole (67)

Trimethylamine solution in EtOH (0.7 mL, 4.2 M, 3 mmol) was added dropwise into a suspension of compound 66 (0.174 g, 0.5 mmol) in anhydrous EtOH (5 mL), and stirred at 40° C. for 24 h. The crude product removed solvent was dispensed with dichloromethane, then filtered to afford compound 67 (0.14 g, 60%) as a pale-yellow solid. 13 (0.14 g, 60%) as pale-yellow solid.

Example 10

Compound Synthesis

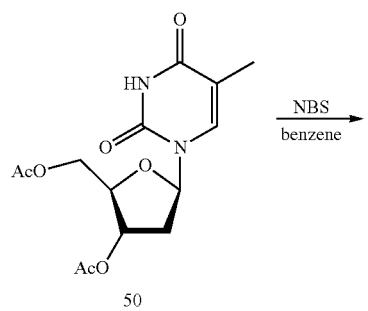

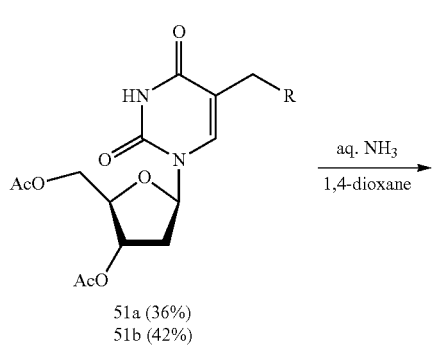

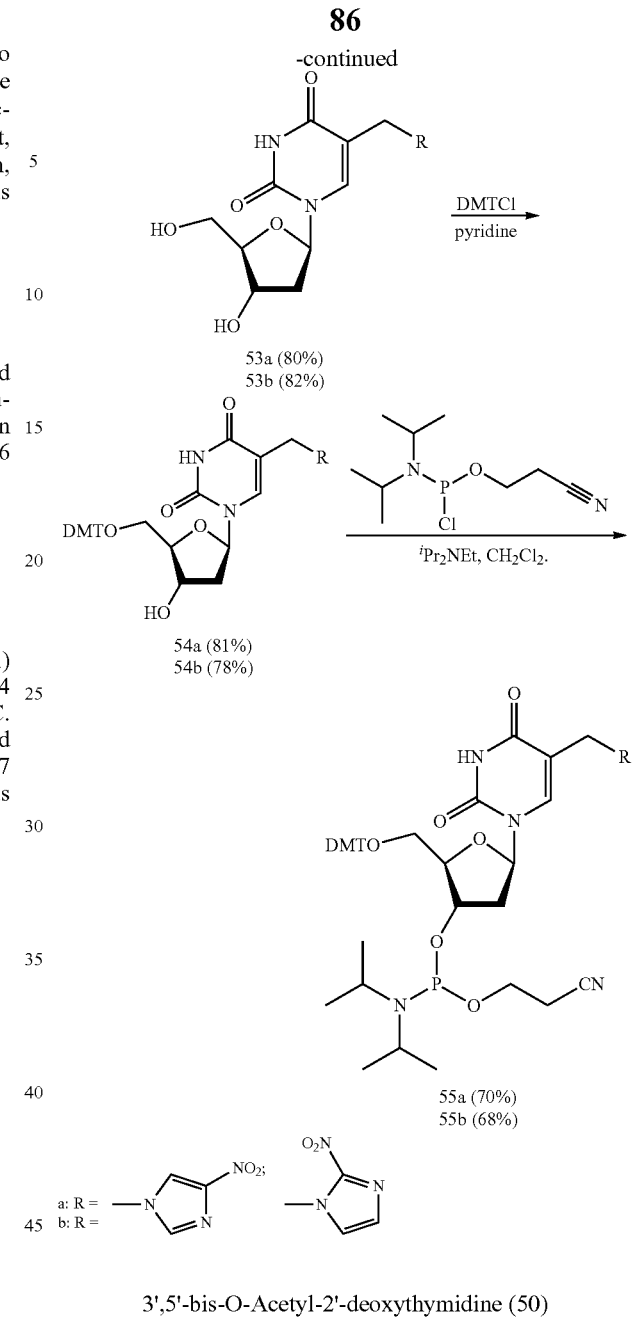

3',5'-bis-O-Acetyl-2'-deoxythymidine (50)

Into a solution of thymidine (4.84 g, 20 mmol) in anhydrous pyridine (50 mL), acetic anhydride (5.66 mL, 60 mmol) was added dropwise at 0° C., and then the reaction mixture was stirred for overnight at room temperature. After evaporation, the residue was dissolved in EtOAc, and was washed with H₂O, 1 M HCl, H₂O and brine, respectively, then dried over anhydrous Na₂SO₄. After removing solvent, the crude product was purified by silica gel column (EtOAc/Hexane:3/1) to give compound 50 as a colorless solid (5.8 g, 90%). ¹H NMR (CDCl₃, 300 MHz): δ 1.96 (s, 3H), 2.13 (s, 3H), 2.15 (s, 3H), 2.18-2.23 (m, 1H), 2.45-2.53 (m, 1H), 4.25-4.28 (m, 1H), 4.36-4.39 (m, 2H), 5.22-5.25 (m, 1H), 6.35 (dd, J=5.4, 8.4 Hz, 1H), 7.29 (s 1H), 9.08 (s 1H).

3',5'-bis-O-Acetyl-5-(4-nitro-1H-imidazol-1-yl)methyl-2'-deoxythymidine (51a)

The mixture of compound 50 (1.63 g, 5 mmol), N-bromosuccinimide (1.07 g, 6 mmol) and catalytic amount AIBN (81.5 mg) was refluxed for 3 h, then added additional N-bromosuccinimide (0.53 g, 3 mmol) and catalytic amount AIBN (20 mg). The reaction mixture was continuously refluxed for another 3 h, and then cooled to room temperature. After evaporation, the dark brown residue was diluted with anhydrous DMF (20 mL), and added dropwise to a mixture of 4-nitroimidazole (0.56 g, 5 mmol) and 60% NaH (0.24 g, 6 mmol) in anhydrous DMF (20 mL). The reaction solution was stirred at r. t. overnight. After evaporating solvent, the residue was purified by chromatography ($CH_2Cl_2$/MeOH: 30/1) to afford 51a (0.80 g, 36%) as a pale-yellow foam. $^1$H NMR ($CDCl_3$, 300 MHz): δ 2.15 (s, 3H), 2.17 (s, 3H), 2.10-2.20 (m, 1H), 2.52-2.68 (m, 1H), 4.24-4.40 (m, 2H), 4.35-4.8 (m, 1H), 4.86-5.32 (m, 3H), 6.27-6.32 (m, 1H), 7.72 (d, J=1.5 Hz, 1H), 8.03 (s 1H), 8.10 (d, J=1.5 Hz, 1H), 9.26 (s 1H); $^{13}$C NMR ($CDCl_3$, 75 MHz): δ 171.4, 170.3, 162.2, 149.5, 143.6, 139.9, 136.6, 133.9, 119.9, 109.0, 86.2, 83.4, 73.7, 63.3, 44.3, 37.9, 21.0; HRMS-ES (m/z) [M+H]$^+$ calcd. for $C_{17}H_{20}N_5O_9$, 438.1261. Found, 438.1271.

3',5'-bis-O-Acetyl-5-(2-nitro-1H-imidazol-1-yl)methyl-2'-deoxythymidine (51b)

The mixture of compound 50 (1.63 g, 5 mmol), N-bromosuccinimide (1.07 g, 6 mmol) and catalytic amount AIBN (81.5 mg) was refluxed for 3 h, then added additional N-bromosuccinimide (0.53 g, 3 mmol) and catalytic amount AIBN (20 mg). The reaction mixture was continuously refluxed for another 3 h, and then cooled to room temperature. After evaporation, the dark brown residue was diluted with anhydrous DMF (20 mL), and added dropwise to a mixture of 2-nitroimidazole (0.56 g, 5 mmol) and 60% NaH (0.24 g, 6 mmol) in anhydrous DMF (20 mL). The reaction solution was stirred at r. t. overnight. After evaporating solvent, the residue was purified by chromatography ($CH_2Cl_2$/MeOH: 30/1) to yield 51b (0.93 g, 42%) as a pale-yellow foam. $^1$H NMR ($CDCl_3$, 300 MHz): δ 2.13 (s, 3H), 2.18 (s, 3H), 2.15-2.23 (m, 1H), 2.49-2.56 (m, 1H), 4.28-4.35 (m, 2H), 4.45-4.52 (m, 1H), 5.24-5.26 (m, 2H), 5.29-5.31 (m, 1H), 6.29 (dd, J=5.4, 8.7 Hz, 1H), 7.12 (s, 1H), 7.55 (s 1H), 8.03 (s, 1H), 9.53 (s 1H); $^{13}$C NMR ($CDCl_3$, 75 MHz): δ 170.6, 170.3, 162.8, 149.7, 144.3, 140.9, 128.5, 128.1, 108.4, 85.4, 82.7, 74.1, 63.8, 45.9, 37.8, 20.9; HRMS-ES (m/z) [M+Na]$^+$ calcd. for $C_{17}H_{19}N_5O_9Na$, 460.1081. Found, 460.1053.

5-(4-nitro-1H-imidazol-1-yl)methyl-2'-deoxythymidine (53a)

A solution of compound 51a (0.31 g, 0.7 mmol) in 28% ammonium hydroxide (6 mL) and 1,4-dioxane (4 mL) was stirred at r. t. for 24 h, then the solvent was removed under vacuum. The residue was subjected to silica gel column ($CH_2Cl_2$/MeOH/Et$_3$N: 50/5/1) to provide 53a (0.2 g, 80%) as a white solid. $^1$H NMR (DMSO-d$_6$, 300 MHz): δ 2.14-2.26 (m, 2H), 3.56-3.61 (m, 2H), 3.79 (d, J=3.6 Hz, 1H), 4.25 (t, J=3.9 Hz, 1H), 4.84-5.02 (m, 3H), 5.26 (d, J=3.9 Hz, 1H), 6.12 (t, J=6.3 Hz, 1H), 7.85 (s, 1H), 8.10 (s, 1H), 8.33 (s 1H), 11.56 (brs 1H); $^{13}$C NMR (DMSO-d$_6$, 125 MHz): δ 163.2, 150.7, 147.3, 141.6, 137.8, 121.9, 108.0, 88.0, 85.0, 70.5, 61.6, 44.7; HRMS-ES (m/z) [M+H]$^+$ calcd. for $C_{13}H_{16}N_5O_7$, 354.1050. Found, 354.1077; [M+Na]$^+$ calcd. for $C_{13}H_{15}N_5O_7Na$, 376.0869. Found, 376.0867.

5-(2-nitro-1H-imidazol-1-yl)methyl-2'-deoxythymidine (53b)

A solution of compound 51b (0.31 g, 0.7 mmol) in 28% ammonium hydroxide (6 mL) and 1,4-dioxane (4 mL) was stirred at r. t. for 24 h, then the solvent was evaporated under vacuum. The residue was subjected to silica gel column ($CH_2Cl_2$/MeOH/Et$_3$N: 50/5/1) to afford 53b (0.21 g, 82%) as a white solid. $^1$H NMR (DMSO-d$_6$, 300 MHz): δ 2.10-2.14 (m, 2H), 3.53-3.57 (m, 2H), 3.78-3.81 (m, 1H), 4.22-4.24 (m, 1H), 4.92-4.96 (m, 1H), 5.16-5.29 (m, 3H), 6.13 (t, J=6.6 Hz, 1H), 7.15 (s, 1H), 7.62 (s, 1H), 8.00 (s 1H), 11.01 (brs 1H); $^{13}$C NMR (DMSO-d$_6$, 125 MHz): δ 163.1, 150.6, 145.1, 141.2, 128.3, 127.9, 107.9, 88.0, 85.0, 70.8, 61.7, 46.4; HRMS-ES (m/z) [M−H]$^−$ calcd. for $C_{13}H_{14}N_5O_7$, 352.0893. Found, 352.0874; [M+Cl]$^−$ calcd. for $C_{13}H_{15}N_5O_7Cl$, 388.0660. Found, 388.0643.

5'-O-(4,4'-Dimethoxytriphenylmethyl)-5-(4-nitro-1H-imidazol-1-yl)methyl-2'-deoxy thymidine (54a)

Compound 53a (0.3 g, 0.85 mmol) was co-evaporated with anhydrous pyridine (3×5 mL) and then dissolved in pyridine (5 mL). To the solution 4,4'-dimethoxytriphenylmethyl chloride (0.37 g 1.1 mmol) was added, and the reaction mixture was stirred at r. t. for 8 h. The reaction was quenched with MeOH (5 mL) and was concentrated in vacuo. The crude product was purified by flash chromatography ($CH_2Cl_2$/MeOH/Et$_3$N: 30/1/1) to give 54a (0.45 g, 81%) as a off-white solid. $^1$H NMR (DMSO-d$_6$, 300 MHz): δ 2.21-2.27 (m, 1H), 2.34-2.40 (m, 1H), 3.33 (s, 2H), 3.71 (s, 6H), 3.88-3.90 (m, 1H), 4.31-4.43 (m, 2H), 4.64 (d, J=13.6 Hz, 1H), 5.35 (d, J=4.5 Hz, 1H), 6.20 (t, J=6.3 Hz, 1H), 6.85 (d, J=9.0 Hz, 4H), 7.17-7.38 (m, 9H), 7.72 (s, 1H), 7.94 (s, 1H), 8.22 (s, 1H), 11.61 (s, 1H); $^{13}$C NMR (DMSO-d$_6$, 125 MHz): δ 162.8, 158.3, 149.8, 144.8, 141.6, 135.7, 129.9, 128.1, 127.0, 124.1, 121.4, 113.4, 107.5, 85.9, 85.6, 84.6, 70.3, 64.0, 55.2; HRMS-ES (m/z) [M−H]$^−$ calcd. for $C_{34}H_{32}N_5O_9$, 654.2200. Found, 654.2192.

5'-O-(4,4'-Dimethoxytriphenylmethyl)-5-(2-nitro-1H-imidazol-1-yl)methyl-2'-deoxy thymidine (54b)

Compound 53b (0.3 g, 0.85 mmol) was co-evaporated with anhydrous pyridine (3×5 mL) and then dissolved in pyridine (5 mL). To the solution 4,4'-dimethoxytriphenylmethyl chloride (0.37 g 1.1 mmol) was added, and the reaction mixture was stirred at r. t. for 15 h. The reaction was quenched with MeOH (5 mL) and was concentrated in vacuo. The crude product was purified by flash chromatography ($CH_2Cl_2$/MeOH/Et$_3$N: 30/1/1) to provide 54b (0.34 g, 78%) as a pale-yellow solid. $^1$H NMR (DMSO-d$_6$, 300 MHz): δ 2.21-2.30 (m, 1H), 2.42-2.51 (m, 1H), 3.51-3.53 (m, 2H), 3.80 (s, 6H), 4.04-4.09 (m, 1H), 4.47-4.52 (m, 1H), 4.83 (s, 2H), 6.30 (t, J=6.0 Hz, 1H), 6.85 (d, J=8.7 Hz, 4H), 7.07 (s, 1H), 7.20-7.35 (m, 8H), 7.44 (d, J=7.5 Hz, 2H), 8.01 (s, 1H); $^{13}$C NMR (DMSO-d$_6$, 125 MHz): 6162.4, 158.7, 149.5, 144.4, 141.5, 135.4, 130.2, 128.0, 127.7, 127.1, 113.3, 107.4, 87.0, 85.9, 85.3, 71.6, 63.5, 55.2; HRMS-ES (m/z) [M−H]$^−$ calcd. for $C_{34}H_{32}N_5O_9$, 654.2200. Found, 654.2207; [M+Cl]$^−$ calcd. for $C_{34}H_{33}N_5O_9Cl$, 690.1967. Found, 690.1930.

5'-O-(4,4'-Dimethoxytriphenylmethyl)-5-(4-nitro-1H-imidazol-1-yl)methyl-2'-deoxy uridine-3'-(2-cyanoethyl)-N,N-diisopropylphosphoramidite (55a)

To a solution of 54a (0.2 g, 0.31 mmol) in anhydrous $CH_2Cl_2$ (5 mL), 2-cyanoethyl)-N,N-diisopropylchlorophosphoramidite (0.1 g, 0.45 mmol) and diisopropyl ethylamine (72 mg, 0.56 mmol) was added under argon atmosphere. The mixture was stirred at r. t. for 40 min, following by diluting with $CH_2Cl_2$. The reaction solution was washed with 5% aq.

NaHCO$_3$ solution and brine, and then dried over anhydrous Na$_2$SO$_4$. After evaporation, the residue was submitted to flash chromatography (EtOAc/CH$_2$Cl$_2$/Et$_3$N: 100/25/1) to yield 55a (0.18 g, 70%) as a white foam. $^1$H NMR (CDCl$_3$, 300 MHz): δ 1.17-1.20 (m, 12H), 2.30-2.70 (m, 4H), 3.30-3.65 (m, 6H), 3.89 (s, 6H), 4.02-4.20 (m, 3H), 4.80-4.90 (m, 1H), 6.39 (t, J=6.0 Hz, 1H), 6.77-6.89 (m, 5H), 7.07-7.10 (m, 1H), 7.2-7.42 (m, 10H), 8.22 (s, 1H); $^{13}$C NMR (CDCl$_3$, 75 MHz): δ 162.0, 159.1, 149.7, 149.4, 143.8, 140.7, 140.5, 136.1, 134.6, 130.2, 128.4, 128.1, 123.6, 119.3, 117.4, 108.3, 85.5, 85.0, 71.8, 61.8, 58.0, 57.7, 55.2, 43.6, 43.3, 43.1, 24.5, 24.4, 20.2, 20.1; 31P NMR (CDCl$_3$, 121 MHz): δ 150.0, 150.2; HRMS-ES (m/z) [M−H]$^-$ calcd. for C$_{43}$H$_{49}$N$_7$O$_{10}$P, 854.3279. Found, 854.3282.

5'-O-(4,4'-Dimethoxytriphenylmethyl)-5-(2-nitro-1H-imidazol-1-yl)methyl-2'-deoxy uridine-3'-(2-cyanoethyl)-N,N-diisopropylphosphoramidite (55b)

To a solution of 54b (0.2 g, 0.31 mmol) in anhydrous CH$_2$Cl$_2$ (5 mL), 2-cyanoethyl)-N,N-diisopropylchlorophosphoramidite (0.1 g, 0.45 mmol) and diisopropyl ethylamine (72 mg, 0.56 mmol) was added under argon atmosphere. The mixture was stirred at r. t. for 30 min, then diluted with CH$_2$Cl$_2$. The reaction solution was washed with 5% aq. NaHCO$_3$ solution and brine, then dried over anhydrous Na$_2$SO$_4$. After evaporation, the residue was submitted to flash chromatography (EtOAc/CH$_2$Cl$_2$/Et$_3$N: 100/25/1) to give 55b (0.17 g, 68%) as a pale-yellow foam. $^1$H NMR (CDCl$_3$, 300 MHz): δ 1.18 (t, J=6.3 Hz, 12H), 2.30-2.38 (m, 1H), 2.47 (t, J=6.0 Hz, 2H), 2.52-2.59 (m, 1H), 3.43-3.73 (m, 6H), 3.80 (s, 6H), 4.19-4.25 (m, 1H), 4.59-4.67 (m, 1H), 4.77 (s, 2H), 6.30 (t, J=6.0 Hz, 1H), 6.85 (d, J=8.4 Hz, 4H), 7.07 (s, 1H), 7.22-7.36 (m, 8H), 7.45 (d, J=7.5 Hz, 1H), 8.08 (s, 1H); $^{13}$C NMR (CDCl$_3$, 75 MHz): δ 162.2, 159.7, 149.4, 144.4, 141.5, 135.4, 130.3, 128.3, 127.9, 127.8, 127.5, 127.1, 117.4, 113.2, 107.3, 86.8, 85.7, 85.5, 72.5, 62.9, 60.4, 58.0, 55.3, 43.4, 43.2, 24.7, 24.6, 24.5, 21.1, 20.3, 20.2; $^{31}$P NMR (CDCl$_3$, 121 MHz): δ 149.3, 149.2; HRMS-ES (m/z) [M+Na]$^+$ calcd. for C$_{43}$H$_{50}$N$_7$O$_{10}$PNa, 878.3255. Found, 878.3288

Example 11

Interstrand Crosslink Activity of Compounds

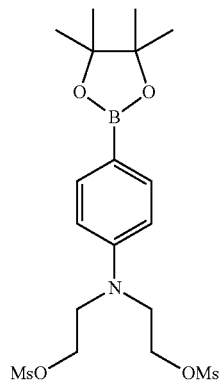

5

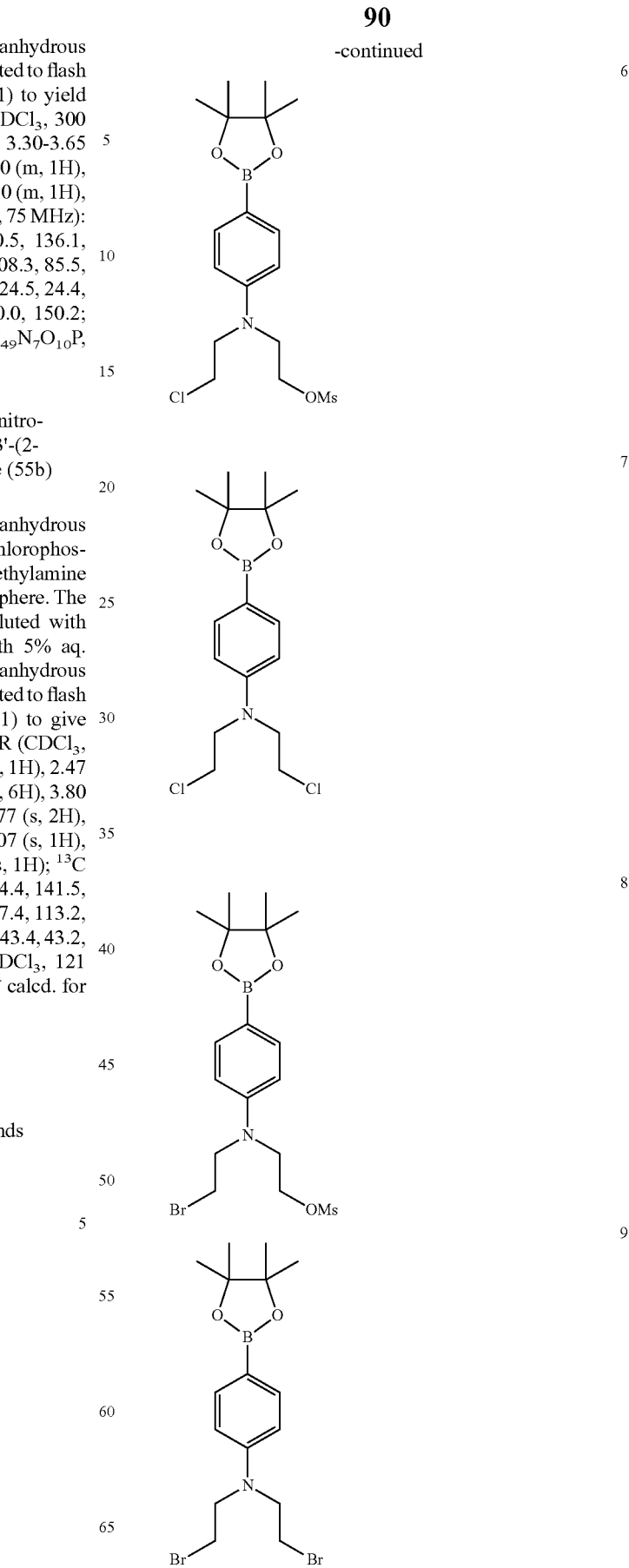

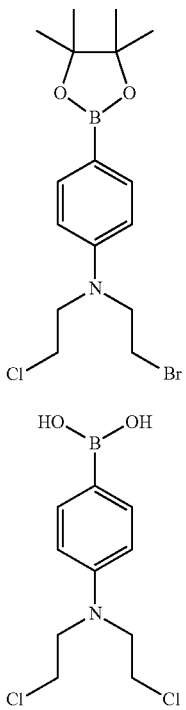

10

17a (SEQ ID NO: 1)
5'-dGCCTAGTTCTTTTAATTACTTGCAATGCAAGTAATTAAA
GCTTGATCTG (292a)

(SEQ ID NO: 2)
3'-dCGGATCAAGAAAATTAATGAACGTTACGTTCATTAATT
TCGAACTAGAC (292b)

The activity and selectivity of compounds 5-10 and 17a were investigated by determining their ability to form DNA interstrand crosslinks by cooperating with hydrogen peroxide and using a 49 mer DNA duplex 292. Aliquots (final concentration: 0.1 mM $^{32}$P-labeled oligonucleotide duplex, 100 mM NaCl, 10 mM potassium phosphate (pH 7.2), 2 mM $H_2O_2$, 2 mM of compound) were incubated at room temperature or at 37.5° C. respectively for 15 h and quenched by 90% formamide loading buffer, the resulting mixture was then subjected to 20% denaturing PAGE analysis. The comparison of the activity and selectivity of these derivatives towards $H_2O_2$ was revealed in the same gel. Results from room temperature experiments are illustrated in FIG. 1: Lane 1: 6 without $H_2O_2$; Lane 2: 6 with $H_2O_2$; Lane 3: 7 without $H_2O_2$; Lane 4: 7 with $H_2O_2$; Lane 5: 17a without $H_2O_2$; Lane 6: 17a with $H_2O_2$; Lane 7: 8 without $H_2O_2$; Lane 8: 8 with $H_2O_2$; Lane 9: 9 without $H_2O_2$; Lane 10: 9 with $H_2O_2$; Lane 11: 10 without $H_2O_2$; Lane 12: 10 with $H_2O_2$; Lane 13: 5 without $H_2O_2$; Lane 14: 5 with $H_2O_2$.

Very low ICL yield (less than 2.5%) with all the compounds except for 5 was observed in the absence of hydrogen peroxide. By contrast, under the same conditions, the addition of hydrogen peroxide increased dramatically the ICL yield to 37-50%. This obvious change clearly demonstrates that $H_2O_2$ can help to release the activity of these derivatives. The same experiments were performed at 37.5° C., and the results were similar.

Example 12

Activities of Compounds in Cancer Cells

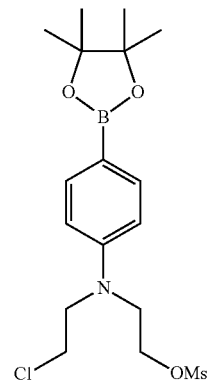

6

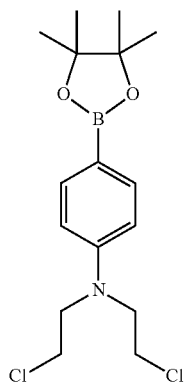

7

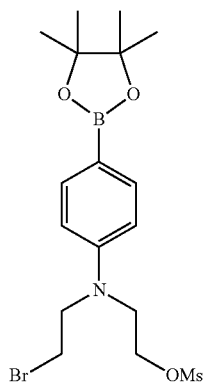

8

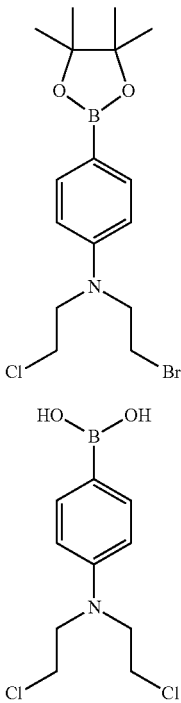

17a

Cytotoxicities of compounds 6, 7, 8, 10 and 17a were determined in the cell lines of leukemia, non-small cell lung cancer, colon cancer, CNS cancer, melanoma, ovarian cancer, renal cancer, prostate cancer and breast cancer, which have been reported to have higher levels of reactive oxygen species compared to normal cells. These compounds were screened using the NCI 60 human tumor cell line panel. In this assay, the human tumor cell lines of the cancer screening panel are grown in RPMI 1640 medium containing 5% fetal bovine serum and 2 mM L-glutamine. For a typical screening experiment, cells are inoculated into 96 well microtiter plates in 100 µL at plating densities ranging from 5,000 to 40,000 cells/well depending on the doubling time of individual cell lines. After cell inoculation, the microtiter plates are incubated at 37° C., 5% CO2, 95% air and 100% relative humidity for 24 h prior to addition of experimental drugs.

After 24 h, two plates of each cell line are fixed in situ with TCA, to represent a measurement of the cell population for each cell line at the time of drug addition (Tz). Experimental drugs are solubilized in dimethyl sulfoxide at 400-fold the desired final maximum test concentration and stored frozen prior to use. At the time of drug addition, an aliquot of frozen concentrate is thawed and diluted to twice the desired final maximum test concentration with complete medium containing 50 µg/ml gentamicin. Additional four, 10-fold or ½ log serial dilutions are made to provide a total of five drug concentrations plus control. Aliquots of 100 µl of these different drug dilutions are added to the appropriate microtiter wells already containing 100 µl of medium, resulting in the required final drug concentrations.

Following drug addition, the plates are incubated for an additional 48 h at 37° C., 5% CO2, 95% air, and 100% relative humidity. For adherent cells, the assay is terminated by the addition of cold TCA. Cells are fixed in situ by the gentle addition of 50 µl of cold 50% (w/v) TCA (final concentration, 10% TCA) and incubated for 60 minutes at 4° C. The supernatant is discarded, and the plates are washed five times with tap water and air dried. Sulforhodamine B (SRB) solution (100 µl) at 0.4% (w/v) in 1% acetic acid is added to each well, and plates are incubated for 10 minutes at room temperature. After staining, unbound dye is removed by washing five times with 1% acetic acid and the plates are air dried. Bound stain is subsequently solubilized with 10 mM trizma base, and the absorbance is read on an automated plate reader at a wavelength of 515 nm. For suspension cells, the methodology is the same except that the assay is terminated by fixing settled cells at the bottom of the wells by gently adding 50 µl of 80% TCA (final concentration, 16% TCA). Using the seven absorbance measurements [time zero, (Tz), control growth, (C), and test growth in the presence of drug at the five concentration levels (Ti)], the percentage growth is calculated at each of the drug concentrations levels. Percentage growth inhibition is calculated as:

[(Ti−Tz)/(C−Tz)]×100 for concentrations for which Ti>/=Tz

[(Ti−Tz)/Tz]×100 for concentrations for which Ti<Tz.

Three dose response parameters are calculated for each experimental agent. Growth inhibition of 50% ($GI_{50}$) is calculated from [(Ti−Tz)/(C−Tz)]×100=50, which is the drug concentration resulting in a 50% reduction in the net protein increase (as measured by SRB staining) in control cells during the drug incubation. The drug concentration resulting in total growth inhibition (TGI) is calculated from Ti=Tz. The $LC_{50}$ (concentration of drug resulting in a 50% reduction in the measured protein at the end of the drug treatment as compared to that at the beginning) indicating a net loss of cells following treatment is calculated from [(Ti−Tz)/Tz]×100=−50. Values are calculated for each of these three parameters if the level of activity is reached; however, if the effect is not reached or is exceeded, the value for that parameter is expressed as greater or less than the maximum or minimum concentration tested Compounds showed good inhibition ability towards the cell lines at the concentration of 10 µM, and the growth percents of most cell lines were less than 50%. Results are illustrated in FIG. 2A, 2B, 2C, 2D and 2E for compounds 6, 7, 8, 10 and 17a respectively.

Compounds 6, 7, 10 and 17a were further tested to evaluate $GI_{50}$ values (the concentration required to achieve 50% growth inhibition) in cancer cell lines. Compounds exhibited a high level of toxicity to the cell lines tested and most of them have $GI_{50}$ values of less than 5 µM. Particularly these compounds are highly toxic towards SR (Leukemia), NCI-H460 (Non-Small Cell Lung Cancer), and MDA-MB-468 (breast cancer) with GI50 less than 1 µM (Table 1). It is likely that these cell lines have high level of ROS.

TABLE 1

| | | $GI_{50}$ (µM) | | | |
|---|---|---|---|---|---|
| Tumor | Cell Line | 6 | 7 | 10 | 17a |
| Leukemia | CCRF-CEM | 4.01 | 3.34 | 5.03 | 3.27 |
| | HL-60(TB) | 3.88 | 4.66 | 5.11 | 2.88 |
| | MOLT-4 | 3.74 | 3.48 | 3.69 | 2.90 |
| | RPMI-8226 | 14.7 | 10.90 | 19.40 | 8.59 |
| | SR | 0.63 | 0.63 | 0.66 | 0.48 |
| Non-Small Cell Lung Cancer | A549/ATCC | 4.98 | 2.69 | 4.88 | 0.89 |
| | HOP-92 | 11.5 | 9.24 | 12.80 | 10.50 |
| | NCI-H23 | 4.70 | 4.57 | 5.38 | 3.36 |
| | NCI-H460 | 0.49 | 0.33 | 0.42 | 0.23 |
| | NCI-H522 | 5.99 | 6.59 | 11.70 | 3.53 |
| Colon | COLO 205 | 11.00 | 11.60 | 11.40 | 7.26 |

TABLE 1-continued

| Tumor | Cell Line | GI$_{50}$ (μM) | | | |
|---|---|---|---|---|---|
| | | 6 | 7 | 10 | 17a |
| Cancer | HCT-116 | 11.10 | 11.60 | 13.90 | 9.37 |
| | HCT-15 | 13.50 | 13.20 | 17.10 | 9.46 |
| | SW-620 | 11.90 | 11.30 | 13.90 | 8.39 |
| CNS | SF-268 | 5.39 | 4.61 | 4.90 | 4.72 |
| Cancer | SF-295 | 2.99 | 2.11 | 2.64 | 1.36 |
| | SF-539 | 4.83 | 5.70 | 6.37 | 3.35 |
| | SNB-19 | 10.20 | 8.06 | 10.60 | 8.00 |
| | SNB-75 | 5.85 | 7.98 | 10.70 | 3.21 |
| | U251 | 0.70 | 3.75 | 5.07 | 3.49 |
| Melanoma | LOX IMVI | 4.72 | 5.17 | 6.60 | 3.13 |
| | M14 | 5.68 | 5.10 | 7.86 | 4.77 |
| | UACC-62 | 5.83 | 6.12 | 9.38 | 4.71 |
| Ovarian | OVCAR-8 | 8.20 | 7.83 | 11.90 | 4.20 |
| | NCI/ADR-RES | 6.52 | 5.33 | 6.69 | 2.69 |
| | SK-OV-3 | 8.96 | 8.03 | 9.25 | 3.81 |
| Renal | 786-0 | 6.55 | 5.35 | 8.95 | 4.04 |
| Cancer | A498 | 8.59 | 2.81 | 5.87 | 3.43 |
| | ACHN | 3.03 | 3.64 | 3.40 | 1.75 |
| | CAKI-1 | 3.10 | 2.78 | 3.52 | 1.44 |
| | RXF 393 | 5.71 | 4.11 | 4.45 | 2.55 |
| | UO-31 | 6.18 | 5.78 | 6.51 | 6.05 |
| Prostate | PC-3 | 15.10 | 14.30 | 17.70 | 15.10 |
| Cancer | DU-145 | 4.52 | 4.25 | 6.69 | 4.89 |
| Breast | MCF7 | 4.44 | 4.12 | 5.03 | 1.89 |
| Cancer | T-47D | 8.49 | 10.70 | 12.00 | 6.29 |
| | MDA-MB-468 | 1.07 | 1.60 | 1.49 | 0.51 |

Example 13

Interstrand Crosslink Activity of Compounds

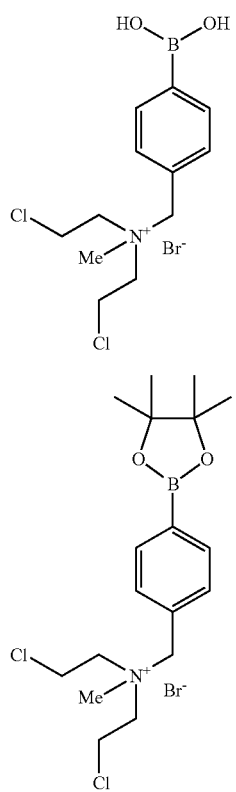

38

40

292

(SEQ ID NO: 1)
5'-dGCCTAGTTCTTTTAATTACTTGCAATGCAAGTAATTAAAGCTTGATCTG (292a)

(SEQ ID NO: 2)
3'-dCGGATCAAGAAAATTAATGAACGTTACGTTCATTAATTTCGAACTAGAC (292b)

Figure 3:
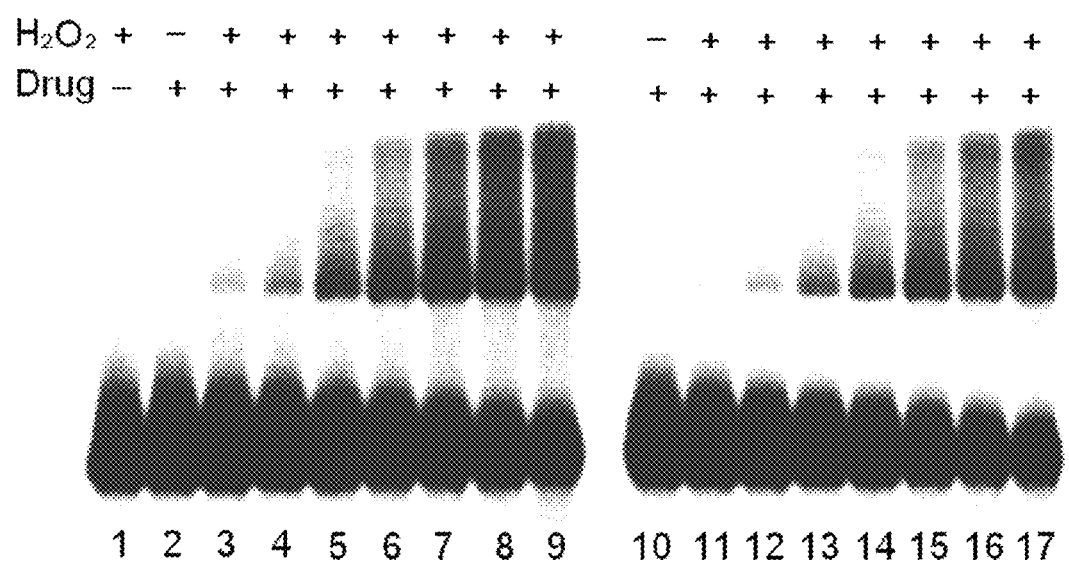
FIG. 3 depicts a denaturing PAGE gel of DNA samples treated with compounds described herein, in the presence or absence of hydrogen peroxide.

The activities of 38 and 40 were investigated by determining their ability to form DNA interstrand crosslinks using 49 mer DNA duplex 292. The DNA cross-linking experiments were carried out in phosphate buffer (pH=7.5). ICL formation and crosslinking yield were analyzed via denaturing polyacrylamide gel electrophoresis (PAGE) with phosphorimager analysis (Image Quant 5.2) by taking advantage of the differing mobilities of ICL products and single stranded DNA. Results are illustrated in FIG. 3: Lane 1 without drug; lanes 2-9 with drug 40: lane 2 without H$_2$O$_2$ (cross-linking yield 0%); lane 3: 50 μM H$_2$O$_2$+100 μM 40 (2.2%); lane 4: 100 μM H$_2$O$_2$+200 μM 40 (5%); lane 5: 250 μM H$_2$O$_2$+500 μM 40 (11%); lane 6: 500 μM H$_2$O$_2$+1.0 mM 40 (18%); lane 7: 1.0 mM H$_2$O$_2$+2.0 mM 40 (28%); lane 8: 1.5 mM H$_2$O$_2$+3.0 mM 40 (36%); lane 9: 2.0 mM H$_2$O$_2$+4.0 mM 40 (42%); lanes 10-17 with drug 38: lane 10 without H$_2$O$_2$ (0%); lane 11: 50 μM H$_2$O$_2$+100 μM 38 (2.0%); lane 12: 100 μM H$_2$O$_2$+200 μM 38 (4%); lane 13: 250 μM H$_2$O$_2$+500 μM 38 (11%); lane 14: 500 μM H$_2$O$_2$+1.0 mM 38 (17%); lane 15: 1.0 mM H$_2$O$_2$+2.0 mM 38 (27%); lane 16: 1.5 mM H$_2$O$_2$+3.0 mM 38 (35%); lane 17: 2.0 mM H$_2$O$_2$+4.0 mM 38 (43%).

In the absence of H$_2$O$_2$, no ICL was observed with 40 and 38 (FIG. 3, lanes 2 and 10), which indicates the toxicity of nitrogen mustard mechlorethamine (7) is masked in the prodrugs. When 292 was treated with 38 or 40 in the presence of H$_2$O$_2$, efficient crosslink formation was observed (35-45%) (FIG. 3, lanes 5-9 and 13-17). DNA crosslinking by 40 and 38 was observed at a concentration of H$_2$O$_2$ as low as 50 μM (lanes 3 and 11). This clearly shows that 38 and 40 are nontoxic to DNA, but can be activated by H$_2$O$_2$ to release the DNA damaging agent.

Example 14

Anti-Cancer Activities of Compounds

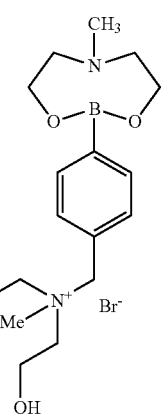

37

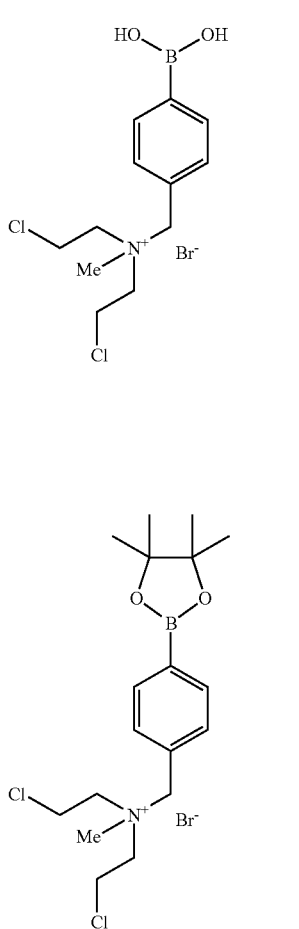

38

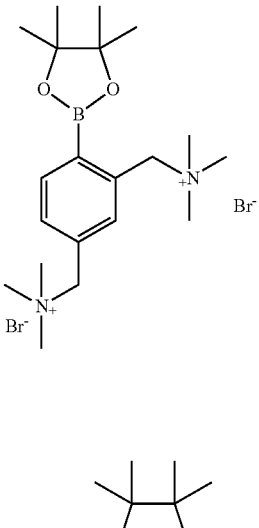

46

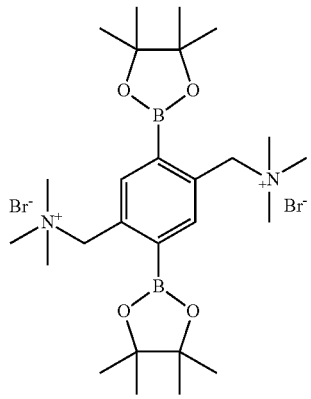

48

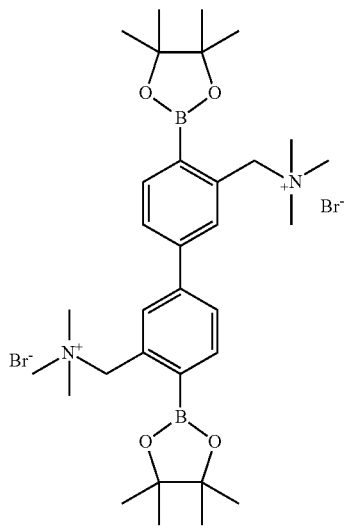

47

40

Figure 4:
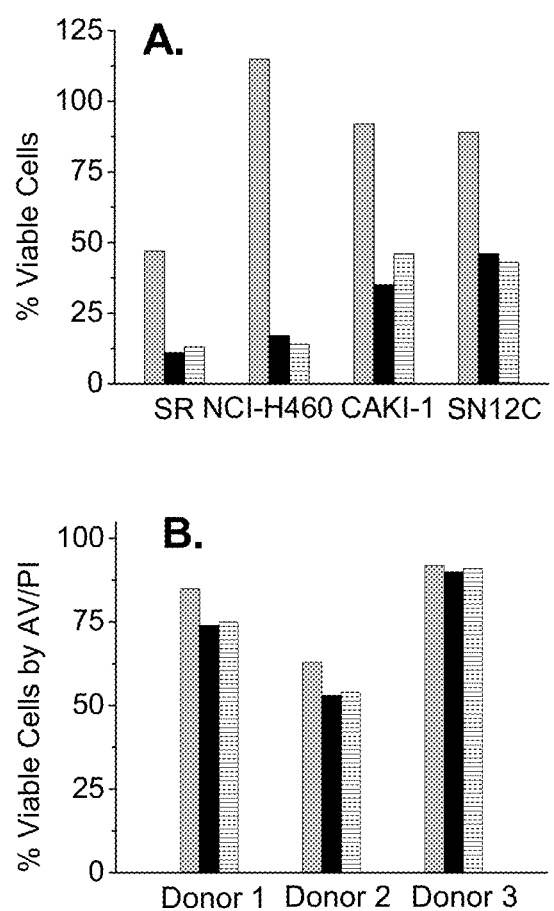
FIG. 4 depicts: (A) a graph of the percentage of viable cells from four cancer cell lines following treatment with compounds described herein; and (B) a graph of the percentage of viable cells from three healthy donor cell lines in the presence of three compounds described in Example 14.

The abilities of compounds 37, 38 and 40 to inhibit cancer cell growth were evaluated. Results are illustrated in FIG. 4A: Four human cancer cell lines (5R, NCI-H460, CAKI-1, and SN12C) were incubated with 10 μM of compounds 40, 38 and 37 for 48 h (grey bar—37; black bar—40; lined bar—38). Both compounds 38 and 40 inhibited various types of cancer cells at 10 μM. They showed about 90% inhibition toward SR cells (Leukemia cell), 85% inhibition toward NCI-H460 (Non-small Cell Lung Cancer cells), and 66% inhibition toward CAKI-1, and 57% toward SN12C (Renal Cancer cells) (FIG. 4A). However, compound 37 is less toxic to these cells. The toxicity of 38 and 40 is likely caused by the release of nitrogen mustard after tumor-specific activation.

In order to determine the selectivity, the toxicities of 38 and 40 were evaluated towards non-cancer cells. Normal lymphocytes obtained from healthy donors (n=3) were incubated with 10 μM of 38 and 40 for 48 h. Time matched control samples were set up concurrently. Results are illustrated in FIG. 4B (grey bar—control; black bar—compound 40; lined bar—compound 38). In all 3 samples studied, compared to time-matched controls, there was no increase in apoptosis observed between 24-72.

Figure 5:
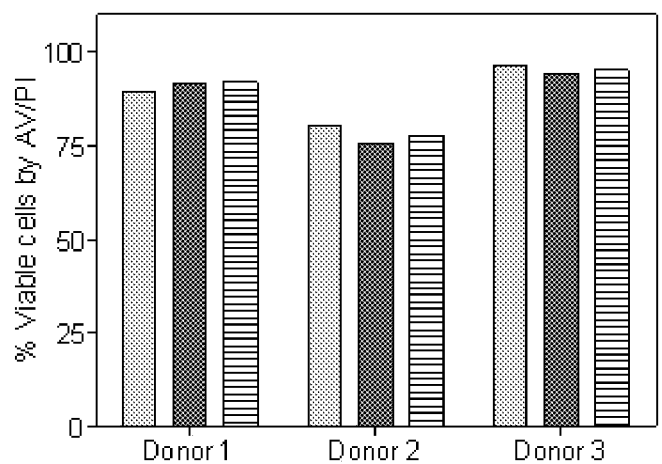
FIG. 5 depicts graphs of the percentage of viable cells from three healthy donor cell lines following treatment with compounds described herein for: (A) 24 hr; (B) 48 hr; and (C) 72 hr.
Figure 5:
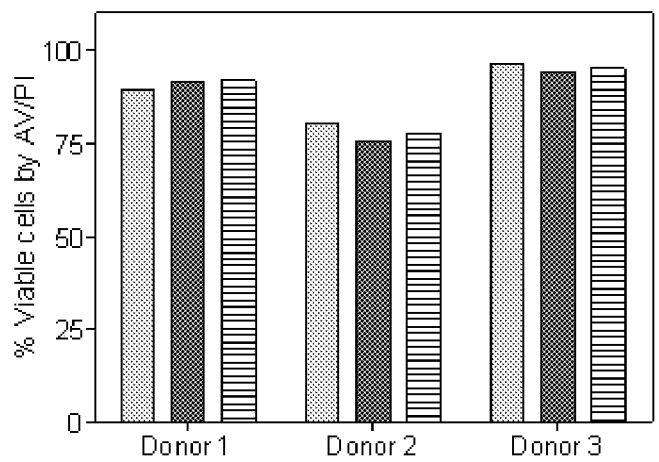
Figure 5:
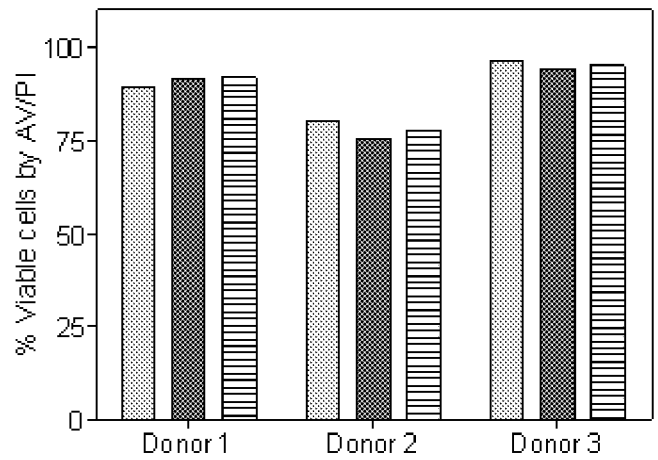

Normal lymphocytes obtained from healthy donors (n=3) were incubated with 10 μM of compounds 38 and 40 for 24 hr (A); 48 hr (B); and 72 hr (C). Results are illustrated in FIG. 5. The percent viable cells were obtained from the left quadrant of dot plot that has annexin negative and PI negative population of cells. Time matched control samples are set up concurrently (grey bar—control; black bar—compound 40; lined bar—compound 38).

Example 15

Interstrand Crosslink Activity of Compounds

292

(SEQ ID NO: 1)
5′-dGCCTAGTTCTTTTAATTACTTGCAATGCAAGTAATTAAA
GCTTGATCTG (292a)

(SEQ ID NO: 2)
3′-dCGGATCAAGAAAATTAATGAACGTTACGTTCATTAATT
TCGAACTAGAC (292b)

Figure 6:
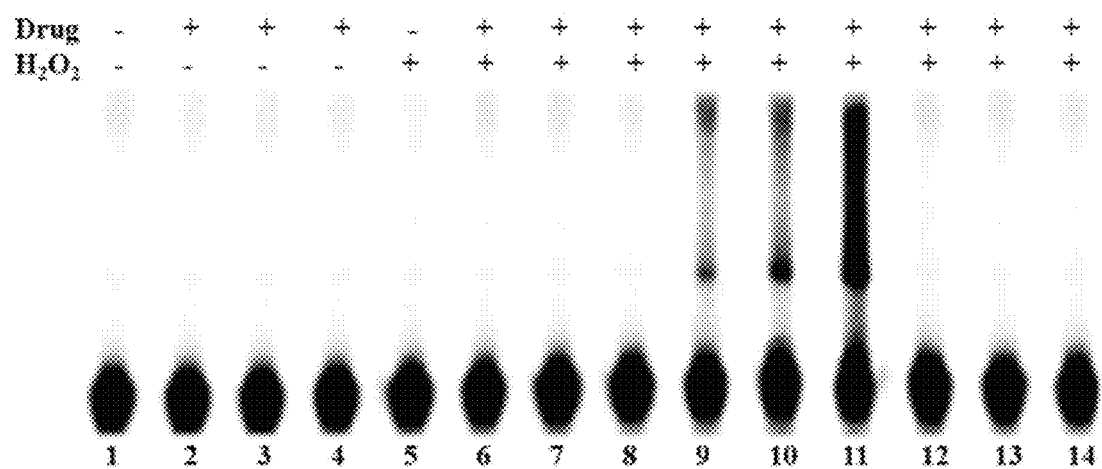
FIG. 6 depicts a denaturing PAGE gel of DNA samples treated with compounds described herein, in the presence or absence of hydrogen peroxide.

The activity of compounds 46-48 towards DNA was investigated using a 49 mer DNA duplex 292 by measuring DNA ICL formation. The reactions of 46-48 with DNA were carried out in phosphate buffer (pH=8.0) at 37° C. ICL formation and cross-linking yield were analyzed via denaturing polyacrylamide gel electrophoresis (PAGE) with phosphorimager analysis (Image Quant 5.2). Results are illustrated in FIG. 6: Lane 1: DNA only (cross-linking yield 0%); lane 2: DNA with 46 (2 mM) only (cross-linking yield 4%); lane 38 DNA with 48 (2 M) only (cross-linking yield 0%); lane 4: DNA with 47 (2 mM) only (cross-linking yield 0%); lane 5: DNA with $H_2O_2$ (10 μM) only (cross-linking yield 0%); lane 6: 10 μM 46+5 μM $H_2O_2$ (0%); lane 7: 100 μM 46+50 μM $H_2O_2$ (0%); lane 8: 2 mM 46+1 mM $H_2O_2$ (0%); lane 9: 10 μM 48+5 μM $H_2O_2$ (2%); lane 10: 100 μM 48+50 μM $H_2O_2$ (8%); lane 11: 2 mM 48+1 mM $H_2O_2$ (24%); lane 12: 10 μM 47+5 μM $H_2O_2$ (0%); lanes 13: 100 μM 47+50 μM $H_2O_2$ (0%); lane 14: 2 mM 47+1 mM $H_2O_2$ (0%).

In the absence of $H_2O_2$, ICLs were not observed with 46-48 (FIG. 6, lanes 2-4), which indicated that QM was not formed. In the presence of $H_2O_2$, compound 48 efficiently induce the ICL formation (FIG. 6, lanes 9-11). However, no ICL was observed with 46 and 47 (FIG. 6, lanes 6-8 and 12-14).

Example 16

Interstrand Crosslink Activity of Compounds

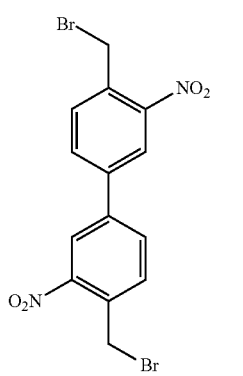

59

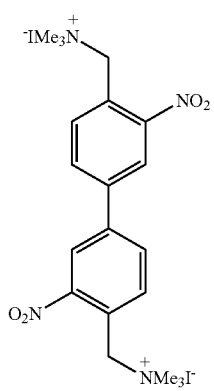

58b

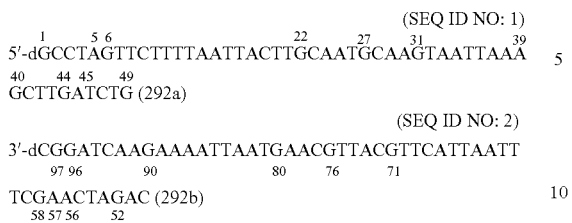

58c

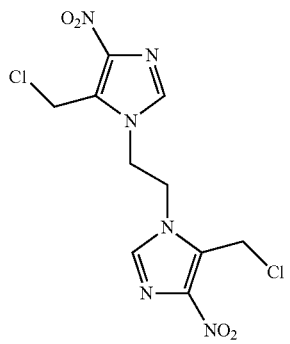

65

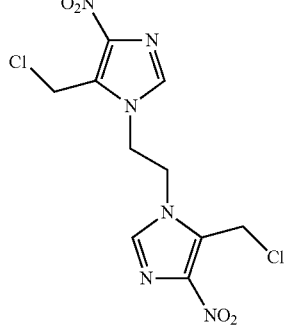

66

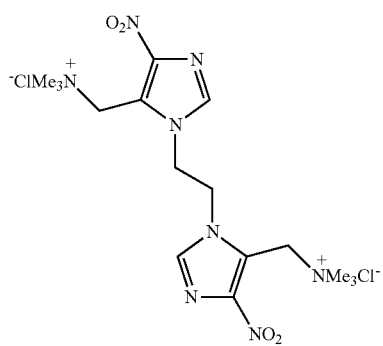

67

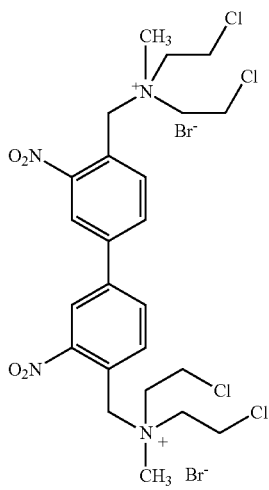

61

Figure 7:
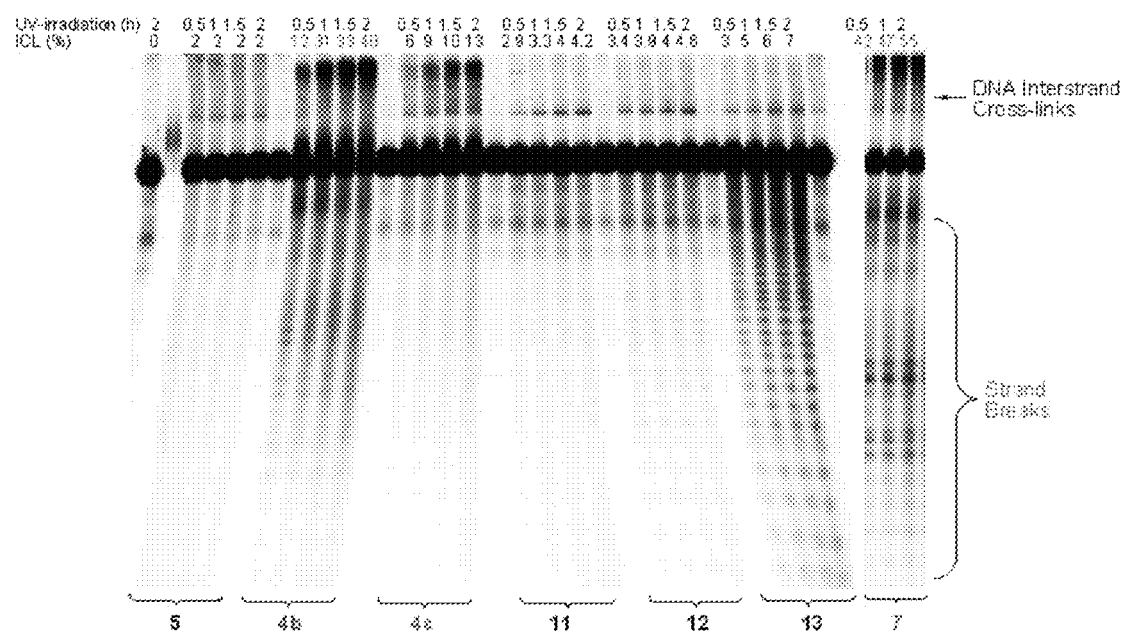
FIG. 7 depicts a denaturing PAGE gel of DNA samples incorporating compounds described herein, following irradiation (350 nm).

The compounds shown above were incubated with DNA and irradiated by UV (350 nm). Basically all compounds induced DNA interstrand cross-link formation under hypoxic conditions. Results are illustrated in FIG. 7. Higher cross-linking yields were observed for compounds 58b and 61 which contain nitro group and quaternary ammonium group. Compound 58b, 61 and 67 induced direct strand breaks. Overall, the compounds are good hypoxia sensitizers.

Example 17

Interstrand Crosslink Activity of Compounds

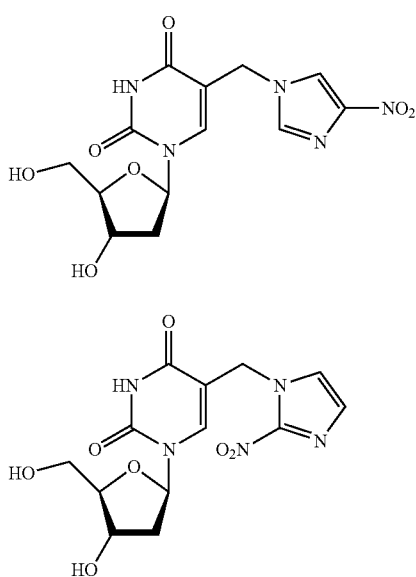

53a

53b

Oligonucleotides containing 53a or 53b were synthesized via automated solid-phase synthesis. The coupling yields were more than 98%.

```
        (SEQ ID NO: 3)                  (SEQ ID NO: 5)
5'-dAGATGGAN53aNAGGTAC 5'-dAGATGGAN53bNAGGTAC (SEQ ID NO: 4)                  (SEQ ID NO: 6)
3'-dTCTACCTN'AN'TCCATG 3'-dTCTACCTN'AN'TCCATG
```

DNA duplexes 6-13 were photo-irradiated at 350 nm using a Rayonet Photochemical Chamber Reactor (Model RPR-100). A wavelength of 350 nm was chosen because near-UV light (>300 nm) is not/slightly absorbed by most biological molecules and is compatible with living cells. Both compounds have absorbance at 350 nm (A=0.08 for 0.023 mM 53a and A=0.19 for 0.023 mM 53b. Furthermore, the nitroimidazole derivatives can be excited by 350 nm to form a radical anion transition state.

Figure 8:
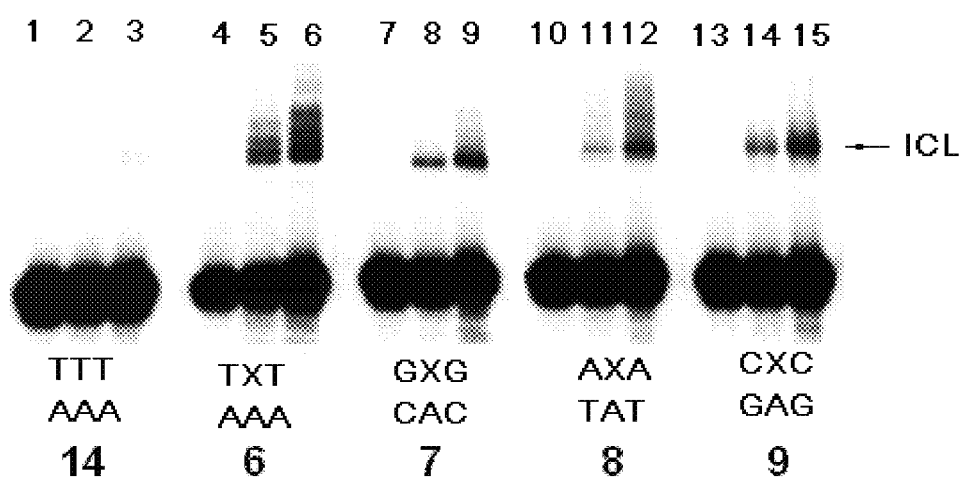
FIG. 8 depicts a denaturing PAGE gel of DNA samples incorporating compounds described herein, following irradiation (350 nm).

$^{32}$P-labelled oligonucleotide (1.0 M) was annealed with 1.5 equiv of the complementary strand by heating to 65° C. for 3 min in buffer (10 mM potassium phosphate, pH 7.5, and 100 mM NaCl), followed by slow-cooling to room temperature overnight. The $^{32}$P-labeled oligonucleotide duplex (2 μL, 1.0 μM) was mixed with 1 M NaCl (2 μL), 100 mM potassium phosphate (2 μL, pH 7.5) and appropriate amount of autoclaved distilled water to give a final volume of 20 μL. The mixture was degassed to remove the air and purged with argon, then UV-irradiated in a Rayonet Photochemical Chamber Reactor (Model RPR-100, sixteen bulbs, 350 nm light wavelength) for 2 h. The reaction was quenched by an equal volume of 90% formamide stop/loading buffer, then electrophoresed on a 20% denaturing polyacrylamide gel at 1200 V for approximately 4 h. Results are shown in FIG. 8: Lanes 1, 4, 7, 10 and 13, DNA duplexes without UV irradiation; Lanes 2, 5, 8, 11 and 14, DNA duplexes irradiated under aerobic condition; Lanes 3, 6, 9, 12 and 15, DNA duplexes irradiated under anaerobic condition.

The UV-photolysis of ODN 6 resulted in a new band whose migration is severely retarded relative to unreacted oligonucleotide, indicative of interstrand cross-linked material (FIG. 8). The cross-linking yield under hypoxic condition (3.6%) is 1.6 times higher than that under aerobic condition (2.2%) (FIG. 8, lanes 5 vs. 6). Cross-link formation with duplexes ODN 7-9 were also examined, in which 53a is flanked by different sequences (FIG. 8, lanes 8 vs. 9, 11 vs. 12, 14 vs. 15). In all cases, hypoxic conditions resulted in higher cross-linking yield than aerobic conditions (FIG. 9A). This further demonstrated the hypoxia-selective cross-linking formation induced by 53a. In a control experiment, an otherwise identical duplex (ODN 14) containing dT in place of 53a was irradiated by UV, while less than 0.2% ICL was observed under both aerobic and anaerobic conditions. This indicated that the nitroimidazole group in 53a plays an integral role in ICL formation and hypoxia-selectivity in 6-9. In order to determine the generality of this property, 2-nitroimidazole modified thymidine was synthesized (53b), and its ability for ICL formation was examined. Similarly, higher cross-linking yield was observed under hypoxic conditions than that under aerobic conditions when the duplexes containing 53b (10-13) were irradiated at 350 nm (FIG. 9B).

Figure 9:
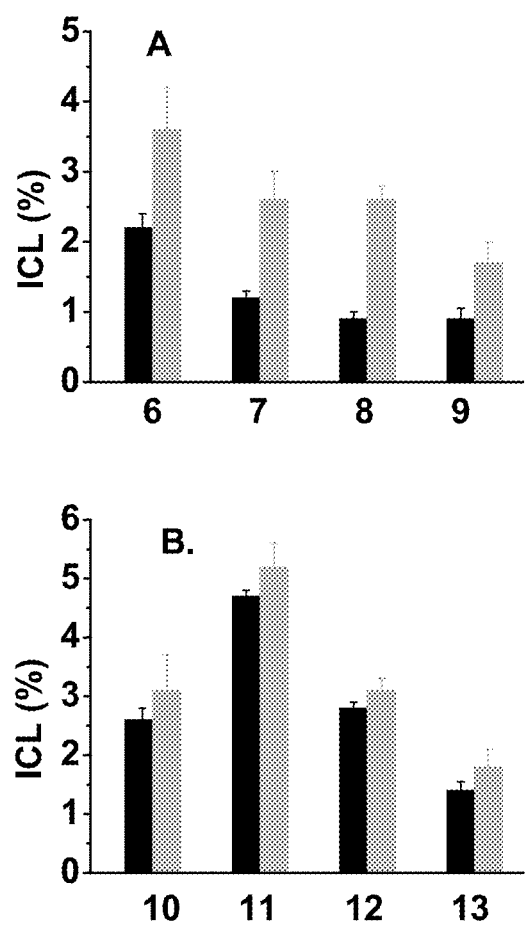
FIG. 9 depicts graphs of the percentage of interstrand crosslinks (ICLs) of DNA samples incorporating compounds described in Example 17, following irradiation (350 nm). Black bar—aerobic conditions (air); grey bar—anaerobic conditions (Ar). (A) DNA duplexes incorporating compound 53a; (B) DNA duplexes incorporating compound 53b.

In FIG. 9: (A) Duplexes containing 53a (6-9) were irradiated by UV for 2 h; (B) Duplexes containing 53b (10-13) were UV-irradiated for 2 h [black bar—aerobic conditions (air); grey bar—anaerobic conditions (Ar)].

Example 18

Tests of Compounds in Xenografts

Xenograft experiments will be carried out essentially as described in Cheng et al. *Cancer Research* 2012, 72(10):

2634-44. MDA-MB-231-luc cells [5×10$^5$ cells in 200 mL of a mixture of 1:1 PBS/Matrigel (BD Biosciences)] will be injected into the right mammary fat-pad of 8-week-old female SHO mice (Charles River). Tumor establishment and growth will be monitored by injecting D-luciferin per manufacturer's instructions (Caliper Life Sciences) and detecting bioluminescence using the Lumina IVIS-100 In Vivo Imaging System (Xenogen Corp). The light intensities emitted from regions of interest will be expressed as total flux (photons/s). Two days after injection of cells, the mice will be imaged to verify tumor establishment. Mice will be either orally gavaged, injected intraperitoneally, or injected intravenously with either water (control), Mito-CP (40 mg/kg), 2-DG (1 g/kg), or a mixture of Mito-CP (40 mg/kg, final concentration) and 2-DG (1 g/kg, final concentration) 5 times/wk (Monday through Friday). This treatment protocol was selected based on recent studies showing that Mito-CP is cleared from plasma of mice within approximately 6 hours of injection (Mukhopadhyay et al. *Free Radic Biol Med* 2012; 52:497-506.). After 4 weeks of treatment, the mice will be sacrificed, and the tumor, kidney, heart, and liver will be removed and formalin fixed. These tissues will be paraffin embedded and stained with hematoxylin and eosin (H&E).

The invention claimed is:

1. A compound of formula (I):

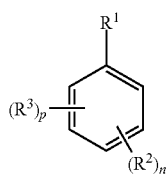

(I)

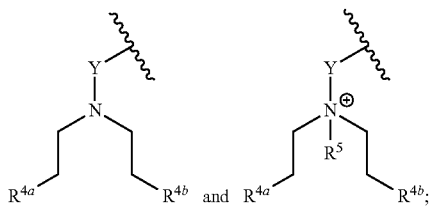

wherein:

each $R^1$ is independently —B(XR')$_2$, wherein each X is independently selected from O and S, and each R' is independently selected from hydrogen and alkyl, or two R' are taken together to form an optionally substituted 5- to 8-membered ring;

each $R^2$ is independently selected from optionally substituted alkyl, alkoxy, amino, halo, and —CH$_2$—N(R$^a$)$_3\oplus$;

each $R^3$ is independently selected from:

each $R^{4a}$ and $R^{4b}$ is independently selected from halo and —OSO$_2$R$^a$;

each Y is independently a bond or —CH$_2$—;

each $R^5$ is independently C$_1$-C$_4$ alkyl;

n is 0, 1 or 2;

p is 1 or 2;

each $R^a$ is independently selected from optionally substituted alkyl;

wherein if the compound of formula (I) bears a positive charge, it further comprises at least one counterion Z⊖.

2. The compound of claim 1, wherein the compound is selected from:

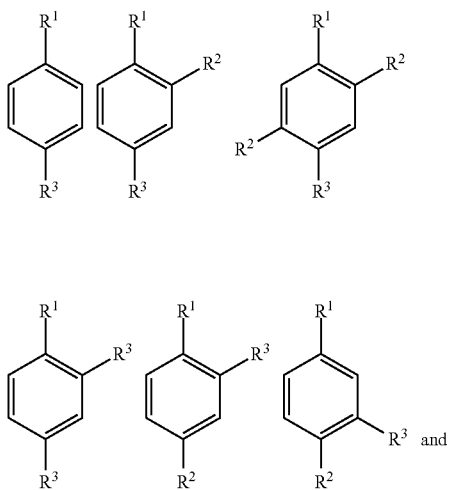

3. A pharmaceutical composition comprising a compound of claim 1.

4. The compound of claim 1, wherein $R^1$ is selected from the group consisting of:

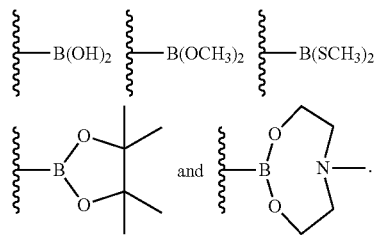

5. The compound of claim 1, wherein $R^1$ is selected from the group consisting of:

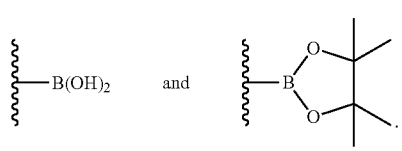

6. The compound of claim 1, wherein n is 0.

7. The compound of claim 1, wherein n is 1.

8. The compound of claim 7, wherein $R^2$ is methyl.

9. The compound of claim 1, wherein $R^3$ is selected from the group consisting of:

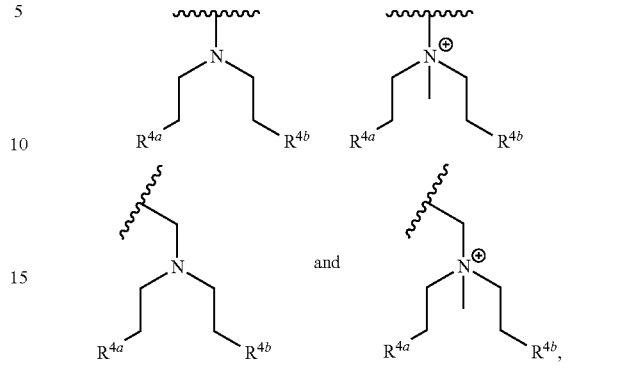

wherein each $R^{4a}$ and $R^{4b}$ is independently selected from chloro, bromo, and —OSO$_2$CH$_3$.

10. The compound of claim 1, wherein the compound is selected from the group consisting of:

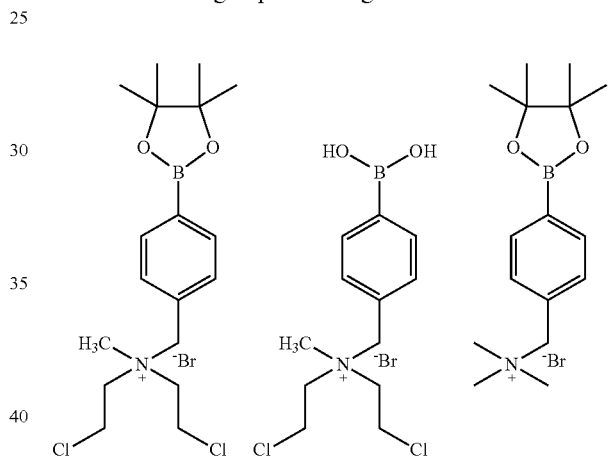

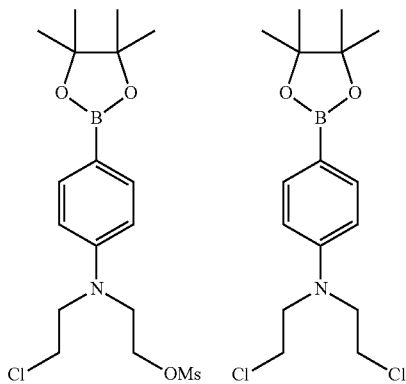

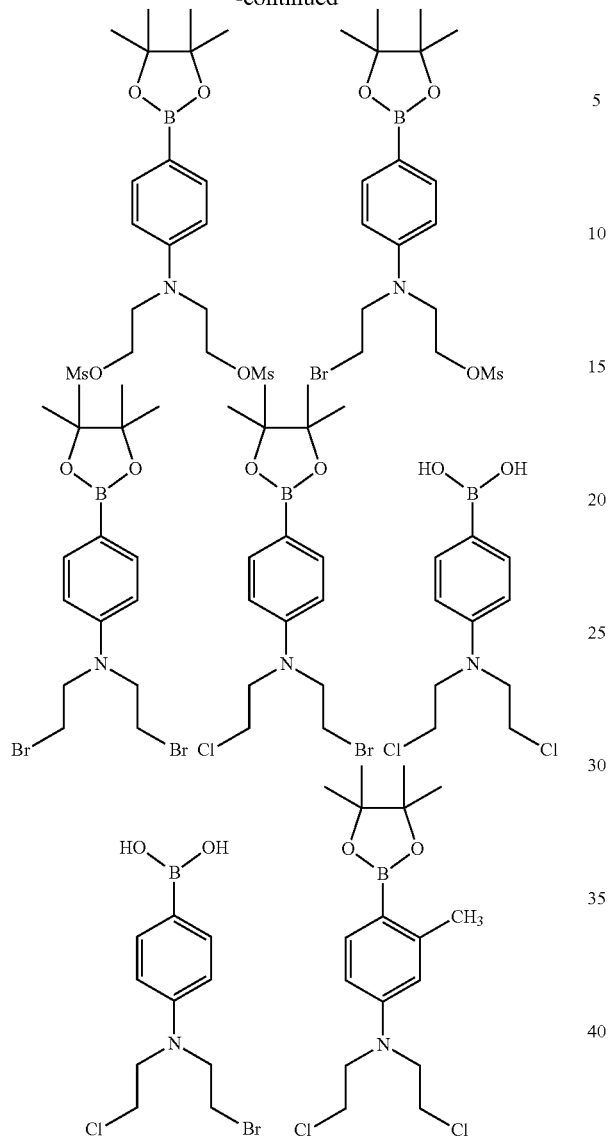
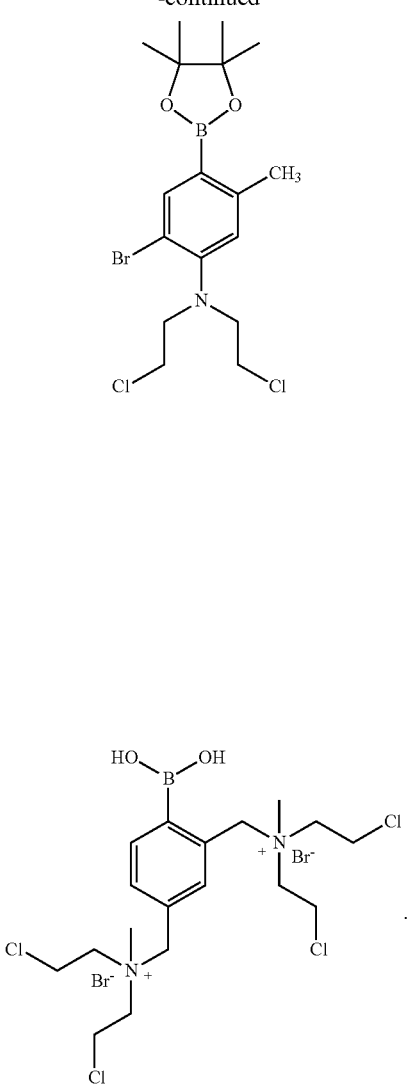
* * * * *

UNITED STATES PATENT AND TRADEMARK OFFICE
CERTIFICATE OF CORRECTION

PATENT NO. : 8,637,490 B2
APPLICATION NO. : 13/539471
DATED : January 28, 2014
INVENTOR(S) : Xiaohua Peng et al.

It is certified that error appears in the above-identified patent and that said Letters Patent is hereby corrected as shown below:

In the specification

Column 1, line 25    Replace:
[[This invention was made with United States government
support awarded by the National Cancer Institute, Grant No.
1R15CA152914-01. The United States Government has certain rights
in this invention.]]

with:
---This invention was made with government support under
1R15CA152914-01 awarded by the National Institutes of Health
(NIH). The government has certain rights in the invention.---

Signed and Sealed this
Fifth Day of January, 2016

Michelle K. Lee
*Director of the United States Patent and Trademark Office*